United States Patent
Ono et al.

(10) Patent No.: US 8,580,523 B2
(45) Date of Patent: Nov. 12, 2013

(54) SPECIFIC MARKER LMX1A ON DOPAMINERGIC NEURONS

(75) Inventors: Yuichi Ono, Kyoto (JP); Yasuko Nakagawa, Kyoto (JP); Tomoya Nakatani, Kyoto (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/352,241

(22) Filed: Jan. 17, 2012

(65) Prior Publication Data

US 2012/0178083 A1  Jul. 12, 2012

Related U.S. Application Data

(62) Division of application No. 10/580,989, filed as application No. PCT/JP2004/017574 on Nov. 26, 2004, now Pat. No. 8,187,804.

(30) Foreign Application Priority Data

Nov. 26, 2003  (JP) .................. 2003-395493

(51) Int. Cl.
*C12N 5/0793* (2010.01)
*C12N 5/071* (2010.01)
*C12N 5/00* (2006.01)
*C12N 5/07* (2010.01)
*C12Q 1/68* (2006.01)
*G01N 33/53* (2006.01)
*G01N 33/58* (2006.01)

(52) U.S. Cl.
USPC ............ 435/7.1; 435/7.21; 435/6.1; 435/325; 435/368; 435/354

(58) Field of Classification Search
None
See application file for complete search history.

(56) References Cited

U.S. PATENT DOCUMENTS

| | | |
|---|---|---|
| 2002/0155423 A1 | 10/2002 | Okano et al. |
| 2006/0239978 A1 | 10/2006 | Nakagawa et al. |
| 2006/0240432 A1 | 10/2006 | Ono et al. |
| 2008/0311091 A1 | 12/2008 | Perlmann et al. |
| 2010/0203570 A1 | 8/2010 | Nakagawa et al. |
| 2010/0323366 A1 | 12/2010 | Ono et al. |

FOREIGN PATENT DOCUMENTS

| | | |
|---|---|---|
| WO | WO 02/063938 A2 | 8/2002 |
| WO | WO03010329 * | 2/2003 |
| WO | WO 2004/038018 A1 | 2/2004 |
| WO | WO 2004/048573 A1 | 6/2004 |
| WO | WO 2004/065599 A1 | 8/2004 |

OTHER PUBLICATIONS

Failli, Vieri et al.; "Expression of the LIM-homeodomain gene Lmx1a (dreher) during development of the mouse nervous system"; *Mechanisms of Development*, vol. 118, pp. 225-225 (2002).

(Continued)

*Primary Examiner* — Jeffrey Stucker
*Assistant Examiner* — Aurora M Fontainhas
(74) *Attorney, Agent, or Firm* — Fish & Richardson P.C.

(57) ABSTRACT

The present invention identified Lmx1a genes, which are expressed in dopaminergic neurons at all differentiation stages, from proliferating dopaminergic neuron progenitor cells before cell cycle exit to cells after cell cycle exit. Lmx1a expression in cells can be used as an indicator when selecting cells suitable for transplantation therapy for neurodegenerative diseases such as Parkinson's disease, and is useful as a marker for screening agents involved in the induction of dopaminergic neuron differentiation.

17 Claims, 8 Drawing Sheets

(56) References Cited

OTHER PUBLICATIONS

Holzschuh, "Dopamine transporter expression distinguishes dopaminergic neurons from other catecholaminergic neurons in the developing zebrafish embryo," *Mechanisms of Development*, vol. 101, pp. 237-243 (2001).
Kitada, Kazuhiro et al.; "Truncation of LIM homeobox transcription factor Lmx1a results in abnormal development of the central nervous system of qc/qc rat," *The 15th International Mouse Genome Conference, International Mammalian Genome Society* (Abstract) (2001).
Kitada, Kazuhiro and Tadao Serikawa; "Identification of the Causative Gene in eh Tremor Rat by Positional Cloning," *Proceedings of the 17th Annual Meeting of the Japanese Society of Animal Models for Human Diseases,*; pp. 6-10 (2001).
Kitada, Kazuhiro et al.; "Mutation of the LIM Homeobox gene Lmx1a causes abnormal development of the central nervous system in the queue courte rat," *Physiological Genomics & Rat Models*, Cold Spring Harbor Laboratory, New York, USA (Dec. 6-9, 2001).
Kruger, M. et al.; "The homeobox containing gene Lbx1 is required for correct dorsal-ventral patterning of the neural tube," *J. Neurochem.*, vol. 82(4), pp. 774-782 (2002).
Mazumder, et al., "Translational control by the 3-UTR: the ends specify the means," *Trends in Biochemical Sciences*, vol. 28, pp. 91-98 (2003).
Millonig, James H. et al.; "The mouse Dreher gene Lmx1a controls formation of the roof plate in the vertebrate CNS," *Nature*, vol. 403, pp. 764-769 (Feb. 17, 2000).
Smidt, "A second independent pathway for development of mesencephalic dopaminergic neurons requires Lmx1b," *Nature Neuroscience*, vol. 3(4), pp. 337-341 (2000).
Thameem, F., et al., "Cloning, expression and genomic structure of human LMX1A, and variant screening in Pima Indians," *Gene*, vol. 290, pp. 217-225 (2002).
R.H.J. Schlegel, Dictionary of Plant Breeding, Second Edition, CRC Press, p. 191 (2009).
GenBank Accession No. AF226662 (Mar. 13, 2000).
GenBank Accession No. AF078166 (Jul. 30, 1998).
International Search Report issued for PCT/JP04/17574 dated Feb. 22, 2005.
Decision of Final Rejection issued for Chinese Patent Application No. 200480041020.8 dated Jul. 24, 2009.
Office Action issued for Chinese Patent Application No. 200480041020.8 dated Feb. 1, 2010.
Office Action issued for Chinese Patent Application No. 200480041020.8 dated Jul. 4, 2008.
Office Action Issued for Chinese Patent Application No. 200480041020.8 dated Mar. 9, 2011.
Office Communication issued for European Patent Application No. 04819438.5 dated Feb. 7, 2008.
Office Communication for European Patent Application No. 04819438.5 dated Sep. 16, 2008.
Search Report issued for European Patent Application No. 04819438.5 dated Aug. 30, 2007.
Written Opinion issued for Singapore Patent Application No. 200603436-7 dated Oct. 22, 2007.
Advisory Action issued in U.S. Appl. No. 10/580,989, dated May 27, 2010, 3 pages.
Failli et al., "Expression of the LIM-homeodomain gene *Lmxla* (*dreher*) during development of the mouse nervous system," *Mechanisms of Development*, 2002, 118:225-228.
Final Office Action issued in U.S. Appl. No. 10/580,989, dated Mar. 23, 2010, 12 pages.
International Preliminary Report on Patentability issued in PCT App. Ser. No. PCT/JP2004/017574, dated Jul. 27, 2006, 4 pages.
Non-final Office Action issued in U.S. Appl. No. 10/580,989, dated Oct. 9, 2009, 24 pages.
Notice of Allowance issued in U.S. Appl. No. 10/580,989, dated Sep. 24, 2010, 7 pages.
Notice of Allowance issued in U.S. Appl. No. 10/580,989, dated Jan. 13, 2011, 5 pages.
Notice of Allowance issued in U.S. Appl. No. 10/580,989, dated Oct. 4, 2011, 6 pages.
Notice of Allowance issued in U.S. Appl. No. 10/580,989, dated Feb. 6, 2012, 7 pages.
Office Action issued in CN App. Ser. No. 200480041020.8, dated Feb. 12, 2010, 8 pages (with English translation).
Office Communication issued in EP Ser. App. No. 04819438.5, dated Jun. 13, 2008, 2 pages.
Office Communication issued in EP App. Ser. No. 04819438.5, dated Sep. 22, 2008, 2 pages.
Request for Continued Examination filed in U.S. Appl. No. 10/580,989, filed Feb. 8, 2011, 1 page.
Request for Continued Examination filed in U.S. Appl. No. 10/580,989, filed Dec. 27, 2011, 1 page.
Request for Examination and Amended Claims filed in CN App. Ser. No. 200480041020.8, filed Nov. 9, 2009, 13 pages (with English translation).
Response and Request for Continued Examination filed in U.S. Appl. No. 10/580,989, filed Dec. 17, 2010, 7 pages.
Response and Request for Continued Examination filed in U.S. Appl. No. 10/580,989, filed Jun. 10, 2010, 11 pages.
Response filed in CN App. Ser. No. 200480041020.8, filed May 24, 2011, 10 pages (with English translation).
Response filed in CN App. Ser. No. 200480041020.8, filed May 27, 2010, 20 pages (with English translation).
Response filed in CN App. Ser. No. 200480041020.8, filed Sep. 28, 2008, 15 pages (with English translation).
Response filed in EP App. Ser. No. 04819438.5, filed Jun. 23, 2008, 7 pages.
Response filed in EP App. Ser. No. 04819438.5, filed May 16, 2008, 35 pages.
Response filed in EP App. Ser. No. 04819438.5, filed Oct. 7, 2008, 14 pages.
Response filed in SG App. Ser. No. 200603436-7, filed Mar. 19, 2008, 11 pages.
Response filed in U.S. Appl. No. 10/580,989, filed Jan. 6, 2010, 9 pages.
Response filed in U.S. Appl. No. 10/580,989, filed Jun. 29, 2009, 6 pages.
Response filed in U.S. Appl. No. 10/580,989, filed May 18, 2010, 10 pages.
Response filed in U.S. Appl. No. 10/580,989, filed May 25, 2010, 6 pages.
Restriction Requirement issued in U.S. Appl. No. 10/580,989, issued May 29, 2009, 4 pages.

\* cited by examiner

Lmx1a    DAT

SN: SUBSTANTIA NIGRA  Pu: PUTAMEN
CC: CEREBRAL CORTEX  Ce: CEREBELLUM
Hi: HIPPOCAMPUS  MO: MEDULLA OBLONGATA
CN: CAUDATE NUCLEUS  Po: PONS

SEQUENCE LISTING

```
<160> NUMBER OF SEQ ID NOS: 46

<210> SEQ ID NO 1
<211> LENGTH: 26
<212> TYPE: DNA
<213> ORGANISM: Artificial Sequence
<220> FEATURE:
<223> OTHER INFORMATION: synthetic oligonucleotide primer ad2S for cDNA
      PCR amplification

<400> SEQUENCE: 1
cagctccaca acctacatca ttccgt                                          26

<210> SEQ ID NO 2
<211> LENGTH: 12
<212> TYPE: DNA
<213> ORGANISM: Artificial Sequence
<220> FEATURE:
<223> OTHER INFORMATION: synthetic oligonucleotide primer ad2A for cDNA
      PCR amplification

<400> SEQUENCE: 2
acggaatgat gt                                                         12

<210> SEQ ID NO 3
<211> LENGTH: 26
<212> TYPE: DNA
<213> ORGANISM: Artificial Sequence
<220> FEATURE:
<223> OTHER INFORMATION: synthetic oligonucleotide primer ad3S for cDNA
      PCR amplification

<400> SEQUENCE: 3
gtccatcttc tctctgagac tctggt                                          26

<210> SEQ ID NO 4
<211> LENGTH: 12
<212> TYPE: DNA
<213> ORGANISM: Artificial Sequence
<220> FEATURE:
<223> OTHER INFORMATION: synthetic oligonucleotide primer ad3A for cDNA
      PCR amplification

<400> SEQUENCE: 4
accagagtct ca                                                         12

<210> SEQ ID NO 5
<211> LENGTH: 26
<212> TYPE: DNA
<213> ORGANISM: Artificial Sequence
```

-continued

```
<220> FEATURE:
<223> OTHER INFORMATION: synthetic oligonucleotide primer ad4S for cDNA
      PCR amplification

<400> SEQUENCE: 5
ctgatgggtg tcttctgtga gtgtgt                                          26

<210> SEQ ID NO 6
<211> LENGTH: 12
<212> TYPE: DNA
<213> ORGANISM: Artificial Sequence
<220> FEATURE:
<223> OTHER INFORMATION: synthetic oligonucleotide primer ad4A for cDNA
      PCR amplification

<400> SEQUENCE: 6
acacactcac ag                                                         12

<210> SEQ ID NO 7
<211> LENGTH: 26
<212> TYPE: DNA
<213> ORGANISM: Artificial Sequence
<220> FEATURE:
<223> OTHER INFORMATION: synthetic oligonucleotide primer ad5S for cDNA
      PCR amplification

<400> SEQUENCE: 7
ccagcatcga gaatcagtgt gacagt                                          26

<210> SEQ ID NO 8
<211> LENGTH: 12
<212> TYPE: DNA
<213> ORGANISM: Artificial Sequence
<220> FEATURE:
<223> OTHER INFORMATION: synthetic oligonucleotide primer ad5A for cDNA
      PCR amplification

<400> SEQUENCE: 8
actgtcacac tg                                                         12

<210> SEQ ID NO 9
<211> LENGTH: 26
<212> TYPE: DNA
<213> ORGANISM: Artificial Sequence
<220> FEATURE:
<223> OTHER INFORMATION: synthetic oligonucleotide primer ad13S for cDNA
      PCR amplification

<400> SEQUENCE: 9
gtcgatgaac ttcgactgtc gatcgt                                          26

<210> SEQ ID NO 10
<211> LENGTH: 12
<212> TYPE: DNA
<213> ORGANISM: Artificial Sequence
<220> FEATURE:
<223> OTHER INFORMATION: synthetic oligonucleotide primer ad13A for cDNA
      PCR amplification

<400> SEQUENCE: 10
acgatcgaca gt                                                         12

<210> SEQ ID NO 11
<211> LENGTH: 26
<212> TYPE: DNA
<213> ORGANISM: Artificial Sequence
<220> FEATURE:
<223> OTHER INFORMATION: synthetic primer Human Lmx1a for cDNA RT-PCR
``` amplification

<400> SEQUENCE: 11
tgaagaaagt ctctgcaagt cagccc                                  26

<210> SEQ ID NO 12
<211> LENGTH: 26
<212> TYPE: DNA
<213> ORGANISM: Artificial Sequence
<220> FEATURE:
<223> OTHER INFORMATION: synthetic primer Human Lmx1a for cDNA RT-PCR
      amplification

<400> SEQUENCE: 12
caccaccgtt tgtctgagca gagctc                                  26

<210> SEQ ID NO 13
<211> LENGTH: 3338
<212> TYPE: DNA
<213> ORGANISM: Mus musculus
<220> FEATURE:
<223> OTHER INFORMATION: Lmx1a

<400> SEQUENCE: 13
gagagccgtc gcgagcagtt cacgggggct cttctctctc ctcccacctt acatttccct    60
tgtctggact ctaccctcta ggctcattct tgtcgccctg acactgctt ctgtcctgtc    120 ccaggagagt ggcaactgag ggtgcggagt cccaacaggc acgggaagct agactcaacc   180
gttcctccgc tctacaggtc ctcctggctc accccgaaca tgttggacgg cctgaagatg   240
gaggagaact ttcaaagtgc gattgagacc tcggcatctt tctcctcttt gctgggcaga   300
gcggtgagcc ccaagtctgt ctgcgagggc tgtcagcggg tcatctcgga caggtttctg   360
ctgcggctca acgacagctt ctggcacgag caatgcgtgc agtgtgcctc ctgcaaagag   420
cccctggaga ccacctgctt ctaccgggac aagaagctct actgcaagta ccactacgag   480
aaactgtttg ctgtcaaatg tgggggctgc ttcgaggcca ttgcgcccaa tgagtttgtc   540
atgcgtgccc agaagagcgt ataccactg agctgcttct gctgctgcgt ctgtgagcga   600
cagctgcaga agggtgacga gtttgtcctg aaggagggcc agctgctctg caaaggggac   660
tatgagaaag aacgggagct gctgagcctg gtgagccctg cggcctcaga ctcaggcaaa   720
agcgatgatg aggagagcct tgcaagtca gcccatgggg caggaaaagg agcatcagag   780
gacggcaagg accataagcg acccaaacgt cccagaacca tcctgaccac tcagcagagg   840
agagcattca aggcctcgtt tgaagtatcc tccaagccct gcagaaaggt gagggagact   900
ctggctgcgg agacagggct gagtgtccgt gtggttcagg tgtggttcca gaaccagcga   960
gccaagatga agaagctggc ccggcgacag cagcaacagc aacaggacca acagaacacc  1020
cagaggctga cttctgctca gacaaatggt agtgggaatg cggcatgga agggatcatg  1080 aaccccctata caacgttgcc caccccacag cagctgctgg ccattgaaca gagcgtctac  1140
aactctgatc ccttccgaca gggtctcacc ccaccccaga tgcctggaga tcacatgcac  1200
ccctatggtg ctgaacctct tttccatgac ttggatagtg atgacacatc tctcagtaac  1260
ctgggagact gcttcctggc aacctcagaa gctgggcccc tgcagtccag agtgggaaac  1320
cccattgacc atctgtactc catgcagaat tcctatttca cctcttgagt cttctcctac  1380
aattttgtga cctgggctcc catatggaac aaccatactg tgtgaagggt tgctgacttt  1440
aggatgggga ggccagagaa gaggtgggct ggggagggag gtttgttggg gatgctgttg  1500
tttaattata tggtgtagct cagcatttcc aaagactgaa tacattatgg attgcatagt  1560

-continued

```
ttaatgtttc taataagagt cttagtgtta gatatgaaga tgtgtttatc attaagggca    1620
gggtcttta  atatagacat tctcaagcaa actagatatc tagggactcc taacagcttc    1680
ccaccgttct ggagaagtgc ttgtcaagag gtgccgtatg tctattcatc tacacaccaa    1740
tagacagaca gatttgtgtg tgtgtgtgtg tgtgtgtgtg tgtgtgtgtg tgtatgagtg    1800
tgtgtaaaac ctttcatact ttatcatcaa agtttattcc taattataac agacaccaac    1860
tgtacagcaa aagtaacttt attttcagtg tgaactatat ttaaggaaat gcttgatgca    1920
cttaagttat aaaatgagat aatttacttt tataaacttt attttagtt  tggagagact    1980
catcggcagg gcagagagaa ctgttccacc gggcccaca  gctctgagtg cttgagttca    2040
ctctgtgatc agagcatcat tgaggtctag aatacaactc cagatggcag gcagcatgct    2100
atagtgaact catgctcacc ctggtgtcca gtcactgggc ctgaatgaga tttaggctt    2160
attggcatgg gattgttggg cagcatcagc aaggttgtcc ttaccccac  ccccaccccca   2220
gattcagcct cgatgagtgt ggatgaagtt gatagccaca cctacctctc tctctatgag    2280
tgtggatgag gtggttgcca cacctacctc cctggggaca ataaggctcc ataccaggac    2340
atgatcgaag ttgaaactaa aataaatctg atatgattta aaatataacc gagtcatgta    2400
cctgatgata gaggatacct gggaccacag agcaggaagt tctggtaccc taagtcctat    2460
ctctctgcat agcccatatg gccacatgac agagacacag ctctgagggg gtggagacta    2520
cgctccatct gagaaggtgg aagaggcgtg gtggatggaa ttctagaaca agtgttgact    2580
tgcacatctg ttgttttttt tttttgtttt gttttgtttt gttcttactt tttaaaagt    2640
cacttcaacg tgactgtatg cacccccaaa agccggaatt acttgtgatc tctgtttgtc    2700
tctttcttga gggcccataa tctgggggcc tgctcataaa cagcctcatg gagttcatag    2760
aagcagaggg gaccaggcag gtacccaggg ctcttccctc caactcatgt tgcagtccct    2820
gagcacagga agacccagta gccattgtac acagggacaa tcccgtgccc tgaactccat    2880
tgtatacagg gacagttcca tgccctgatc tccaattacg gtgctagagt gggatcttct    2940
gtgttaggat ccttctgggg aagcagaatg agtgtagggg gaagaaagaa gggctccagt    3000
gagaggggct gtgacaggca tgacgtcatg cccgggacca tcatcagagc catgactatg    3060
cccacatatc cacttcattc tctttaaggc cagaggaagc atgtccctta gtggtagagt    3120
gtgtgttgtg tgatttttgt gctcttcttt ataatttata caaaccgtca ggaaacctga    3180
accagtctgt gggctgagaa tgaggcgggt gtagggggca cagacagtgt ctgtgtggct    3240
gattggttga ggaatgtagc agatatgtga atgaaagcaa acagagatcc ttaattctac    3300
tctctaatga cataccgaga tgaaattaaa agcctctt                             3338
```

<210> SEQ ID NO 14
<211> LENGTH: 382
<212> TYPE: PRT
<213> ORGANISM: Mus musculus
<220> FEATURE:
<223> OTHER INFORMATION: Lmx1a
<400> SEQUENCE: 14

```
Met Leu Asp Gly Leu Lys Met Glu Glu Asn Phe Gln Ser Ala Ile Glu
 1               5                  10                  15

Thr Ser Ala Ser Phe Ser Ser Leu Leu Gly Arg Ala Val Ser Pro Lys
            20                  25                  30

Ser Val Cys Glu Gly Cys Gln Arg Val Ile Ser Asp Arg Phe Leu Leu
        35                  40                  45
```

-continued

```
Arg Leu Asn Asp Ser Phe Trp His Glu Gln Cys Val Gln Cys Ala Ser
 50                  55                  60

Cys Lys Glu Pro Leu Glu Thr Thr Cys Phe Tyr Arg Asp Lys Lys Leu
 65                  70                  75                  80

Tyr Cys Lys Tyr His Tyr Glu Lys Leu Phe Ala Val Lys Cys Gly Gly
                 85                  90                  95

Cys Phe Glu Ala Ile Ala Pro Asn Glu Phe Val Met Arg Ala Gln Lys
            100                 105                 110

Ser Val Tyr His Leu Ser Cys Phe Cys Cys Val Cys Glu Arg Gln
            115                 120                 125

Leu Gln Lys Gly Asp Glu Phe Val Leu Lys Glu Gly Gln Leu Leu Cys
130                 135                 140

Lys Gly Asp Tyr Glu Lys Glu Arg Glu Leu Leu Ser Leu Val Ser Pro
145                 150                 155                 160

Ala Ala Ser Asp Ser Gly Lys Ser Asp Asp Glu Glu Ser Leu Cys Lys
                165                 170                 175

Ser Ala His Gly Ala Gly Lys Gly Ala Ser Glu Asp Gly Lys Asp His
            180                 185                 190

Lys Arg Pro Lys Arg Pro Arg Thr Ile Leu Thr Thr Gln Gln Arg Arg
            195                 200                 205

Ala Phe Lys Ala Ser Phe Glu Val Ser Ser Lys Pro Cys Arg Lys Val
210                 215                 220

Arg Glu Thr Leu Ala Ala Glu Thr Gly Leu Ser Val Arg Val Val Gln
225                 230                 235                 240

Val Trp Phe Gln Asn Gln Arg Ala Lys Met Lys Lys Leu Ala Arg Arg
                245                 250                 255

Gln Gln Gln Gln Gln Asp Gln Gln Asn Thr Gln Arg Leu Thr Ser
            260                 265                 270

Ala Gln Thr Asn Gly Ser Gly Asn Ala Gly Met Glu Gly Ile Met Asn
            275                 280                 285

Pro Tyr Thr Thr Leu Pro Thr Pro Gln Gln Leu Leu Ala Ile Glu Gln
290                 295                 300

Ser Val Tyr Asn Ser Asp Pro Phe Arg Gln Gly Leu Thr Pro Pro Gln
305                 310                 315                 320

Met Pro Gly Asp His Met His Pro Tyr Gly Ala Glu Pro Leu Phe His
                325                 330                 335

Asp Leu Asp Ser Asp Asp Thr Ser Leu Ser Asn Leu Gly Asp Cys Phe
            340                 345                 350

Leu Ala Thr Ser Glu Ala Gly Pro Leu Gln Ser Arg Val Gly Asn Pro
            355                 360                 365

Ile Asp His Leu Tyr Ser Met Gln Asn Ser Tyr Phe Thr Ser
370                 375                 380
```

<210> SEQ ID NO 15
<211> LENGTH: 1562
<212> TYPE: DNA
<213> ORGANISM: Homo sapiens
<220> FEATURE:
<223> OTHER INFORMATION: Lmx1a

<400> SEQUENCE: 15

```
gtgaaatcag atcagccaga gcagttcgct gtgactgatc tctcctccca ccctacattc    60
tcttggctgg accctatcct cctggctgat tctggtcgcc ctggacactc cctcagttct   120
ttcccaggag tgcggtggct gctggcgccg agtcccagcg ggcacggacg tcagacgcat   180
cgtttcttct cctctacagg tcctcccggc ccggcccgaa catgctggac ggcctaaaga   240
```

-continued

```
tggaggagaa cttccaaagc gcgatcgaca cctcggcctc cttctcctcg ctgctgggca    300
gagcggtgag ccccaagtct gtctgcgagg gctgtcagcg ggtcatcttg acaggtttc     360 tgctgcggct caacgacagc ttctggcatg agcagtgcgt gcagtgcgcc tcctgcaaag    420
agcccctgga gaccacctgc ttctaccggg acaagaagct gtactgcaag tatgactacg    480
agaagctgtt tgctgttaaa tgtgggggct gcttcgaggc catcgctccc aatgagtttg    540
ttatgcgggc ccagaagagt gtataccacc tgagctgctt ctgctgctgt gtctgcgagc    600
gacagcttca gaaggtgatg agtttgtcc tgaaggaggg gcagctgctc tgcaaagggg     660
actatgagaa ggagcgggag ctgctcagcc tggtgagccc agcagcctca gactcaggta    720
aaagtgatga tgaagaaagt ctctgcaagt cagcccatgg ggcagggaaa ggaactgctg    780
aggaaggcaa ggaccataag cgccccaaac gtccgagaac catcttgaca actcaacaga    840
ggcgagcatt caaggcctca tttgaagtat cctccaagcc ctgcaggaag gtgagagaga    900
ctctggctgc agagacaggg ctgagtgtcc gtgtcgtcca ggtgtggttc caaaaccaga    960
gagcgaagat gaagaagctg gccaggcgac agcagcagca gcagcaagat cagcagaaca    1020
cccagaggct gagctctgct cagacaaacg gtggtgggag tgctgggatg gaaggaatca    1080
tgaaccccta cacggctctg cccaccccac agcagctcct ggccatcgag cagagtgtct    1140
acagctcaga tccttccga cagggtctca ccccacccca gatgcctgga gaccacatgc     1200
acccttatgg tgccgagccc ctttccatg acctggatag cgacgacacc tccctcagta     1260
acctgggtga ttgtttccta gcaacctcag aagctgggcc tctgcagtcc agagtgggaa    1320
accccattga ccatctgtac tccatgcaga attcttactt cacatcttga gtcttcccct    1380
agagttctgt gactaggctc ccatatggaa caaccatatt ctttgagggg tcactggctt    1440
taggacaggg aggccaggga agaggtgggt tggggaggga gttttgttgg ggatgctgtt    1500
gtataatgat atggtgtagc tcagcatttc caaagactga atacattatg gattgcatag    1560
tt                                                                   1562
```

<210> SEQ ID NO 16
<211> LENGTH: 382
<212> TYPE: PRT
<213> ORGANISM: Homo sapiens
<220> FEATURE:
<223> OTHER INFORMATION: Lmx1a

<400> SEQUENCE: 16

```
Met Leu Asp Gly Leu Lys Met Glu Glu Asn Phe Gln Ser Ala Ile Asp
 1               5                  10                  15

Thr Ser Ala Ser Phe Ser Ser Leu Leu Gly Arg Ala Val Ser Pro Lys
            20                  25                  30

Ser Val Cys Glu Gly Cys Gln Arg Val Ile Leu Asp Arg Phe Leu Leu
        35                  40                  45

Arg Leu Asn Asp Ser Phe Trp His Glu Gln Cys Val Gln Cys Ala Ser
    50                  55                  60

Cys Lys Glu Pro Leu Glu Thr Thr Cys Phe Tyr Arg Asp Lys Lys Leu
65                  70                  75                  80

Tyr Cys Lys Tyr Asp Tyr Glu Lys Leu Phe Ala Val Lys Cys Gly Gly
                85                  90                  95

Cys Phe Glu Ala Ile Ala Pro Asn Glu Phe Val Met Arg Ala Gln Lys
            100                 105                 110

Ser Val Tyr His Leu Ser Cys Phe Cys Cys Val Cys Glu Arg Gln
        115                 120                 125
```

```
Leu Gln Lys Gly Asp Glu Phe Val Leu Lys Glu Gly Gln Leu Leu Cys
    130                 135                 140
Lys Gly Asp Tyr Glu Lys Glu Arg Glu Leu Leu Ser Leu Val Ser Pro
145                 150                 155                 160
Ala Ala Ser Asp Ser Gly Lys Ser Asp Asp Glu Glu Ser Leu Cys Lys
                165                 170                 175
Ser Ala His Gly Ala Gly Lys Gly Thr Ala Glu Glu Gly Lys Asp His
            180                 185                 190
Lys Arg Pro Lys Arg Pro Arg Thr Ile Leu Thr Thr Gln Gln Arg Arg
        195                 200                 205
Ala Phe Lys Ala Ser Phe Glu Val Ser Ser Lys Pro Cys Arg Lys Val
    210                 215                 220
Arg Glu Thr Leu Ala Ala Glu Thr Gly Leu Ser Val Arg Val Val Gln
225                 230                 235                 240
Val Trp Phe Gln Asn Gln Arg Ala Lys Met Lys Lys Leu Ala Arg Arg
                245                 250                 255
Gln Gln Gln Gln Gln Gln Asp Gln Gln Asn Thr Gln Arg Leu Ser Ser
            260                 265                 270
Ala Gln Thr Asn Gly Gly Gly Ser Ala Gly Met Glu Gly Ile Met Asn
        275                 280                 285
Pro Tyr Thr Ala Leu Pro Thr Pro Gln Gln Leu Leu Ala Ile Glu Gln
    290                 295                 300
Ser Val Tyr Ser Ser Asp Pro Phe Arg Gln Gly Leu Thr Pro Pro Gln
305                 310                 315                 320
Met Pro Gly Asp His Met His Pro Tyr Gly Ala Glu Pro Leu Phe His
                325                 330                 335
Asp Leu Asp Ser Asp Thr Ser Leu Ser Asn Leu Gly Asp Cys Phe
            340                 345                 350
Leu Ala Thr Ser Glu Ala Gly Pro Leu Gln Ser Arg Val Gly Asn Pro
        355                 360                 365
Ile Asp His Leu Tyr Ser Met Gln Asn Ser Tyr Phe Thr Ser
    370                 375                 380

<210> SEQ ID NO 17
<211> LENGTH: 839
<212> TYPE: DNA
<213> ORGANISM: Homo sapiens
<220> FEATURE:
<223> OTHER INFORMATION: Lmx1a

<400> SEQUENCE: 17
tctggctttt tccacttggt gtggtggttt gggattcat tcattcctat ttcagcattc      60
cactgtatag tccagaggtg agcaaggcaa ggctggtggg tggctctgtt atccatctcc     120
tgtgtccaag cgactgctcc agttgtcacc atgtttccag tcaccaggtg agagagactc     180
tggctgcaga gacagggctg agtgtccgtg tcgtccaggt gtggttccaa aaccagagag     240
cgaagatgaa gaagctggcc aggcgacagc agcagcagca gcaagatcag cagaacaccc     300
agaggctgag ctctgctcag acaaacggtg gtgggagtgc tgggatggaa ggaatcatga     360 accccctacac ggctctgccc accccacagc agctcctggc catcgagcag agtgtctaca     420
gctcagatcc cttccgacag gtctcaccc accccagat gctggagac cacatgcacc       480 cttatggtgc cgagcccctt ttccatgacc tggatagcga cgacacctcc ctcagtaacc     540
tgggtgattg tttcctagca acctcagaag ctgggcctct gcagtccaga gtgggaaacc     600
ccattgacca tctgtactcc atgcagaatt cttacttcac atcttgagtc ttcccctaga     660
```

```
gttctgtgac taggctccca tatggaacaa ccatattctt tgaggggtca ctggctttag    720
gacagggagg ccagggaaga ggtgggttgg ggagggagtt ttgttgggga tgctgttgta    780
taatgatatg gtgtagctca gcatttccaa agactgaata cattatggat tgcatagtt    839
```

<210> SEQ ID NO 18
<211> LENGTH: 133
<212> TYPE: PRT
<213> ORGANISM: Homo sapiens
<220> FEATURE:
<223> OTHER INFORMATION: Lmx1a

<400> SEQUENCE: 18

```
Met Lys Lys Leu Ala Arg Arg Gln Gln Gln Gln Gln Asp Gln Gln
1               5                   10                  15

Asn Thr Gln Arg Leu Ser Ser Ala Gln Thr Asn Gly Gly Ser Ala
            20                  25                  30

Gly Met Glu Gly Ile Met Asn Pro Tyr Thr Ala Leu Pro Thr Pro Gln
        35                  40                  45

Gln Leu Leu Ala Ile Glu Gln Ser Val Tyr Ser Ser Asp Pro Phe Arg
    50                  55                  60

Gln Gly Leu Thr Pro Pro Gln Met Pro Gly Asp His Met His Pro Tyr
65                  70                  75                  80

Gly Ala Glu Pro Leu Phe His Asp Leu Asp Ser Asp Thr Ser Leu
                85                  90                  95

Ser Asn Leu Gly Asp Cys Phe Leu Ala Thr Ser Glu Ala Gly Pro Leu
            100                 105                 110

Gln Ser Arg Val Gly Asn Pro Ile Asp His Leu Tyr Ser Met Gln Asn
        115                 120                 125

Ser Tyr Phe Thr Ser
    130
```

<210> SEQ ID NO 19
<211> LENGTH: 1119
<212> TYPE: DNA
<213> ORGANISM: Mus musculus
<220> FEATURE:
<223> OTHER INFORMATION: Lmx1b

<400> SEQUENCE: 19

```
atgttggacg gcatcaagat ggaggagcac gcccttcgcc ccgggcccgc caccctgggg    60
gtgctgctgg gctccgactg cccgcatccc gccgtctgcg agggctgcca gcggcccatc    120
tccgaccgct tcctgatgcg agtcaacgag tcgtcctggc acgaggagtg tttgcagtgc    180
gcggcatgtc agcaagccct caccaccagc tgctacttcc gggatcggaa actgtactgc    240
aaacaagact accaacagct cttcgcggca aagtgcagcg gctgcatgga agatcgcg    300 cctaccgagt tcgtcatgcg ggcgctggag tgtgtgtacc acttgggctg ttctgctgc    360 tgtgtgtgcg agaggcaact gcgcaagggg gacgagttcg tgctcaagga gggccagctg    420
ctgtgcaagg gtgactatga aggagaaaa gacctgctca gctccgtgag cccgacgag    480 tctgactctg tgaagagtga ggatgaagat ggagacatga gccggccaa ggggcagggc    540 agccagagta aaggcagtgg agatgacggg aaagacccga aaggcccaa acggccccga    600 accatcctca ccacacagca gcgaagagct ttcaaggcat cctttgaggt ctcctccaag    660
ccctgtcgga aggtccgaga gacattggca gcagagacag gcctcagcgt gcgtgtggtc    720
caggtctggt ttcagaacca aagagcaaag atgaagaagc tggcccggag acaccagcaa    780
```

-continued

```
cagcaggagc agcagaactc ccagcggctg ggccaagagg ttctgtcaag ccgcatggag    840
ggcatgatgg cctcctacac cgcgctggcc cctccgcagc agcagatcgt ggccatggag    900
cagagcccct acggaagcag cgaccccttc aacagggcc tcacgccgcc caaatgcca    960 gggaacgact ccatcttcca cgatattgat agtgatacct ccctcaccag cctcagcgac    1020
tgcttcctcg gctcttccga cgtgggctcc ctgcaggcgc gcgtggggaa ccccattgac    1080
cggctctact ccatgcagag ctcctacttt gcctcctga                           1119
```

<210> SEQ ID NO 20
<211> LENGTH: 372
<212> TYPE: PRT
<213> ORGANISM: Mus musculus
<220> FEATURE:
<223> OTHER INFORMATION: Lmx1b

<400> SEQUENCE: 20

```
Met Leu Asp Gly Ile Lys Met Glu Glu His Ala Leu Arg Pro Gly Pro
1               5                   10                  15

Ala Thr Leu Gly Val Leu Leu Gly Ser Asp Cys Pro His Pro Ala Val
            20                  25                  30

Cys Glu Gly Cys Gln Arg Pro Ile Ser Asp Arg Phe Leu Met Arg Val
        35                  40                  45

Asn Glu Ser Ser Trp His Glu Glu Cys Leu Gln Cys Ala Ala Cys Gln
    50                  55                  60

Gln Ala Leu Thr Thr Ser Cys Tyr Phe Arg Asp Arg Lys Leu Tyr Cys
65                  70                  75                  80

Lys Gln Asp Tyr Gln Gln Leu Phe Ala Ala Lys Cys Ser Gly Cys Met
                85                  90                  95

Glu Lys Ile Ala Pro Thr Glu Phe Val Met Arg Ala Leu Glu Cys Val
            100                 105                 110

Tyr His Leu Gly Cys Phe Cys Cys Val Cys Glu Arg Gln Leu Arg
        115                 120                 125

Lys Gly Asp Glu Phe Val Leu Lys Glu Gly Gln Leu Leu Cys Lys Gly
    130                 135                 140

Asp Tyr Glu Lys Glu Lys Asp Leu Leu Ser Ser Val Ser Pro Asp Glu
145                 150                 155                 160

Ser Asp Ser Val Lys Ser Glu Asp Glu Asp Gly Asp Met Lys Pro Ala
                165                 170                 175

Lys Gly Gln Gly Ser Gln Ser Lys Gly Ser Gly Asp Asp Gly Lys Asp
            180                 185                 190

Pro Arg Arg Pro Lys Arg Pro Arg Thr Ile Leu Thr Thr Gln Gln Arg
        195                 200                 205

Arg Ala Phe Lys Ala Ser Phe Glu Val Ser Ser Lys Pro Cys Arg Lys
    210                 215                 220

Val Arg Glu Thr Leu Ala Ala Glu Thr Gly Leu Ser Val Arg Val Val
225                 230                 235                 240

Gln Val Trp Phe Gln Asn Gln Arg Ala Lys Met Lys Lys Leu Ala Arg
                245                 250                 255

Arg His Gln Gln Gln Gln Gln Gln Asn Ser Gln Arg Leu Gly Gln
            260                 265                 270

Glu Val Leu Ser Ser Arg Met Glu Gly Met Met Ala Ser Tyr Thr Ala
        275                 280                 285

Leu Ala Pro Pro Gln Gln Ile Val Ala Met Glu Gln Ser Pro Tyr
    290                 295                 300

Gly Ser Ser Asp Pro Phe Gln Gln Gly Leu Thr Pro Pro Gln Met Pro
```

```
305                 310                 315                 320
Gly Asn Asp Ser Ile Phe His Asp Ile Asp Ser Asp Thr Ser Leu Thr
                325                 330                 335

Ser Leu Ser Asp Cys Phe Leu Gly Ser Ser Asp Val Gly Ser Leu Gln
                340                 345                 350

Ala Arg Val Gly Asn Pro Ile Asp Arg Leu Tyr Ser Met Gln Ser Ser
                355                 360                 365

Tyr Phe Ala Ser
        370

<210> SEQ ID NO 21
<211> LENGTH: 1119
<212> TYPE: DNA
<213> ORGANISM: Homo sapiens
<220> FEATURE:
<223> OTHER INFORMATION: Lmx1b

<400> SEQUENCE: 21
atgttggacg gcatcaagat ggaggagcac gccctgcgcc cgggcccgc cactctgggg      60 gtgctgctgg gctccgactg cccgcatccc gccgtctgcg agggctgcca gcggcccatc    120
tccgaccgct tcctgatgcg agtcaacgag tcgtcctggc acgaggagtg tttgcagtgc    180
gcggcgtgtc agcaagccct caccaccagc tgctacttcc gggatcggaa actgtactgc    240
aaacaagact accaacagct cttcgcggcc aagtgcagcg gctgcatgga agagatcgcc    300
cccaccgagt tcgtgatgcg ggcgctggag tgcgtgtacc acctgggctg cttctgctgc    360
tgcgtgtgtg aacggcagct acgcaagggc gacgaattcg tgctcaagga gggccagctg    420
ctgtgcaagg gtgactacga aggagaag accctgctca gctccgtgag ccccgacgag    480
tccgactccg tgaagagcga ggatgaagat ggggacatga gccggccaa ggggcagggc    540 agtcagagca gggcagcgg ggatgacggg aaggacccgc ggaggccaa gcgaccccgg    600 accatcctca ccacgcagca gcgaagagcc ttcaaggcct ccttcgaggt ctcgtcgaag    660
ccttgccgaa aggtccgaga gacactggca gctgagacgg gcctcagtgt gcgcgtggtc    720
caggtctggt ttcagaacca aagagcaaag atgaagaagc tggcgcggcg gcaccagcag    780
cagcaggagc agcagaactc ccagcggctg gccaggagg tcctgtccag ccgcatggag    840
ggcatgatgg cttcctacac gccgctggcc ccaccacagc agcagatcgt ggccatggaa    900
cagagcccct acggcagcag cgacccttc cagcagggcc tcacgccgcc caaatgcca    960 gggaacgact ccatcttcca tgacatcgac agcgatacct ccttaaccag cctcagcgac   1020
tgcttcctcg gctcctcaga cgtgggctcc ctgcaggccc gcgtggggaa ccccatcgac   1080
cggctctact ccatgcagag ttcctacttc gcctcctga                          1119

<210> SEQ ID NO 22
<211> LENGTH: 372
<212> TYPE: PRT
<213> ORGANISM: Homo sapiens
<220> FEATURE:
<223> OTHER INFORMATION: Lmx1b

<400> SEQUENCE: 22

Met Leu Asp Gly Ile Lys Met Glu Glu His Ala Leu Arg Pro Gly Pro
 1               5                  10                  15

Ala Thr Leu Gly Val Leu Leu Gly Ser Asp Cys Pro His Pro Ala Val
             20                  25                  30

Cys Glu Gly Cys Gln Arg Pro Ile Ser Asp Arg Phe Leu Met Arg Val
         35                  40                  45
```

Asn Glu Ser Ser Trp His Glu Glu Cys Leu Gln Cys Ala Ala Cys Gln
 50                  55                  60

Gln Ala Leu Thr Thr Ser Cys Tyr Phe Arg Asp Arg Lys Leu Tyr Cys
65                  70                  75                  80

Lys Gln Asp Tyr Gln Gln Leu Phe Ala Ala Lys Cys Ser Gly Cys Met
                85                  90                  95

Glu Lys Ile Ala Pro Thr Glu Phe Val Met Arg Ala Leu Glu Cys Val
            100                 105                 110

Tyr His Leu Gly Cys Phe Cys Cys Val Cys Glu Arg Gln Leu Arg
        115                 120                 125

Lys Gly Asp Glu Phe Val Leu Lys Glu Gly Gln Leu Leu Cys Lys Gly
    130                 135                 140

Asp Tyr Glu Lys Glu Lys Asp Leu Leu Ser Val Ser Pro Asp Glu
145                 150                 155                 160

Ser Asp Ser Val Lys Ser Glu Asp Glu Asp Gly Asp Met Lys Pro Ala
                165                 170                 175

Lys Gly Gln Gly Ser Gln Ser Lys Gly Ser Gly Asp Asp Gly Lys Asp
            180                 185                 190

Pro Arg Arg Pro Lys Arg Pro Thr Ile Leu Thr Thr Gln Gln Arg
        195                 200                 205

Arg Ala Phe Lys Ala Ser Phe Glu Val Ser Ser Lys Pro Cys Arg Lys
    210                 215                 220

Val Arg Glu Thr Leu Ala Ala Glu Thr Gly Leu Ser Val Arg Val Val
225                 230                 235                 240

Gln Val Trp Phe Gln Asn Gln Arg Ala Lys Met Lys Lys Leu Ala Arg
                245                 250                 255

Arg His Gln Gln Gln Leu Glu Gln Asn Ser Gln Arg Leu Gly Gln
            260                 265                 270

Glu Val Leu Ser Ser Arg Met Glu Gly Met Met Ala Ser Tyr Thr Pro
        275                 280                 285

Leu Ala Pro Pro Gln Gln Gln Ile Val Ala Met Glu Gln Ser Pro Tyr
    290                 295                 300

Gly Ser Ser Asp Pro Phe Gln Gln Gly Leu Thr Pro Pro Gln Met Pro
305                 310                 315                 320

Gly Asn Asp Ser Ile Phe His Asp Ile Asp Ser Asp Thr Ser Leu Thr
                325                 330                 335

Ser Leu Ser Asp Cys Phe Leu Gly Ser Ser Asp Val Gly Ser Leu Gln
            340                 345                 350

Ala Arg Val Gly Asn Pro Ile Asp Arg Leu Tyr Ser Met Gln Ser Ser
        355                 360                 365

Tyr Phe Ala Ser
    370

<210> SEQ ID NO 23
<211> LENGTH: 2247
<212> TYPE: DNA
<213> ORGANISM: Mus musculus
<220> FEATURE:
<223> OTHER INFORMATION: Nurr1

<400> SEQUENCE: 23
ggcacgaggg ccagggccag tccgccccgc ggctccgcac agctccgcgt ccctctctcc    60
ggccccgctg gctgcctccc tctcctgcgg ccgggctggc tgcgtgtggc tctccgcgcc   120
ccgcttccgc agcgctcccg cggacccggg ctcctctgct cccggaggga actgcacttc   180

| | |
|---|---|
| ggcggagttg aatgaatgaa gagagcggac aaggagatct gacgggctgg attcccaata | 240 |
| gctctttttt aaaatcttgg aaactttgtc cttcgctgaa ttacgacact gtccaccttt | 300 |
| aatttcctcg aaaactccaa taactctgct gaagccatgc cttgtgttca ggcgcagtat | 360 |
| gggtcctcgc ctcaaggagc cagccccgct tctcagagct acagttacca ctcttcggga | 420 |
| gaatacagct ccgatttctt aactccagag tttgtcaagt ttagcatgga cctcaccaac | 480 |
| actgaaatta ctgccaccac ttctctcccc agcttcagta cctttatgga caactacagc | 540 |
| acaggctacg acgtcaagcc accttgcttg taccaaatgc ccctgtccgg acagcagtcc | 600 |
| tccattaagg tagaagacat tcagatgcac aactaccagc aacacagcca cctgcccccct | 660 |
| cagtccgagg agatgatgcc acacagcggg tcggtttact acaagccctc ttcgcccccg | 720 |
| acacccagca ccccgagctt ccaggtgcag catagcccga tgtgggacga tccgggctcc | 780 |
| cttcacaact tccaccagaa ctacgtggcc actacgcata tgatcgagca gaggaagaca | 840 |
| cctgtctccc gcctgtcact cttctccttt aagcagtcgc ccccgggcac tcctgtgtct | 900 |
| agctgccaga tgcgcttcga cgggcctctg cacgtcccca tgaacccgga gcccgcgggc | 960 |
| agccaccacg tagtggatgg gcagaccttc gccgtgccca cccccattcg caagccggca | 1020 |
| tccatgggct tcccgggcct gcagatcggc cacgcatcgc agttgcttga cacgcaggtg | 1080 |
| ccctcgccgc cgtcccgggg ctctcccctcc aatgagggtc tgtgcgctgt ttgcggtgac | 1140 |
| aacgcggcct gtcagcacta cggtgttcgc acttgtgagg gctgcaaagg tttctttaag | 1200 |
| cgcacggtgc aaaaaaacgc gaaatatgtg tgtttagcaa ataaaaactg cccagtggac | 1260 |
| aagcgccgcc gaaatcgttg tcagtactgt cggtttcaga agtgcctagc tgttgggatg | 1320 |
| gttaaagaag tggttcgcac ggacagttta aaaggccgga gaggtcgttt accctcgaag | 1380 |
| ccgaagagcc cacaggatcc ctctccccccc tcacctccgg tgagtctgat cagtgccctc | 1440 |
| gtcagagccc acgtcgattc caatccggca atgaccagcc tggactattc caggttccag | 1500 |
| gcaaaccctg actatcagat gagtggagat gatacccaac atatccagca gttctacgat | 1560 |
| ctcctgaccg gctctatgga gatcatcaga gggtgggcag agaagatccc tggctttgct | 1620 |
| gacctgccca agccgaccca ggacctgctt tttgaatcag ctttcttaga attatttgtt | 1680 |
| ctgcgcttag catacaggtc caacccagtg gagggtaaac tcatcttttg caatggggtg | 1740 |
| gtcttgcaca ggttgcaatg cgtgcgtggc tttggggaat ggattgattc cattgttgaa | 1800 |
| ttctcctcca acttgcagaa tatgaacatc gacatttctg ccttctcctg cattgctgcc | 1860 |
| ctggctatgg tcacagagag acacgggctc aaggaaccca gagagtgga agagctacaa | 1920 |
| aacaaaattg taaattgtct taaagaccat gtgactttca ataatggggg tttgaaccga | 1980 |
| cccaactacc tgtctaaact gttggggaag ctgccagaac tccgcaccct ttgcacacag | 2040 |
| ggcctccagc gcattttcta cctgaaattg gaagacttgg taccaccacc agcaataatt | 2100 |
| gacaaacttt tcctggacac cttaccttc taagaccttc tcccaagcac gtcaaagaac | 2160 |
| tggaaagaaa aaaaaaataa catccagagg gggctggtca catgggcaga gagctggttg | 2220 |
| aagtgtccag ttcaccttat ctcccctt | 2247 |

<210> SEQ ID NO 24
<211> LENGTH: 598
<212> TYPE: PRT
<213> ORGANISM: Mus musculus
<220> FEATURE:
<223> OTHER INFORMATION: Nurr1

<400> SEQUENCE: 24

```
Met Pro Cys Val Gln Ala Gln Tyr Gly Ser Ser Pro Gln Gly Ala Ser
1               5                   10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
            35                  40                  45

Thr Glu Ile Thr Ala Thr Thr Ser Leu Pro Ser Phe Ser Thr Phe Met
            50                  55                  60

Asp Asn Tyr Ser Thr Gly Tyr Asp Val Lys Pro Pro Cys Leu Tyr Gln
65                      70                  75                  80

Met Pro Leu Ser Gly Gln Gln Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
            115                 120                 125

Thr Pro Ser Thr Pro Ser Phe Gln Val Gln His Ser Pro Met Trp Asp
            130                 135                 140

Asp Pro Gly Ser Leu His Asn Phe His Gln Asn Tyr Val Ala Thr Thr
145                 150                 155                 160

His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
            195                 200                 205

Ser His His Val Val Asp Gly Gln Thr Phe Ala Val Pro Asn Pro Ile
210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
            275                 280                 285

Arg Thr Val Gln Lys Asn Ala Lys Tyr Val Cys Leu Ala Asn Lys Asn
            290                 295                 300

Cys Pro Val Asp Lys Arg Arg Arg Asn Arg Cys Gln Tyr Cys Arg Phe
305                 310                 315                 320

Gln Lys Cys Leu Ala Val Gly Met Val Lys Glu Val Val Arg Thr Asp
            325                 330                 335

Ser Leu Lys Gly Arg Arg Gly Arg Leu Pro Ser Lys Pro Lys Ser Pro
            340                 345                 350

Gln Asp Pro Ser Pro Ser Pro Pro Val Ser Leu Ile Ser Ala Leu
            355                 360                 365

Val Arg Ala His Val Asp Ser Asn Pro Ala Met Thr Ser Leu Asp Tyr
            370                 375                 380

Ser Arg Phe Gln Ala Asn Pro Asp Tyr Gln Met Ser Gly Asp Asp Thr
385                 390                 395                 400

Gln His Ile Gln Gln Phe Tyr Asp Leu Leu Thr Gly Ser Met Glu Ile
            405                 410                 415

Ile Arg Gly Trp Ala Glu Lys Ile Pro Gly Phe Ala Asp Leu Pro Lys
            420                 425                 430
```

```
Ala Asp Gln Asp Leu Leu Phe Glu Ser Ala Phe Leu Glu Leu Phe Val
        435                 440                 445

Leu Arg Leu Ala Tyr Arg Ser Asn Pro Val Glu Gly Lys Leu Ile Phe
    450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
    530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ala Ile Ile Asp Lys Leu Phe
            580                 585                 590

Leu Asp Thr Leu Pro Phe
        595

<210> SEQ ID NO 25
<211> LENGTH: 3447
<212> TYPE: DNA
<213> ORGANISM: Homo sapiens
<220> FEATURE:
<223> OTHER INFORMATION: Nurr1

<400> SEQUENCE: 25
ggccagtccg cccggcggct cgcgcacggc tccgcggtcc cttttgcctg tccagccggc      60
cgcctgtccc tgctccctcc ctccgtgagg tgtccgggtt cccttcgccc agctctccca     120
cccctacccg accccggcgc ccgggctccc agagggaact gcacttcggc agagttgaat     180
gaatgaagag agacgcggag aactcctaag gaggagattg acaggctgg actccccatt      240 gcttttctaa aaatcttgga aactttgtcc ttcattgaat tacgcactg tccacccttta    300 atttcctcga aaacgcctgt aactcggctg aagccatgcc ttgtgttcag cgcagtatg     360 ggtcctcgcc tcaaggagcc agccccgctt ctcagagcta cagttaccac tcttcgggag     420
aatacagctc cgatttctta actccagagt ttgtcaagtt tagcatggac ctcaccaaca     480
ctgaaatcac tgccaccact ctctccccca gcttcagtac ctttatggac aactacagca     540
caggctacga cgtcaagcca ccttgcttgt accaaatgcc cctgtccgga cagcagtcct     600
ccattaaggt agaagacatt cagatgcaca actaccagca acacagccac ctgcccccc      660 agtctgagga gatgatgccg cactccgggt cggtttacta caagccctcc tcgccccga     720 cgcccaccac cccgggcttc caggtgcagc acagccccat gtgggacgac ccgggatctc     780
tccacaactt ccaccagaac tacgtggcca ctacgcacat gatcgagcag aggaaaacgc     840
cagtctcccg cctctcccct cttcctccttta gcaatcgcc cctggcacc ccggtgtcta    900 gttgccagat gcgcttcgac gggcccctgc acgtcccat gaacccggag cccgccggca    960
gccaccacgt ggtggacggg cagaccttcg ctgtgcccaa ccccattcgc aagcccgcgt    1020
ccatgggctt cccggggctg cagatcggcc acgcgtctca gctgctcgac acgcaggtgc    1080
```

```
cctcaccgcc gtcgcggggc tccccctcca acgaggggct gtgcgctgtg tgtggggaca    1140
acgcggcctg ccaacactac ggcgtgcgca cctgtgaggg ctgcaaaggc ttctttaagc    1200
gcacagtgca aaaaatgca aaatacgtgt gtttagcaaa taaaaactgc ccagtggaca     1260
agcgtcgccg gaatcgctgt cagtactgcc gatttcagaa gtgcctggct gttgggatgg    1320
tcaaagaagt ggttcgcaca gacagtttaa aaggccggag aggtcgtttg ccctcgaaac    1380
cgaagagccc acaggagccc tctccccctt cgccccggt gagtctgatc agtgccctcg     1440
tcagggccca tgtcgactcc aacccggcta tgaccagcct ggactattcc aggttccagg    1500
cgaaccctga ctatcaaatg agtggagatg acacccagca tatccagcaa ttctatgatc    1560
tcctgactgg ctccatggag atcatccggg gctgggcaga aagatccct ggcttcgcag     1620 acctgcccaa agccgaccaa gacctgcttt tgaatcagc tttcttagaa ctgtttgtcc     1680
ttcgattagc atacaggtcc aacccagtgg agggtaaact catcttttgc aatggggtgg    1740
tcttgcacag gttgcaatgc gttcgtggct ttggggaatg gattgattcc attgttgaat    1800
tctcctccaa cttgcagaat atgaacatcg acatttctgc cttctcctgc attgctgccc    1860
tggctatggt cacagagaga cacgggctca aggaacccaa gagagtggaa gaactgcaaa    1920
acaagattgt aaattgtctc aaagaccacg tgactttcaa caatgggggg ttgaaccgcc    1980
ccaattattt gtccaaactg ttggggaagc tcccagaact tcgtacccctt tgcacacagg   2040 ggctacagcg catttctac ctgaaattgg aagacttggt gccaccgcca gcaataattg     2100
acaaactttt cctggacact ttaccttct aagacctcct cccaagcact tcaaaggaac     2160
tggaatgata atggaaactg tcaagagggg gcaagtcaca tgggcagaga tagccgtgtg    2220
agcagtctca gctcaagctg ccccccattt ctgtaaccct cctagccccc ttgatcccta    2280
aagaaaacaa acaaacaaac aaaaactgtt gctatttcct aacctgcagg cagaacctga    2340
aagggcattt tggctccggg gcatcctgga tttagaacat ggactacaca caatacagtg    2400
gtataaactt tttattctca gtttaaaaat cagtttgttg ttcagaagaa agattgctat    2460
aatgtataat gggaaatgtt tggccatgct tggttgttgc agttcagaca aatgtaacac    2520
acacacacat acacacacac acacacacac agagacacat cttaagggga cccacaagta   2580
ttgcccttta acaagacttc aaagttttct gctgtaaaga aagctgtaat atatagtaaa    2640
actaaatgtt gcgtgggtgg catgagttga agaaggcaaa ggcttgtaaa tttacccaat    2700
gcagtttggc tttttaaatt attttgtgcc tatttatgaa taaatattac aaattctaaa    2760
agataagtgt gtttgcaaaa aaaagaaaa taaatacata aaaagggac aagcatgttg      2820 attctaggtt gaaaatgtta taggcacttg ctacttcagt aatgtctata ttatataaat    2880
agtatttcag acactatgta gtctgttaga ttttataaag attggtagtt atctgagctt    2940
aaacattttc tcaattgtaa aataggtggg cacaagtatt acacatcaga aaatcctgac    3000
aaaagggaca catagtgttt gtaacaccgt ccaacattcc ttgtttgtaa gtgttgtatg    3060
taccgttgat gttgataaaa agaaagttta tatcttgatt attttgttgt ctaaagctaa    3120
acaaaacttg catgcagcag cttttgactg ttttccagagt gcttataata tacataactc   3180
cctggaaata actgagcact ttgaatttt tttatgtcta aaattgtcag ttaatttatt     3240
attttgtttg agtaagaatt ttaatattgc catattctgt agtattttc tttgtatatt     3300 tctagtatgg cacatgatat gagtcactgc cttttttct atggtgtatg acagttagag     3360
atgctgattt tttttctgat aaattctttc tttgagaaag acaattttaa tgtttacaac    3420
aataaaccat gtaaatgaaa aaaaaa                                         3447
```

```
<210> SEQ ID NO 26
<211> LENGTH: 598
<212> TYPE: PRT
<213> ORGANISM: Homo sapiens
<220> FEATURE:
<223> OTHER INFORMATION: Nurr1

<400> SEQUENCE: 26
```

| | | | | | | | | | | | | | | |
|---|---|---|---|---|---|---|---|---|---|---|---|---|---|---|
| Met | Pro | Cys | Val | Gln | Ala | Gln | Tyr | Gly | Ser | Ser | Pro | Gln | Gly | Ala | Ser |
| 1 | | | | 5 | | | | | 10 | | | | | 15 | |

| Pro | Ala | Ser | Gln | Ser | Tyr | Ser | Tyr | His | Ser | Ser | Gly | Glu | Tyr | Ser | Ser |
|---|---|---|---|---|---|---|---|---|---|---|---|---|---|---|---|
| | | | 20 | | | | | 25 | | | | | 30 | | |

| Asp | Phe | Leu | Thr | Pro | Glu | Phe | Val | Lys | Phe | Ser | Met | Asp | Leu | Thr | Asn |
|---|---|---|---|---|---|---|---|---|---|---|---|---|---|---|---|
| | | | 35 | | | | | 40 | | | | | 45 | | |

| Thr | Glu | Ile | Thr | Ala | Thr | Thr | Ser | Leu | Pro | Ser | Phe | Ser | Thr | Phe | Met |
|---|---|---|---|---|---|---|---|---|---|---|---|---|---|---|---|
| | 50 | | | | | 55 | | | | | 60 | | | | |

| Asp | Asn | Tyr | Ser | Thr | Gly | Tyr | Asp | Val | Lys | Pro | Pro | Cys | Leu | Tyr | Gln |
|---|---|---|---|---|---|---|---|---|---|---|---|---|---|---|---|
| 65 | | | | | 70 | | | | | 75 | | | | | 80 |

| Met | Pro | Leu | Ser | Gly | Gln | Gln | Ser | Ser | Ile | Lys | Val | Glu | Asp | Ile | Gln |
|---|---|---|---|---|---|---|---|---|---|---|---|---|---|---|---|
| | | | | 85 | | | | | 90 | | | | | 95 | |

| Met | His | Asn | Tyr | Gln | Gln | His | Ser | His | Leu | Pro | Pro | Gln | Ser | Glu | Glu |
|---|---|---|---|---|---|---|---|---|---|---|---|---|---|---|---|
| | | | 100 | | | | | 105 | | | | | 110 | | |

| Met | Met | Pro | His | Ser | Gly | Ser | Val | Tyr | Tyr | Lys | Pro | Ser | Ser | Pro | Pro |
|---|---|---|---|---|---|---|---|---|---|---|---|---|---|---|---|
| | | 115 | | | | | 120 | | | | | 125 | | | |

| Thr | Pro | Thr | Thr | Pro | Gly | Phe | Gln | Val | Gln | His | Ser | Pro | Met | Trp | Asp |
|---|---|---|---|---|---|---|---|---|---|---|---|---|---|---|---|
| | 130 | | | | | 135 | | | | | 140 | | | | |

| Asp | Pro | Gly | Ser | Leu | His | Asn | Phe | His | Gln | Asn | Tyr | Val | Ala | Thr | Thr |
|---|---|---|---|---|---|---|---|---|---|---|---|---|---|---|---|
| 145 | | | | | 150 | | | | | 155 | | | | | 160 |

| His | Met | Ile | Glu | Gln | Arg | Lys | Thr | Pro | Val | Ser | Arg | Leu | Ser | Leu | Phe |
|---|---|---|---|---|---|---|---|---|---|---|---|---|---|---|---|
| | | | | 165 | | | | | 170 | | | | | 175 | |

| Ser | Phe | Lys | Gln | Ser | Pro | Pro | Gly | Thr | Pro | Val | Ser | Ser | Cys | Gln | Met |
|---|---|---|---|---|---|---|---|---|---|---|---|---|---|---|---|
| | | | 180 | | | | | 185 | | | | | 190 | | |

| Arg | Phe | Asp | Gly | Pro | Leu | His | Val | Pro | Met | Asn | Pro | Glu | Pro | Ala | Gly |
|---|---|---|---|---|---|---|---|---|---|---|---|---|---|---|---|
| | | | 195 | | | | | 200 | | | | | 205 | | |

| Ser | His | His | Val | Val | Asp | Gly | Gln | Thr | Phe | Ala | Val | Pro | Asn | Pro | Ile |
|---|---|---|---|---|---|---|---|---|---|---|---|---|---|---|---|
| | 210 | | | | | 215 | | | | | 220 | | | | |

| Arg | Lys | Pro | Ala | Ser | Met | Gly | Phe | Pro | Gly | Leu | Gln | Ile | Gly | His | Ala |
|---|---|---|---|---|---|---|---|---|---|---|---|---|---|---|---|
| 225 | | | | | 230 | | | | | 235 | | | | | 240 |

| Ser | Gln | Leu | Leu | Asp | Thr | Gln | Val | Pro | Ser | Pro | Pro | Ser | Arg | Gly | Ser |
|---|---|---|---|---|---|---|---|---|---|---|---|---|---|---|---|
| | | | | 245 | | | | | 250 | | | | | 255 | |

| Pro | Ser | Asn | Glu | Gly | Leu | Cys | Ala | Val | Cys | Gly | Asp | Asn | Ala | Ala | Cys |
|---|---|---|---|---|---|---|---|---|---|---|---|---|---|---|---|
| | | | 260 | | | | | 265 | | | | | 270 | | |

| Gln | His | Tyr | Gly | Val | Arg | Thr | Cys | Glu | Gly | Cys | Lys | Gly | Phe | Phe | Lys |
|---|---|---|---|---|---|---|---|---|---|---|---|---|---|---|---|
| | | 275 | | | | | 280 | | | | | 285 | | | |

| Arg | Thr | Val | Gln | Lys | Asn | Ala | Lys | Tyr | Val | Cys | Leu | Ala | Asn | Lys | Asn |
|---|---|---|---|---|---|---|---|---|---|---|---|---|---|---|---|
| | 290 | | | | | 295 | | | | | 300 | | | | |

| Cys | Pro | Val | Asp | Lys | Arg | Arg | Arg | Asn | Arg | Cys | Gln | Tyr | Cys | Arg | Phe |
|---|---|---|---|---|---|---|---|---|---|---|---|---|---|---|---|
| 305 | | | | | 310 | | | | | 315 | | | | | 320 |

| Gln | Lys | Cys | Leu | Ala | Val | Gly | Met | Val | Lys | Glu | Val | Val | Arg | Thr | Asp |
|---|---|---|---|---|---|---|---|---|---|---|---|---|---|---|---|
| | | | | 325 | | | | | 330 | | | | | 335 | |

| Ser | Leu | Lys | Gly | Arg | Arg | Gly | Arg | Leu | Pro | Ser | Lys | Pro | Lys | Ser | Pro |
|---|---|---|---|---|---|---|---|---|---|---|---|---|---|---|---|
| | | | 340 | | | | | 345 | | | | | 350 | | |

| Gln | Glu | Pro | Ser | Pro | Pro | Ser | Pro | Pro | Val | Ser | Leu | Ile | Ser | Ala | Leu |
|---|---|---|---|---|---|---|---|---|---|---|---|---|---|---|---|
| | | 355 | | | | | 360 | | | | | 365 | | | |

| Val | Arg | Ala | His | Val | Asp | Ser | Asn | Pro | Ala | Met | Thr | Ser | Leu | Asp | Tyr |

```
        370                 375                 380
Ser Arg Phe Gln Ala Asn Pro Asp Tyr Gln Met Ser Gly Asp Thr
385                 390                 395                 400

Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
                420                 425                 430

Ala Asp Gln Asp Leu Leu Phe Glu Ser Ala Phe Leu Glu Leu Phe Val
                435                 440                 445

Leu Arg Leu Ala Tyr Arg Ser Asn Pro Val Glu Gly Lys Leu Ile Phe
450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
                500                 505                 510

Thr Glu Arg His Gly Leu Lys Glu Pro Lys Arg Val Glu Glu Leu Gln
                515                 520                 525

Asn Lys Ile Val Asn Cys Leu Lys Asp His Val Thr Phe Asn Asn Gly
530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ala Ile Ile Asp Lys Leu Phe
                580                 585                 590

Leu Asp Thr Leu Pro Phe
                595

<210> SEQ ID NO 27
<211> LENGTH: 2344
<212> TYPE: DNA
<213> ORGANISM: Mus musculus
<220> FEATURE:
<223> OTHER INFORMATION: En1

<400> SEQUENCE: 27
gccgtggctt atccccccat aagaccaat cactgaaatc ttgttgctga aagaaaaaaa      60
agaaagaaag aaaagaaaa gaaaataata gccaagtgtc ttcactgtat ctggatgtct     120
acaaattaga gagggagagagcgagatt tgctccacca gagcgggcga gagccaggcc       180
agacgctcgc ctttcttttt tccgcctgca tccgccctgt gccttcgctg aggcttcgct   240
ttgccttctt cctctccgcg caccccacg ggcccgctgg caaagtgggg tggggagcga     300
ggcgcggggg gcggggccg gcgccgcggc cagggctgcc gggcggccga gcatggaaga     360
acagcagccg gagcctaaaa gtcagcgcga ctcgggcctc ggcgcggtgg cagcggcggc   420
cccgagcggc ctcagtctga gtctgagccc aggagccagc ggcagcagcg gcagcgatgg   480
agacagcgtg ccggtgtccc cgcagccagc gccccgtcg cctcctgcgg caccctgtct   540
gccgcccctg gccatcacc cgcacctccc ccgcatccc ccgcccccgc cgccgccgcc    600
gccgccgcca ccgcagcatc tcgcggcgcc tgctcaccag ccgcagcccg cggcccagct   660
gcaccgcacc accaactttt tcatcgataa catcctaagg cccgatttcg gttgcaaaaa   720
ggaacagccc ctgcctcagc tcctggtggc ttcggctgca gccggaggag gcgcagcagc   780
```

```
aggagggagga agccgcgtgg agcgtgaccg aggccagact ggtgcaggta gagacccgt      840 tcactctctg gcacacgag cttcgggggc tgcctcgctc ttgtgtgctc cagatgcgaa       900
ctgtggccca cccgacggct cccagcccgc caccgctgtc ggcgccggcg catccaaagc      960
cgggaacccg gctgctgcgg cggccgcggc cgcagcagcg gctgcagcgg cagtggcggc     1020
agcggcggca gcagcctcga agccctcgga cagtggcggt ggtagtggag caacgcggg     1080 gagtcccggg gcgcagggcg ccaagttccc ggaacacaac cctgcgatcc tactcatggg     1140
ttcggctaac ggtgggccgg tggtcaagac tgactcacag caaccccctag tgtggcccgc    1200 ctgggtctac tgcacacgct attcggaccg tccgtcctct ggtccacgca ccaggaagct     1260
aaagaagaaa aagaacgaga aggaagacaa gcggccgcgg acggcgttca cggccgagca    1320
gctgcagaga ctcaaggcgg agttccaggc aaaccgctat atcacggagc agcggcgaca    1380
gaccctcgcc caggagctca gcctgaatga gtcccagatc aagatctggt tccaaaacaa    1440
gcgtgccaag atcaagaaag ccacaggcat caagaacggc ctggcgctgc acctcatggc    1500
ccagggactg tacaaccact ctaccaccac ggttcaggac aaagacgaga gcgagtagct    1560
gtggccagct ccggggcccg cggtccaacg gcgcccgtgc cacctccagg ctcctcgggg    1620
ctgccgcttc accagcccca cgcagagacg atcgctatgg agggaggcat caatcagggc    1680
gacagagaaa gcgagcaaga gaaagcaatc ctccgagtgg acattcacat aggaacaaaa    1740 cggttttttaa acgggagtaa gactcggaca ggacaggtgc tatgggggaa aaataaacat    1800
ctattctcta actcactgta taagatgaaa ctgcgaattc cttaaagctc tatcatgcca    1860
aactgcttac gaccgtgtat atatttaatt tcaggtaagg aaaacaaata tgtgtagcga    1920
tctctatttg ctggacattt ttattaatct catttattat tgttataatt attataatta    1980
ttataattat ttttcccctc ctccctacct tgctgcaccc ccccccccc agcccagttt      2040 cgttttcgtt gctctttttcc tttgaatgtt tttgcttctc tgggtacctc ctgcaccccc    2100
aacgctggcc ctggtttctc tgggacttt ctttgtgtga gtgtgagtgt gtttccttgt      2160
gtgtctgccc ctgcctcttc tctatttatt taggattctt ctattggtct tgtctatccc     2220
tcccgtaaat cccttcctt ttctggagac tccttgagaa atacaacccc acagactacg      2280
agactgaacc gccgctacaa gccaaagatt ttattatgtt cagaaacctg tagtctgaaa    2340
taaa                                                                  2344
```

<210> SEQ ID NO 28
<211> LENGTH: 401
<212> TYPE: PRT
<213> ORGANISM: Mus musculus
<220> FEATURE:
<223> OTHER INFORMATION: En1

<400> SEQUENCE: 28

```
Met Glu Glu Gln Gln Pro Glu Pro Lys Ser Gln Arg Asp Ser Gly Leu
 1               5                  10                  15

Gly Ala Val Ala Ala Ala Ala Pro Ser Gly Leu Ser Leu Ser Leu Ser
            20                  25                  30

Pro Gly Ala Ser Gly Ser Ser Gly Ser Asp Gly Asp Ser Val Pro Val
        35                  40                  45

Ser Pro Gln Pro Ala Pro Ser Pro Ala Ala Pro Cys Leu Pro
    50                  55                  60

Pro Leu Ala His His Pro His Leu Pro Pro His Pro Pro Pro Pro
65                  70                  75                  80

Pro Pro Pro Pro Pro Pro Pro Gln His Leu Ala Ala Pro Ala His Gln
```

-continued

```
                    85                  90                  95
Pro Gln Pro Ala Ala Gln Leu His Arg Thr Thr Asn Phe Phe Ile Asp
                100                 105                 110
Asn Ile Leu Arg Pro Asp Phe Gly Cys Lys Lys Glu Gln Pro Leu Pro
            115                 120                 125
Gln Leu Leu Val Ala Ser Ala Ala Gly Gly Ala Ala Gly
        130                 135                 140
Gly Gly Ser Arg Val Glu Arg Asp Arg Gly Gln Thr Gly Ala Gly Arg
145                 150                 155                 160
Asp Pro Val His Ser Leu Gly Thr Arg Ala Ser Gly Ala Ala Ser Leu
                165                 170                 175
Leu Cys Ala Pro Asp Ala Asn Cys Gly Pro Pro Asp Gly Ser Gln Pro
                180                 185                 190
Ala Thr Ala Val Gly Ala Gly Ala Ser Lys Ala Gly Asn Pro Ala Ala
            195                 200                 205
Ala Ala Ala Ala Ala Ala Ala Ala Ala Ala Val Ala Ala
        210                 215                 220
Ala Ala Ala Ala Ser Lys Pro Ser Asp Ser Gly Gly Ser Gly Gly
225                 230                 235                 240
Asn Ala Gly Ser Pro Gly Ala Gln Gly Ala Lys Phe Pro Glu His Asn
                245                 250                 255
Pro Ala Ile Leu Met Gly Ser Ala Asn Gly Gly Pro Val Val Lys
                260                 265                 270
Thr Asp Ser Gln Gln Pro Leu Val Trp Pro Ala Trp Val Tyr Cys Thr
            275                 280                 285
Arg Tyr Ser Asp Arg Pro Ser Ser Gly Pro Arg Thr Arg Lys Leu Lys
        290                 295                 300
Lys Lys Lys Asn Glu Lys Glu Asp Lys Arg Pro Arg Thr Ala Phe Thr
305                 310                 315                 320
Ala Glu Gln Leu Gln Arg Leu Lys Ala Glu Phe Gln Ala Asn Arg Tyr
                325                 330                 335
Ile Thr Glu Gln Arg Arg Gln Thr Leu Ala Gln Glu Leu Ser Leu Asn
                340                 345                 350
Glu Ser Gln Ile Lys Ile Trp Phe Gln Asn Lys Arg Ala Lys Ile Lys
            355                 360                 365
Lys Ala Thr Gly Ile Lys Asn Gly Leu Ala Leu His Leu Met Ala Gln
        370                 375                 380
Gly Leu Tyr Asn His Ser Thr Thr Thr Val Gln Asp Lys Asp Glu Ser
385                 390                 395                 400
Glu

<210> SEQ ID NO 29
<211> LENGTH: 2943
<212> TYPE: DNA
<213> ORGANISM: Homo sapiens
<220> FEATURE:
<223> OTHER INFORMATION: En1

<400> SEQUENCE: 29
gagctcacag acccataatc ctgcatttct ctaacaagtt gtttatggag ttgcttctcc    60
atttgcctac atcccaaaat tcaccctcc cggtttcttc tgccccctcc tgagtcccgg   120
cctgaaggag ggggagggac gcgggtgcgg cgcggtgggg ggagggcgga cccgacgcac   180
agggccagcg ccgaggcgcc ccctctccgc cagcggttga cgcccccgga ttatttatcc   240
gcaaagtccc gcgcgcgccc attgggccga ggcccgagtg tcagcgcgag tcccggctcg   300
```

```
ccattggctc cgcacacgtg cggccctgac tcacgtgctt ccggtttgaa ggcaaaaagt    360
gtgcctgggt gattttttttt ttaagcgaga gagtttgtgc aaagatccga gctgtcagag    420
atttgaaaaa aaaaaaaaaa acaaaaaaaa aaaaaccagc ccggcgctgg cggagacgcg    480
ctctccctgc aaaaaagca aggcgatta aggcgctgc cagcctcacg ctctgggcac       540
agctgagcgt gacactcggg gaagtcaaac ccctcactac tgcctaggaa gatggctaga    600
ctttaaatac tattttttttc cctttaagaa aaaaattatt ggagcttttt ttcttgcttt    660 cttttttcctt ttctttttct tttttcctt cattttttttg gccgtggctt actccccatt    720
taaatcaaat cattgaatct ggttgcagaa agaaaaaaga aatagccaag tgtctccata    780
tctggatgtc tacaaattag agagggagag acagcgagat ctatctgcta gataagaacg    840
agcgatccag gccagacgcc tgagcttttt tcctgcaccc gccccgtgcc ttcgctgagg    900
cttcgcctgc ctccttcctc cgcgcacccc cacgggccgc tggcaaagtg gggtggggag    960
cgaggcggtg ggggcggggg ccggcgcggc ggccggggcg gcggggcggc cgagcatgga   1020
agaacagcag ccggaaccta aaagtcagcg cgactcggcc ctcggcggcg cggcggcggc   1080
gactccgggc ggcctcagcc tgagcctcag tccgggcgcc agcggcagca gcggcagcgg   1140
cagcgatgga gacagcgtgc cggtgtcccc gcagcctgcg ccccctcgc cgcccgcggc    1200 gccttgcctg ccgcccctgg cccaccaccc gcacctcccc ccacaccccc cgccccgcc    1260 gcctcagcat ctcgcggcgc ctgctcacca gccgcagcca gcggcccagc tgcaccgcac   1320
caccaacttt ttcatcgaca acatcctgag gccggacttc ggctgcaaaa aggagcagcc   1380
gccaccgcag cttctggtgg ctgcggcggc cagaggaggc gcaggaggag gaggccgggt   1440
cgagcgtgac agaggccaga ctgccgcagg tagagaccct gtccacccgt tgggcacccg   1500
ggcgccaggc gctgcctcgc tcctgtgcgc cccggacgcg aactgtggcc cacccgacgg   1560
ctcccagcca gccgccgccg gcgcgggcgc gtctaaagct gggaacccgg ctgcggcggc   1620
ggcggcggcc gcggcggcag tggcggcggc ggcggcggcc gcagcagcca gccctcgga    1680 caccggtggc ggcggcagtg gaggcggcgc ggggagcccc ggagcgcagg gcaccaaata   1740
cccggagcac ggcaacccgg ctatcctact tatgggctca gccaacggcg ggcccgtggt   1800
caaaactgac tcgcagcagc ctctcgtatg gcccgcctgg gtgtactgca cacgttattc   1860
ggatcgtcca tcctccggtc cgcgcaccag gaagctgaag aagaagaaga acgagaagga   1920
ggacaagcgg ccgcggaccg cgttcacggc cgagcagctg cagagactca aggcggagtt   1980
ccaggcaaac cgctacatca cggagcagcg gcggcagacc ctggcccagg aactcagcct   2040
caacgagtcc cagatcaaga tctggttcca gaacaagcgc gccaagatca agaaagccac   2100
aggcatcaag aacggcctgg cgctgcacct catggcccag ggactgtaca accactccac   2160
caccacggtc caggacaaag acgagagcga gtagccgcca caggccgggg ccgcgcccgc   2220 gcccctccc ggcaccgccg ccgtcgtctc ccggcccctc gctggggag aaagcatctg     2280 ctccaaggag ggaggagcg cagggaaaag agcgagagag acagaaagag agcctcagaa    2340
tggacaatga cgttgaaacg cagcattttt gaaaagggag aaagactcgg acaggtgcta   2400
tcgaaaaata agatccattc tctattccca gtataaggga cgaaactgcg aactccttaa   2460
agctctatct agccaaaccg cttacgacct tgtatatatt taatttcagg taaggaaaac   2520
acatacgtgt agcgatctct atttgctgga cattttttatt aatctccttt attattattg   2580
ttataattat tataattatt ataattattt tatggccctc ccccaccgcc tcgctgcccc   2640
cgcccagttt cgttttcgtt gccttttttca tttgaatgtc attgcttctc cggtgcctcc   2700
```

```
cgacccgcat cgccggcccct ggtttctctg ggacttttct ttgtgtgcga gagtgtgttt    2760
cctttcgtgt ctgcccacct cttctccccc acctcccggg tcccttctgt cggtctgtct    2820
gttctgcccc cctttcgttt tccggagact tgttgagaaa tacgacccca cagactgcga    2880
gactgaaccg ccgctacaag ccaaagattt tattatgttc agaaacctgt agtctgaaat    2940
aaa                                                                  2943
```

<210> SEQ ID NO 30
<211> LENGTH: 392
<212> TYPE: PRT
<213> ORGANISM: Homo sapiens
<220> FEATURE:
<223> OTHER INFORMATION: En1

<400> SEQUENCE: 30

```
Met Glu Glu Gln Gln Pro Glu Pro Lys Ser Gln Arg Asp Ser Ala Leu
 1               5                  10                  15

Gly Gly Ala Ala Ala Thr Pro Gly Gly Leu Ser Leu Ser Leu Ser
            20                  25                  30

Pro Gly Ala Ser Gly Ser Ser Gly Ser Gly Ser Asp Gly Asp Ser Val
        35                  40                  45

Pro Val Ser Pro Gln Pro Ala Pro Pro Ser Pro Pro Ala Ala Pro Cys
    50                  55                  60

Leu Pro Pro Leu Ala His His Pro His Leu Pro Pro His Pro Pro Pro
65                  70                  75                  80

Pro Pro Pro Gln His Leu Ala Ala Pro Ala His Gln Pro Gln Pro Ala
                85                  90                  95

Ala Gln Leu His Arg Thr Thr Asn Phe Phe Ile Asp Asn Ile Leu Arg
            100                 105                 110

Pro Asp Phe Gly Cys Lys Lys Glu Gln Pro Pro Gln Leu Leu Val
        115                 120                 125

Ala Ala Ala Ala Arg Gly Gly Ala Gly Gly Gly Arg Val Glu Arg
    130                 135                 140

Asp Arg Gly Gln Thr Ala Ala Gly Arg Asp Pro Val His Pro Leu Gly
145                 150                 155                 160

Thr Arg Ala Pro Gly Ala Ala Ser Leu Leu Cys Ala Pro Asp Ala Asn
                165                 170                 175

Cys Gly Pro Pro Asp Gly Ser Gln Pro Ala Ala Ala Gly Ala Gly Ala
            180                 185                 190

Ser Lys Ala Gly Asn Pro Ala Ala Ala Ala Ala Ala Ala Ala Ala
        195                 200                 205

Val Ala Ala Ala Ala Ala Ala Ala Lys Pro Ser Asp Thr Gly
    210                 215                 220

Gly Gly Gly Ser Gly Gly Gly Ala Gly Ser Pro Gly Ala Gln Gly Thr
225                 230                 235                 240

Lys Tyr Pro Glu His Gly Asn Pro Ala Ile Leu Leu Met Gly Ser Ala
                245                 250                 255

Asn Gly Gly Pro Val Val Lys Thr Asp Ser Gln Gln Pro Leu Val Trp
            260                 265                 270

Pro Ala Trp Val Tyr Cys Thr Arg Tyr Ser Asp Arg Pro Ser Ser Gly
        275                 280                 285

Pro Arg Thr Arg Lys Leu Lys Lys Lys Asn Glu Lys Glu Asp Lys
    290                 295                 300

Arg Pro Arg Thr Ala Phe Thr Ala Glu Gln Leu Gln Arg Leu Lys Ala
305                 310                 315                 320
```

```
Glu Phe Gln Ala Asn Arg Tyr Ile Thr Glu Gln Arg Arg Gln Thr Leu
                325                 330                 335

Ala Gln Glu Leu Ser Leu Asn Glu Ser Gln Ile Lys Ile Trp Phe Gln
            340                 345                 350

Asn Lys Arg Ala Lys Ile Lys Lys Ala Thr Gly Ile Lys Asn Gly Leu
        355                 360                 365

Ala Leu His Leu Met Ala Gln Gly Leu Tyr Asn His Ser Thr Thr Thr
    370                 375                 380

Val Gln Asp Lys Asp Glu Ser Glu
385                 390

<210> SEQ ID NO 31
<211> LENGTH: 1392
<212> TYPE: DNA
<213> ORGANISM: Mus musculus
<220> FEATURE:
<223> OTHER INFORMATION: Ptx3

<400> SEQUENCE: 31
tgcggccgcc cagagcaggg ggcggccac  ccgcagggtg cctggcccct ggcccctgcc    60
tgcgctccag aacgccgccg ccacagccac acccggagt  ctgcctgctg cgggacgcac   120
tagacctccc tccatggagt ttgggctgct tggtgaggca gaggcgcgaa gcccgcgct   180 gtcgttatcg gacgcaggca ctccacaccc tccgcttcca gaacatggct gcaaggggca   240
ggagcacagt gactcggaga aggcctcggc ctcactgccg gggggctccc ccgaggacgg   300
ctctctgaag aagaagcagc ggcggcagcg cacgcacttc accagccagc agctgcagga   360
gctggaggcc accttccaga ggaatcgcta ccctgacatg agcacccgcg aagagatcgc   420
ggtgtggacc aacctcactg aggcccgcgt gcgggtgtgg ttcaagaacc ggcgcgccaa   480
gtggcgaaag cgggagcgca ccagcaggg  ggagctgtgc aaaggtggct cgcagcccc   540 gctcggggc  ctggtgccac cctacgagga ggtgtacccg ggctactcgt acggcaactg   600
gccgcccaag gctctcgccc cgccgctcgc cgccaagacc ttcccgttcg ccttcaactc   660
ggtcaacgtg gggcctctgg cttcacagcc tgtattctca ccgcccagct ccatcgccgc   720
ttctatggtg ccctcggccg ccgctgcccc gggcaccgta ccaggtcccg gagccttgca   780
gggcctgggc ggggcaccc  ccgggctggc tccagccgcc gtgtcctccg ggcagtgtc   840 ctgcccttac gcctcggccg ccgcagccgc cgctgcagcc gcctcctccc cctatgtata   900
ccgggacccg tgtaactcga gcctggctag cctgcggctc aaagccaagc agcacgcctc   960
tttcagctat cccgccgtgc ccgggccgcc gccggccgct aaccttagcc cctgccagta  1020
cgccgtggaa cggccggtgt gagccgcagg tctgtggatc catccccgag ggcggggcag  1080
taattcacag cctctccgga caggggtcgc ctagactggc ttgccctcgt cccagggtct  1140
gaaaggggtg ccagagcacc cggaagagg  ccgcgggctt cgaagagggc cttttccctc  1200 gcagccccg  agcggtggtc tgaccccat  gcggagaccg cgccctagg actaaggcca  1260 ggaacaggga ccagctcccc cagggccaat tcacccttgg ctcaccccgc cttctccaga  1320 ctcccccat  cccatttca  aagatcaatg aaataaacgt gcgcggactg tcaaaaaaaa  1380 aaaaaaaaa  aa                                                      1392

<210> SEQ ID NO 32
<211> LENGTH: 302
<212> TYPE: PRT
<213> ORGANISM: Mus musculus
<220> FEATURE:
```

<223> OTHER INFORMATION: Ptx3

<400> SEQUENCE: 32

Met Glu Phe Gly Leu Leu Gly Glu Ala Glu Ala Arg Ser Pro Ala Leu
1               5                   10                  15

Ser Leu Ser Asp Ala Gly Thr Pro His Pro Leu Pro Glu His Gly
            20                  25                  30

Cys Lys Gly Gln Glu His Ser Asp Ser Glu Lys Ala Ser Ala Ser Leu
            35                  40                  45

Pro Gly Gly Ser Pro Glu Asp Gly Ser Leu Lys Lys Gln Arg Arg
    50                  55                  60

Gln Arg Thr His Phe Thr Ser Gln Gln Leu Gln Glu Leu Glu Ala Thr
65                  70                  75                  80

Phe Gln Arg Asn Arg Tyr Pro Asp Met Ser Thr Arg Glu Glu Ile Ala
                85                  90                  95

Val Trp Thr Asn Leu Thr Glu Ala Arg Val Arg Val Trp Phe Lys Asn
            100                 105                 110

Arg Arg Ala Lys Trp Arg Lys Arg Glu Arg Ser Gln Gln Ala Glu Leu
        115                 120                 125

Cys Lys Gly Gly Phe Ala Ala Pro Leu Gly Gly Leu Val Pro Pro Tyr
    130                 135                 140

Glu Glu Val Tyr Pro Gly Tyr Ser Tyr Gly Asn Trp Pro Pro Lys Ala
145                 150                 155                 160

Leu Ala Pro Pro Leu Ala Ala Lys Thr Phe Pro Phe Ala Phe Asn Ser
                165                 170                 175

Val Asn Val Gly Pro Leu Ala Ser Gln Pro Val Phe Ser Pro Pro Ser
            180                 185                 190

Ser Ile Ala Ala Ser Met Val Pro Ser Ala Ala Ala Pro Gly Thr
        195                 200                 205

Val Pro Gly Pro Gly Ala Leu Gln Gly Leu Gly Gly Ala Pro Pro Gly
    210                 215                 220

Leu Ala Pro Ala Ala Val Ser Ser Gly Ala Val Ser Cys Pro Tyr Ala
225                 230                 235                 240

Ser Ala Ala Ala Ala Ala Ala Ala Ser Ser Pro Tyr Val Tyr
                245                 250                 255

Arg Asp Pro Cys Asn Ser Ser Leu Ala Ser Leu Arg Leu Lys Ala Lys
            260                 265                 270

Gln His Ala Ser Phe Ser Tyr Pro Ala Val Pro Gly Pro Pro Ala
    275                 280                 285

Ala Asn Leu Ser Pro Cys Gln Tyr Ala Val Glu Arg Pro Val
290                 295                 300

<210> SEQ ID NO 33
<211> LENGTH: 1407
<212> TYPE: DNA
<213> ORGANISM: Homo sapiens
<220> FEATURE:
<223> OTHER INFORMATION: Ptx3

<400> SEQUENCE: 33
ggagcgcccg agcggagagg cggcccggga gcaggggggc ggcccccact ccggccgggt      60
gcccggcccc tggcccctgc ctgccctcta gatcgccgcc gcagccgccg ctactgggag     120
tctgcctgtt gcaggacgca ctagccctcc ctccatggag ttcggcctgc tcagcgaggc     180
agaggcccgg agcctgcccc tgtcgctgtc agacgctggc actccgcacc ccagctccc     240 agagcacggc tgcaagggcc aggagcacag cgactcagaa aaggcctcgg cttcgctgcc     300

-continued

```
cggcggctcc ccagaggacg gttcgctgaa aaagaagcag cggcggcagc gcacgcactt      360
caccagccag cagctacagg agctagaggc gaccttccag aggaaccgct accccgacat      420
gagcacgcgc gaggagatcg ccgtgtggac caacctcacc gaggcccgcg tgcgggtgtg      480
gttcaagaac cggcgcgcca atggcggaa gcgcgagcgc agccagcagg ccgagctatg       540
caaaggcagc ttcgcggcgc cgctcggggg gctggtgccg ccctacgagg aggtgtaccc      600
cggctactcg tacggcaact ggccgcccaa ggctcttgcc ccgccgctcg ccgccaagac      660
ctttccattc gccttcaact cggtcaacgt ggggcctctg gcttcgcagc ccgtcttctc      720
gccacccagc tccatcgccg cctccatggt gccctccgcc gcggctgccc cgggcaccgt      780
gccagggcct ggggccctgc agggcctggg cgggggcccc ccgggctgg ctccggccgc       840 cgtgtcctcc ggggccgtgt cctgcccctta tgcctcggcc gccgccgcg ccgcggctgc      900 cgcctcttcc ccctacgtct atcgggaccc gtgtaactcg agcctggcca gcctgcggct      960
caaagccaaa cagcacgcct ccttcagcta ccccgctgtg cacgggccgc cccggcagc     1020 caaccttagt ccgtgccagt acgccgtgga aggcccgta tgagcggccc cgcccgtaga     1080
tcatccccga gggcggggc aacgattcac agcctccgcg gactgggtc attttgactg      1140 gcttgctccc gccccagggt ctgaaagggg tgtttgggca gctgggggc accggctcag     1200 gagagggcct tcccctccca gccctgaggg gtggactagg ccctacacac agaccgcgcc     1260
cctgggacta aagccaggaa cagggaccag ctccccgggg gccaactcac ccttggccca     1320
tcccgccttc tccaggcttc ccctccctcg ttttcaaaga taaatgaaat aaacgtgcgc     1380
ggactgtcaa aaaaaaaaaa aaaaaaa                                         1407
```

<210> SEQ ID NO 34
<211> LENGTH: 302
<212> TYPE: PRT
<213> ORGANISM: Homo sapiens
<220> FEATURE:
<223> OTHER INFORMATION: Ptx3

<400> SEQUENCE: 34

```
Met Glu Phe Gly Leu Leu Ser Glu Ala Glu Ala Arg Ser Pro Ala Leu
 1               5                  10                  15

Ser Leu Ser Asp Ala Gly Thr Pro His Pro Gln Leu Pro Glu His Gly
            20                  25                  30

Cys Lys Gly Gln Glu His Ser Asp Ser Glu Lys Ala Ser Ala Ser Leu
        35                  40                  45

Pro Gly Gly Ser Pro Glu Asp Gly Ser Leu Lys Lys Gln Arg Arg
    50                  55                  60

Gln Arg Thr His Phe Thr Ser Gln Gln Leu Gln Glu Leu Glu Ala Thr
65                  70                  75                  80

Phe Gln Arg Asn Arg Tyr Pro Asp Met Ser Thr Arg Glu Glu Ile Ala
                85                  90                  95

Val Trp Thr Asn Leu Thr Glu Ala Arg Val Arg Val Trp Phe Lys Asn
            100                 105                 110

Arg Arg Ala Lys Trp Arg Lys Arg Glu Arg Ser Gln Gln Ala Glu Leu
        115                 120                 125

Cys Lys Gly Ser Phe Ala Ala Pro Leu Gly Gly Leu Val Pro Pro Tyr
    130                 135                 140

Glu Glu Val Tyr Pro Gly Tyr Ser Tyr Gly Asn Trp Pro Pro Lys Ala
145                 150                 155                 160

Leu Ala Pro Pro Leu Ala Ala Lys Thr Phe Pro Phe Ala Phe Asn Ser
```

165                 170                 175
Val Asn Val Gly Pro Leu Ala Ser Gln Pro Val Phe Ser Pro Pro Ser
                180                 185                 190

Ser Ile Ala Ala Ser Met Val Pro Ser Ala Ala Ala Pro Gly Thr
            195                 200                 205

Val Pro Gly Pro Gly Ala Leu Gln Gly Leu Gly Gly Pro Pro Gly
        210                 215                 220

Leu Ala Pro Ala Ala Val Ser Ser Gly Ala Val Ser Cys Pro Tyr Ala
225                 230                 235                 240

Ser Ala Ala Ala Ala Ala Ala Ala Ser Ser Pro Tyr Val Tyr
                245                 250                 255

Arg Asp Pro Cys Asn Ser Ser Leu Ala Ser Leu Arg Leu Lys Ala Lys
                260                 265                 270

Gln His Ala Ser Phe Ser Tyr Pro Ala Val His Gly Pro Pro Ala
            275                 280                 285

Ala Asn Leu Ser Pro Cys Gln Tyr Ala Val Glu Arg Pro Val
        290                 295                 300

<210> SEQ ID NO 35
<211> LENGTH: 1757
<212> TYPE: DNA
<213> ORGANISM: Mus musculus
<220> FEATURE:
<223> OTHER INFORMATION: tyrosine hydroxylase (TH)

<400> SEQUENCE: 35
gcactatgcc cacccccagc gcctcctcgc cacagcccaa gggcttcaga agagccgtct      60
cagagcagga taccaagcag gccgaggctg tcacgtcccc aaggttcatt ggacggcggc     120
agagtctcat cgaggatgcc cgcaaggagc gggaggcagc agcagctgca gcagcggctg     180
cggtagcctc cgcggaacct gggaacccat tggaggctgt ggtattcgag agagggatg      240 gaaatgctgt tctcaacctg ctcttctcct tgaggggtac aaaaccctcc tcactgtctc     300
gggctttgaa agtgtttgag acatttgaag ccaaaatcca ccactagag acccggcctg      360 cccagaggcc actggcagga agcccccacc tggagtactt tgtgcgcttc gaggtgccca     420
gtggcgacct ggctgccctc ctcagttctg tgcgtcgggt gtctgacgat gtgcgcagtg     480
ccagagagga caaggttccc tggttcccaa ggaaagtgtc agagttggat aagtgtcacc     540
acctggtcac caagtttgac cctgacctgg acctggacca tccgggcttc tctgaccagg     600
cgtatcgcca cgcgccggaag ctgattcag agattgcctt ccaatacaag cagggtgagc     660
caattcccca cgtggaatac acaaaggagg aaattgctac ctggaaggag gtatacgcca     720
cgctgaaggg cctctatgct acccatgcct gccgggaaca cctggaggct ttccagcttc     780
tggaacggta ctgtggctac cgagaggaca gcattccaca gctggaggat gtgtctcact     840
tcttgaagga acggactggc ttccagctgc gacccgtggc cggtctactg tctgcccgtg     900
attttctggc cagtctggcc ttccgtgtgt tcagtgcac acagtacatc cgtcatgcct     960
cctcacctat gcactcaccc gagccagact gctgccacga gctgctggga cacgtaccca    1020
tgttggctga ccgcacattt gcccagttct cccaggacat tggacttgca tctctgggg    1080 cttcagatga agaaattgaa aaactctcca cggtgtactg gttcactgtg agttttggc    1140 tgtgtaaaca gaatggggag ctgaaggctt acggtgcagg gctgctgtct tcctatggag    1200
agctcctgca ctccctgtca gaggagcccg aggtccgggc cttgaccca gacacagcag    1260 ccgtgcagcc ctaccaagat caaacctacc agccggtgta cttcgtgtca gagagcttca    1320

```
gtgatgccaa ggacaagctc aggaactatg cctctcgtat ccagcgccca ttctctgtga    1380
agtttgaccc gtacccctg gccattgatg tactggacag tcctcacacc atccggcgct    1440
ccttagaggg ggtccaggat gagctgcaca ccctgaccca agcactgagt gccattagct    1500
aaatgcatag gtaccaccc acaggtgcca ggggcctttc ccaaagttcc cagccccttc    1560 tccaacctttt cctggcccag aggctttccc atgtgtgtgg ctggacccctt tgatgggctg    1620 ctcttggtcc ccctcctcca ctgcttctca accacatctt actactgcat gcgctccagg    1680
atggtcctgc attcctcctg cccttcatgc tgtattctac cctgattatt atctcaataa    1740
aggaaggaaa ggtctcc                                                   1757

<210> SEQ ID NO 36
<211> LENGTH: 498
<212> TYPE: PRT
<213> ORGANISM: Mus musculus
<220> FEATURE:
<223> OTHER INFORMATION: tyrosine hydroxylase (TH)

<400> SEQUENCE: 36

Met Pro Thr Pro Ser Ala Ser Ser Pro Gln Pro Lys Gly Phe Arg Arg
1               5                   10                  15

Ala Val Ser Glu Gln Asp Thr Lys Gln Ala Glu Ala Val Thr Ser Pro
            20                  25                  30

Arg Phe Ile Gly Arg Arg Gln Ser Leu Ile Glu Asp Ala Arg Lys Glu
        35                  40                  45

Arg Glu Ala Ala Ala Ala Ala Ala Ala Val Ala Ser Ala Glu
    50                  55                  60

Pro Gly Asn Pro Leu Glu Ala Val Val Phe Glu Glu Arg Asp Gly Asn
65              70                  75                  80

Ala Val Leu Asn Leu Leu Phe Ser Leu Arg Gly Thr Lys Pro Ser Ser
                85                  90                  95

Leu Ser Arg Ala Leu Lys Val Phe Glu Thr Phe Glu Ala Lys Ile His
            100                 105                 110

His Leu Glu Thr Arg Pro Ala Gln Arg Pro Leu Ala Gly Ser Pro His
        115                 120                 125

Leu Glu Tyr Phe Val Arg Phe Glu Val Pro Ser Gly Asp Leu Ala Ala
    130                 135                 140

Leu Leu Ser Ser Val Arg Arg Val Ser Asp Asp Val Arg Ser Ala Arg
145                 150                 155                 160

Glu Asp Lys Val Pro Trp Phe Pro Arg Lys Val Ser Glu Leu Asp Lys
                165                 170                 175

Cys His His Leu Val Thr Lys Phe Asp Pro Asp Leu Asp Leu Asp His
            180                 185                 190

Pro Gly Phe Ser Asp Gln Ala Tyr Arg Gln Arg Arg Lys Leu Ile Ala
        195                 200                 205

Glu Ile Ala Phe Gln Tyr Lys Gln Gly Glu Pro Ile Pro His Val Glu
    210                 215                 220

Tyr Thr Lys Glu Glu Ile Ala Thr Trp Lys Glu Val Tyr Ala Thr Leu
225                 230                 235                 240

Lys Gly Leu Tyr Ala Thr His Ala Cys Arg Glu His Leu Glu Ala Phe
                245                 250                 255

Gln Leu Leu Glu Arg Tyr Cys Gly Tyr Arg Glu Asp Ser Ile Pro Gln
            260                 265                 270

Leu Glu Asp Val Ser His Phe Leu Lys Glu Arg Thr Gly Phe Gln Leu
        275                 280                 285
```

```
Arg Pro Val Ala Gly Leu Leu Ser Ala Arg Asp Phe Leu Ala Ser Leu
            290                 295                 300

Ala Phe Arg Val Phe Gln Cys Thr Gln Tyr Ile Arg His Ala Ser Ser
305                 310                 315                 320

Pro Met His Ser Pro Glu Pro Asp Cys Cys His Glu Leu Leu Gly His
                325                 330                 335

Val Pro Met Leu Ala Asp Arg Thr Phe Ala Gln Phe Ser Gln Asp Ile
                340                 345                 350

Gly Leu Ala Ser Leu Gly Ala Ser Asp Glu Glu Ile Glu Lys Leu Ser
            355                 360                 365

Thr Val Tyr Trp Phe Thr Val Glu Phe Gly Leu Cys Lys Gln Asn Gly
            370                 375                 380

Glu Leu Lys Ala Tyr Gly Ala Gly Leu Leu Ser Ser Tyr Gly Glu Leu
385                 390                 395                 400

Leu His Ser Leu Ser Glu Glu Pro Glu Val Arg Ala Phe Asp Pro Asp
                405                 410                 415

Thr Ala Ala Val Gln Pro Tyr Gln Asp Gln Thr Tyr Gln Pro Val Tyr
                420                 425                 430

Phe Val Ser Glu Ser Phe Ser Asp Ala Lys Asp Lys Leu Arg Asn Tyr
            435                 440                 445

Ala Ser Arg Ile Gln Arg Pro Phe Ser Val Lys Phe Asp Pro Tyr Thr
450                 455                 460

Leu Ala Ile Asp Val Leu Asp Ser Pro His Thr Ile Arg Arg Ser Leu
465                 470                 475                 480

Glu Gly Val Gln Asp Glu Leu His Thr Leu Thr Gln Ala Leu Ser Ala
                485                 490                 495

Ile Ser

<210> SEQ ID NO 37
<211> LENGTH: 1921
<212> TYPE: DNA
<213> ORGANISM: Homo sapiens
<220> FEATURE:
<223> OTHER INFORMATION: tyrosine hydroxylase (TH)

<400> SEQUENCE: 37
cactgagcca tgcccacccc cgacgccacc acgccacagg ccaagggctt ccgcagggcc      60
gtgtctgagc tggacgccaa gcaggcagag gccatcatgg taagagggca gggcgccccg     120
gggcccagcc tcacaggctc tccgtggcct ggaactgcag ccccagctgc atcctacacc     180
cccaccccaa ggtcccgcg gttcattggg cgcaggcaga gcctcatcga ggacgcccgc     240
aaggagcggg aggcggcggt ggcagcagcg gccgctgcag tccctcgga gcccggggac     300 cccctggagg ctgtggcctt tgaggagaag gaggggaagg ccgtgctaaa cctgctcttc     360
tccccgaggg ccaccaagcc ctcggcgctg tcccgagctg tgaaggtgtt tgagacgttt     420
gaagccaaaa tccaccatct agagacccgg gccgcccaga ggccgcgagc tgggggcccc     480
cacctggagt acttcgtgcg cctcgaggtg cgccgagggg acctggccgc cctgctcagt     540
ggtgtgcgcc aggtgtcaga ggacgtgcgc agccccgcgg ggcccaaggt ccctggttc     600 ccaagaaaag tgtcagagct ggacaagtgt catcacctgg tcaccaagtt cgaccctgac     660
ctggacttgg accacccggg cttctcggac caggtgtacc gccagcgcag gaagctgatt     720
gctgagatcg ccttccagta caggcacggc gacccgattc ccgtgtggga gtacaccgcc     780
gaggagattg ccacctggaa ggaggtctac accacgctga aggcctcta cgccacgcac     840 gcctgcgggg agcacctgga ggcctttgct tgctggagc gcttcagcgg ctaccgggaa     900
```

```
gacaatatcc cccagctgga ggacgtctcc cgcttcctga aggagcgcac gggcttccag    960
ctgcggcctg tggccggcct gctgtccgcc cgggacttcc tggccagcct ggccttccgc   1020
gtgttccagt gcacccagta tatccgccac gcgtcctcgc ccatgcactc ccctgagccg   1080
gactgctgcc acgagctgct ggggcacgtg cccatgctgg ccgaccgcac cttcgcgcag   1140
ttctcgcagg acattggcct ggcgtccctg ggggcctcgg atgaggaaat tgagaagctg   1200
tccacgctgt catggttcac ggtggagttc gggctgtgta agcagaacgg ggaggtgaag   1260
gcctatggtg ccgggctgct gtcctcctac ggggagctcc tgcactgcct gtctgaggag   1320
cctgagattc gggccttcga ccctgaggct gcggccgtgc agccctacca agaccagacg   1380
taccagtcag tctacttcgt gtctgagagc ttcagtgacg ccaaggacaa gctcaggagc   1440
tatgcctcac gcatccagcg ccccttctcc gtgaagttcg accgtacac gctggccatc    1500 gacgtgctgg acagccccca ggccgtgcgg cgctccctgg agggtgtcca ggatgagctg   1560
gacacccttg cccatgcgct gagtgccatt ggctaggtgc acggcgtccc tgagggccct   1620
tcccaacctc ccctggtcct gcactgtccc ggagctcagg ccctggtgag gggctgggtc   1680
ccgggtgccc cccatgccct ccctgctgcc aggctcccac tgcccctgca cctgcttctc   1740
agcgcaacag ctgtgtgtgc ccgtggtgag gttgtgctgc ctgtggtgag gtcctgtcct   1800
ggctcccagg gtcctggggg ctgctgcact gccctccgcc cttccctgac actgtctgct   1860
gccccaatca ccgtcacaat aaaagaaact gtggtctcta aaaaaaaaa aaaaaaaaa    1920 a                                                                    1921
```

<210> SEQ ID NO 38
<211> LENGTH: 528
<212> TYPE: PRT
<213> ORGANISM: Homo sapiens
<220> FEATURE:
<223> OTHER INFORMATION: tyrosine hydroxylase (TH)

<400> SEQUENCE: 38

```
Met Pro Thr Pro Asp Ala Thr Thr Pro Gln Ala Lys Gly Phe Arg Arg
  1               5                  10                  15

Ala Val Ser Glu Leu Asp Ala Lys Gln Ala Glu Ala Ile Met Val Arg
             20                  25                  30

Gly Gln Gly Ala Pro Gly Pro Ser Leu Thr Gly Ser Pro Trp Pro Gly
         35                  40                  45

Thr Ala Pro Ala Ala Ser Tyr Thr Pro Thr Pro Arg Ser Pro Arg
 50                  55                  60

Phe Ile Gly Arg Arg Gln Ser Leu Ile Glu Asp Ala Arg Lys Glu Arg
 65                  70                  75                  80

Glu Ala Ala Val Ala Ala Ala Ala Ala Val Pro Ser Glu Pro Gly
                 85                  90                  95

Asp Pro Leu Glu Ala Val Ala Phe Glu Glu Lys Glu Gly Lys Ala Val
                100                 105                 110

Leu Asn Leu Leu Phe Ser Pro Arg Ala Thr Lys Pro Ser Ala Leu Ser
            115                 120                 125

Arg Ala Val Lys Val Phe Glu Thr Phe Glu Ala Lys Ile His His Leu
    130                 135                 140

Glu Thr Arg Pro Ala Gln Arg Pro Arg Ala Gly Gly Pro His Leu Glu
145                 150                 155                 160

Tyr Phe Val Arg Leu Glu Val Arg Gly Asp Leu Ala Ala Leu Leu
                165                 170                 175
```

| | | | | | | | | | | |
|---|---|---|---|---|---|---|---|---|---|---|
|Ser|Gly|Val|Arg|Gln|Val|Ser|Glu|Asp|Val|Arg|Ser|Pro|Ala|Gly|Pro|
| | | |180| | | |185| | | |190| | | | |

Lys Val Pro Trp Phe Pro Arg Lys Val Ser Glu Leu Asp Lys Cys His
              195                 200                 205

His Leu Val Thr Lys Phe Asp Pro Asp Leu Asp Leu Asp His Pro Gly
        210                 215                 220

Phe Ser Asp Gln Val Tyr Arg Gln Arg Lys Leu Ile Ala Glu Ile
225                 230                 235                 240

Ala Phe Gln Tyr Arg His Gly Asp Pro Ile Pro Arg Val Glu Tyr Thr
                245                 250                 255

Ala Glu Glu Ile Ala Thr Trp Lys Glu Val Tyr Thr Thr Leu Lys Gly
            260                 265                 270

Leu Tyr Ala Thr His Ala Cys Gly Glu His Leu Glu Ala Phe Ala Leu
        275                 280                 285

Leu Glu Arg Phe Ser Gly Tyr Arg Glu Asp Asn Ile Pro Gln Leu Glu
    290                 295                 300

Asp Val Ser Arg Phe Leu Lys Glu Arg Thr Gly Phe Gln Leu Arg Pro
305                 310                 315                 320

Val Ala Gly Leu Leu Ser Ala Arg Asp Phe Leu Ala Ser Leu Ala Phe
                325                 330                 335

Arg Val Phe Gln Cys Thr Gln Tyr Ile Arg His Ala Ser Ser Pro Met
            340                 345                 350

His Ser Pro Glu Pro Asp Cys Cys His Glu Leu Leu Gly His Val Pro
        355                 360                 365

Met Leu Ala Asp Arg Thr Phe Ala Gln Phe Ser Gln Asp Ile Gly Leu
    370                 375                 380

Ala Ser Leu Gly Ala Ser Asp Glu Glu Ile Glu Lys Leu Ser Thr Leu
385                 390                 395                 400

Ser Trp Phe Thr Val Glu Phe Gly Leu Cys Lys Gln Asn Gly Glu Val
                405                 410                 415

Lys Ala Tyr Gly Ala Gly Leu Leu Ser Ser Tyr Gly Glu Leu Leu His
            420                 425                 430

Cys Leu Ser Glu Glu Pro Glu Ile Arg Ala Phe Asp Pro Glu Ala Ala
        435                 440                 445

Ala Val Gln Pro Tyr Gln Asp Gln Thr Tyr Gln Ser Val Tyr Phe Val
    450                 455                 460

Ser Glu Ser Phe Ser Asp Ala Lys Asp Lys Leu Arg Ser Tyr Ala Ser
465                 470                 475                 480

Arg Ile Gln Arg Pro Phe Ser Val Lys Phe Asp Pro Tyr Thr Leu Ala
                485                 490                 495

Ile Asp Val Leu Asp Ser Pro Gln Ala Val Arg Arg Ser Leu Glu Gly
            500                 505                 510

Val Gln Asp Glu Leu Asp Thr Leu Ala His Ala Leu Ser Ala Ile Gly
    515                 520                 525

<210> SEQ ID NO 39
<211> LENGTH: 3393
<212> TYPE: DNA
<213> ORGANISM: Mus musculus
<220> FEATURE:
<223> OTHER INFORMATION: DAT

<400> SEQUENCE: 39
acaggacctc aaagctgaag tctgacgctg gaggcagtcg aagaagaagg aaacagactt      60
cctcgggctc ccgtctaccc atgagtaaaa gcaaatgctc cgtgggacca atgtcttctg     120

```
tggtggcccc ggctaaagag cccaatgctg tgggccccag agaggtggag ctcatcttgg    180
tcaaggagca gaatggagtg cagctgacca actccaccct catcaaccca ccgcagacac    240
cagtggaggt tcaagagcgg gagacctgga gcaagaaaat cgatttcctg ctctcagtca    300
tcggcttcgc tgtggacctg gccaatgtct ggaggtttcc ctacctgtgc tacaaaaatg    360
gtggaggtgc cttcctggtg ccctacctgc tcttcatggt tattgccggg atgcccctct    420
tctacatgga gctggctctc gggcagttca acagagaagg agctgctggt gtctggaaga    480
tctgccctgt cctgaaaggt gtgggcttca ctgtcatcct catctctttc tacgtgggct    540
tcttctacaa tgtcatcatt gcatgggcac tgcactactt cttctcctcc ttcaccatgg    600
acctcccatg gatccactgc aacaacacct ggaacagccc caactgctct gatgcacata    660
gcagcaactc tagcgatggc ctgggcctca acgacacctt gggaccacac ccgctgctg     720 agtattttga gcgtggtgtg ctgcacctcc atcagagtcg tggcattgat gacctgggcc    780
ctccacggtg gcagctcaca gcctgcctgg tgctggtcat tgttctgctc tacttcagcc    840
tgtggaaggg agtaaagact tcagggaagg tggtgtggat cacagctacc atgccctatg    900
tagtcctcac agccctgctc ctgcgtggag tcacccctcc tggggccatg gatggcatca    960
gagcatacct cagtgtggac ttctaccgtc tctgtgaggc atctgtgtgg atcgatgccg   1020
ccacccaggt gtgcttctcc cttggcgttg ggtttgggt gctgattgcc ttctccagtt    1080
acaataagtt caccaataac tgctatagag atgcaatcat caccacctcc attaactccc   1140
tgacgagctt ctcctctggc ttcgttgtct ctccttcct ggggtacatg gcacagaagc     1200
acaatgtgcc catcagggat gtggccacag atggacctgg gttgatcttc atcatctacc   1260
ctgaggcaat cgccacactc ccgctgtctt cagcctgggc cgctgtcttc ttcctcatgc   1320
tgctcactct gggtatcgac agtgccatgg ggggcatgga gtctgtgatc actgggcttg   1380
tcgatgagtt ccagctgcta catcggcatc gagagctctt cactcttggc attgtcctgg   1440
ctactttcct gctgtctctc ttctgtgtca ccaacggtgg catctatgtc ttcacactgc   1500
tggaccactt tgcagctggc acatctatcc tctttggagt gctcattgaa gccattgggg   1560
tggcctggtt ctacggtgtc cagcaattca gtgatgacat caagcagatg actgggcagc   1620
gacccaacct gtactggcgg ctatgctgga agctggtcag cccctgcttc cttctgtatg   1680
tggtcgtggt cagcattgtg accttcagac ccccacacta tggagcctac atcttcccag   1740
actgggccaa tgccctgggc tggatcattg ccacatcctc catggccatg gtgcccattt   1800
atgccaccta taagttctgc agcctgccag ggtccttccg agagaaactg gcctatgcca   1860
tcacacctga gaaagaccgc cagctagtgg acagagggga ggtgcgccaa ttcacgctgc   1920
gccattggct gttggtgtaa agtggaagga gacagctgcc agctgggcca tctcacaaca   1980
gcggggacag ggagatcaca aaggaaacca acacgtcaag aaaggagggc cacttccaca   2040 gtccccttt gccatatgga aaataatcc aagcatgggc ttcaatcttt gactgttcac      2100
acccaatcca tgccacaaag aagcctctgt ctgtgtgtga ctgtaaaaac acacacctct    2160
atacagtgaa gtcaaccatg tccctgtccc taatgggtgg ggaaacccct agctggtatc   2220
ctgtcctgca aggctgactc ccccatctgt ggtcactctg ggagaacagg tcatactgtt    2280
ccctgcattc taggagaggg actttggtac ctgtatatac actgtgccag aatcctgtgc   2340
tcacggtagt tgcctagata atttctttg cttaaattta cagtgtcaag tatcctatt      2400 tttgctgttg gtagaaaaga cagttaatac atgccaagtc cttcctggt gcttggctcc     2460 gagcagacac catgacctta gcatcctgtt cacatattac acacacgcag ggtctgttct    2520
```

```
gagccacgga ggacaaggga cttggtgcag gtgaccagag gttagggttt ttttttcccc    2580
tttattgctg agataaaatt catgaattca ggttgggaga caagccctac tcctggcccc    2640
tggaaggcct ggtcagcttg cagccacttt agtatggact tgtagaccac agagaaagtg    2700
tacttctcct agccagtgtg tccctgcctc ctggacacct gctcttcaca gagtctcaat    2760
gcaacctgaa gatcatattc ttggcctgga gccctgcctg gttttcgggg aaagacaccc    2820
acttcttggg tttgatttcc gactggctcc tgtcataccc atggacatta tccatgttat    2880
aaatggcttt ttaaaaccat atttatgtgt gaatcaaaat tattctcaaa gtgtaaggtt    2940
agtttgttca aatccatttg ctgaagagta gttagcataa gaagaaggta tgccaaaaat    3000
accttctcct ggagagctgg ctttaacctc tgaagtgaaa agtggaagtc atgattttcc    3060
ttgagctcat aactgtgaac tttggcctag cctgtgtccc atagaaatgg caccatgtgt    3120
ctgtctgaga gccaacctta ggtattctct gcaagtagac agtggcacga agatcttgaa    3180
tgtgctacca gggtggaaat gcaggcctgt tggctctgca gactgtagcg tggctgagaa    3240
gaatcaggtt taccatctcc tctcagagct gagtggctcc atgtataaat ccaggtgttg    3300
tcagcatctg ttatttatgt ctatagccag tgccttgttg tgggtcctta taaacaataa    3360
aagaaatata tgttggaaaa aaaaaaaaaa aaa                                 3393
```

<210> SEQ ID NO 40
<211> LENGTH: 619
<212> TYPE: PRT
<213> ORGANISM: Mus musculus
<220> FEATURE:
<223> OTHER INFORMATION: DAT

<400> SEQUENCE: 40

```
Met Ser Lys Ser Lys Cys Ser Val Gly Pro Met Ser Ser Val Val Ala
 1               5                  10                  15

Pro Ala Lys Glu Pro Asn Ala Val Gly Pro Arg Glu Val Glu Leu Ile
            20                  25                  30

Leu Val Lys Glu Gln Asn Gly Val Gln Leu Thr Asn Ser Thr Leu Ile
        35                  40                  45

Asn Pro Pro Gln Thr Pro Val Glu Val Gln Glu Arg Glu Thr Trp Ser
    50                  55                  60

Lys Lys Ile Asp Phe Leu Leu Ser Val Ile Gly Phe Ala Val Asp Leu
65                  70                  75                  80

Ala Asn Val Trp Arg Phe Pro Tyr Leu Cys Tyr Lys Asn Gly Gly Gly
                85                  90                  95

Ala Phe Leu Val Pro Tyr Leu Leu Phe Met Val Ile Ala Gly Met Pro
            100                 105                 110

Leu Phe Tyr Met Glu Leu Ala Leu Gly Gln Phe Asn Arg Glu Gly Ala
        115                 120                 125

Ala Gly Val Trp Lys Ile Cys Pro Val Leu Lys Gly Val Gly Phe Thr
    130                 135                 140

Val Ile Leu Ile Ser Phe Tyr Val Gly Phe Phe Tyr Asn Val Ile Ile
145                 150                 155                 160

Ala Trp Ala Leu His Tyr Phe Phe Ser Ser Phe Thr Met Asp Leu Pro
                165                 170                 175

Trp Ile His Cys Asn Asn Thr Trp Asn Ser Pro Asn Cys Ser Asp Ala
            180                 185                 190

His Ser Ser Asn Ser Ser Asp Gly Leu Gly Leu Asn Asp Thr Phe Gly
        195                 200                 205

Thr Thr Pro Ala Ala Glu Tyr Phe Glu Arg Gly Val Leu His Leu His
```

```
                    210                 215                 220
Gln Ser Arg Gly Ile Asp Asp Leu Gly Pro Pro Arg Trp Gln Leu Thr
225                 230                 235                 240

Ala Cys Leu Val Leu Val Ile Val Leu Leu Tyr Phe Ser Leu Trp Lys
                245                 250                 255

Gly Val Lys Thr Ser Gly Lys Val Val Trp Ile Thr Ala Thr Met Pro
                260                 265                 270

Tyr Val Leu Thr Ala Leu Leu Arg Gly Val Thr Leu Pro Gly
                275                 280                 285        Gly

Ala Met Asp Gly Ile Arg Ala Tyr Leu Ser Val Asp Phe Tyr Arg Leu
290                 295                 300

Cys Glu Ala Ser Val Trp Ile Asp Ala Ala Thr Gln Val Cys Phe Ser
305                 310                 315                 320

Leu Gly Val Gly Phe Gly Val Leu Ile Ala Phe Ser Ser Tyr Asn Lys
                325                 330                 335

Phe Thr Asn Asn Cys Tyr Arg Asp Ala Ile Ile Thr Thr Ser Ile Asn
                340                 345                 350

Ser Leu Thr Ser Phe Ser Ser Gly Phe Val Val Phe Ser Phe Leu Gly
                355                 360                 365

Tyr Met Ala Gln Lys His Asn Val Pro Ile Arg Asp Val Ala Thr Asp
370                 375                 380

Gly Pro Gly Leu Ile Phe Ile Ile Tyr Pro Glu Ala Ile Ala Thr Leu
385                 390                 395                 400

Pro Leu Ser Ser Ala Trp Ala Ala Val Phe Phe Leu Met Leu Leu Thr
                405                 410                 415

Leu Gly Ile Asp Ser Ala Met Gly Gly Met Glu Ser Val Ile Thr Gly
                420                 425                 430

Leu Val Asp Glu Phe Gln Leu Leu His Arg His Arg Glu Leu Phe Thr
                435                 440                 445

Leu Gly Ile Val Leu Ala Thr Phe Leu Leu Ser Leu Phe Cys Val Thr
                450                 455                 460

Asn Gly Gly Ile Tyr Val Phe Thr Leu Leu Asp His Phe Ala Ala Gly
465                 470                 475                 480

Thr Ser Ile Leu Phe Gly Val Leu Ile Glu Ala Ile Gly Val Ala Trp
                485                 490                 495

Phe Tyr Gly Val Gln Gln Phe Ser Asp Asp Ile Lys Gln Met Thr Gly
                500                 505                 510

Gln Arg Pro Asn Leu Tyr Trp Arg Leu Cys Trp Lys Leu Val Ser Pro
                515                 520                 525

Cys Phe Leu Leu Tyr Val Val Val Ser Ile Val Thr Phe Arg Pro
530                 535                 540                       Pro

Pro His Tyr Gly Ala Tyr Ile Phe Pro Asp Trp Ala Asn Ala Leu Gly
545                 550                 555                 560

Trp Ile Ile Ala Thr Ser Ser Met Ala Met Val Pro Ile Tyr Ala Thr
                565                 570                 575

Tyr Lys Phe Cys Ser Leu Pro Gly Ser Phe Arg Glu Lys Leu Ala Tyr
                580                 585                 590

Ala Ile Thr Pro Glu Lys Asp Arg Gln Leu Val Asp Arg Gly Glu Val
                595                 600                 605

Arg Gln Phe Thr Leu Arg His Trp Leu Leu Val
                610                 615

<210> SEQ ID NO 41
<211> LENGTH: 3946
```

```
<212> TYPE: DNA
<213> ORGANISM: Homo sapiens
<220> FEATURE:
<223> OTHER INFORMATION: DAT

<400> SEQUENCE: 41
accgctccgg agcgggaggg gaggcttcgc ggaacgctct cggcgccagg actcgcgtgc      60
aaagcccagg cccgggcggc cagaccaaga gggaagaagc acagaattcc tcaactccca    120
gtgtgcccat gagtaagagc aaatgctccg tgggactcat gtcttccgtg gtggcccgg     180
ctaaggagcc caatgccgtg ggcccgaagg aggtggagct catccttgtc aaggagcaga    240
acggagtgca gctcaccagc tccaccctca ccaacccgcg gcagagcccc gtggaggccc    300
aggatcggga gacctgggc aagaagatcg actttctcct gtccgtcatt ggctttgctg     360
tggacctggc caacgtctgg cggttcccct acctgtgcta caaaaatggt ggcggtgcct    420
tcctggtccc ctacctgctc ttcatggtca ttgctgggat gccactttc tacatggagc    480
tggccctcgg ccagttcaac agggaagggg ccgctggtgt ctggaagatc tgccccatac    540
tgaaaggtgt gggcttcacg gtcatcctca tctcactgta tgtcggcttc ttctacaacg    600
tcatcatcgc ctgggcgctg cactatctct ctcctccctt caccacggag ctcccctgga    660
tccactgcaa caactcctgg aacagcccca actgctcgga tgcccatcct ggtgactcca    720
gtggagacag ctcgggcctc aacgacactt ttgggaccac acctgctgcc gagtactttg    780
aacgtggcgt gctgcacctc caccagagcc atggcatcga cgacctgggg cctccgcggt    840
ggcagctcac agcctgcctg gtgctggtca tcgtgctgct ctacttcagc ctctggaagg    900
gcgtgaagac ctcagggaag gtggtatgga tcacagccac catgccatac gtggtcctca    960
ctgccctgct cctgcgtggg gtcacccctc ctggagccat agacggcatc agagcatacc   1020
tgagcgttga cttctaccgg ctctgcgagg cgtctgtttg gattgacgcg gccacccagg   1080
tgtgcttctc cctgggcgtg gggttcgggg tgctgatcgc cttctccagc tacaacaagt   1140
tcaccaacaa ctgctacagg gacgcgattg tcaccacctc catcaactcc ctgacgagct   1200
tctcctccgg cttcgtcgtc ttctccttcc tggggtacat ggcacagaag cacagtgtgc   1260
ccatcgggga cgtggccaag gacgggccag ggctgatctt catcatctac ccggaagcca   1320
tcgccacgct ccctctgtcc tcagcctggg ccgtggtctt cttcatcatg ctgctcaccc   1380
tgggtatcga cagcgccatg ggtggtatgg agtcagtgat caccgggctc atcgatgagt   1440
tccagctgct gcacagacac cgtgagctct tcacgctctt catcgtcctg gcgaccttcc   1500
tcctgtccct gttctgcgtc accaacggtg gcatctacgt cttcacgctc ctggaccatt   1560
ttgcagccgg cacgtccatc ctctttggag tgctcatcga agccatcgga gtggcctggt   1620
tctatggtgt tgggcagttc agcgacgaca tccagcagat gaccgggcag cggcccagcc   1680
tgtactggcg gctgtgctgg aagctggtca gcccctgctt tctcctgttc gtggtcgtgg   1740
tcagcattgt gaccttcaga ccccccact acggagccta catcttcccc gactgggcca   1800
acgcgctggg ctgggtcatc gccacatcct ccatggccat ggtgcccatc tatgcggcct   1860
acaagttctg cagcctgcct gggtcctttc gagagaaact ggcctacgcc attgcacccg   1920
agaaggaccg tgagctggtg gacagagggg aggtgcgcca gttcacgctc cgccactggc   1980
tcaaggtgta gaggagcag agacgaagac cccaggaagt catcctgcaa tgggagagac   2040
acgaacaaac caaggaaatc taagtttcga gagaaaggag ggcaacttct actcttcaac   2100
ctctactgaa aacacaaaca acaaagcaga agactcctct cttctgactg tttacacctt   2160
tccgtgccgg gagcgcacct cgccgtgtct tgtgttgctg taataacgac gtagatctgt   2220
```

```
gcagcgaggt ccaccccgtt gttgtccctg cagggcagaa aaacgtctaa cttcatgctg    2280
tctgtgtgag gctccctccc tcctgctcc ctgctcccgg ctctgaggct gccccagggg    2340
cactgtgttc tcaggcgggg atcacgatcc ttgtagacgc acctgctgag aatccccgtg    2400
ctcacagtag cttcctagac catttacttt gcccatatta aaaagccaag tgtcctgctt    2460
ggtttagctg tgcagaaggt gaaatggagg aaaccacaaa ttcatgcaaa gtcctttccc    2520
gatgcgtggc tcccagcaga ggccgtaaat tgagcgttca gttgacacat tgcacacaca    2580
gtctgttcag aggcattgga ggatgggggt cctggtatgt ctcaccagga aattctgttt    2640
atgttcttgc agcagagaga aataaaactc cttgaaacca gctcaggcta ctgccactca    2700
ggcagcctgt gggtccttgt ggtgtaggga acggcctgag aggagcgtgt cctatccccg    2760
gacgcatgca gggcccccac aggagcgtgt cctatccccg gacgcatgca gggcccccac    2820
aggagcatgt cctatccctg gacgcatgca gggcccccac aggagcgtgt actacccag    2880 aacgcatgca gggcccccac aggagcgtgt actacccag gacgcatgca gggcccccac    2940
tggagcgtgt actacccag gacgcatgca gggcccccac aggagcgtgt cctatccccg    3000
gaccggacgc atgcagggcc cccacaggag cgtgtactac cccaggacgc atgcagggcc    3060
cccacaggag cgtgtactac cccaggatgc atgcagggcc cccacaggag cgtgtactac    3120
cccaggacgc atgcagggcc cccatgcagg cagcctgcag accaacactc tgcctggcct    3180
tgagccgtga cctccaggaa gggaccccac tggaatttta tttctctcag gtgcgtgcca    3240
catcaataac aacagttttt atgtttgcga atggcttttt aaaatcatat ttacctgtga    3300
atcaaaacaa attcaagaat gcagtatccg cgagcctgct tgctgatatt gcagttttg    3360 tttacaagaa taattagcaa tactgagtga aggatgttgg ccaaaagctg ctttccatgg    3420
cacactgccc tctgccactg acaggaaagt ggatgccata gtttgaattc atgcctcaag    3480
tcggtgggcc tgcctacgtg ctgcccgagg cagggccg tgcagggcca gtcatggctg    3540
tcccctgcaa gtggacgtgg gctccaggga ctggagtgta atgctcggtg ggagccgtca    3600
gcctgtgaac tgccaggcag ctgcagttag cacagaggat ggcttcccca ttgccttctg    3660
gggagggaca cagaggacgg cttccccatc gccttctggc cgctgcagtc agcacagaga    3720
gcggcttccc cattgccttc tggggaggga cacagaggac agtttcccca tcgccttctg    3780
gttgttgaag acagcacaga gagcggcttc cccatcgcct tctggggagg ggctccgtgt    3840
agcaacccag gtgttgtccg tgtctgttga ccaatctcta ttcagcatcg tgtgggtccc    3900
taagcacaat aaaagacatc cacaatggaa aaaaaaaag gaattc              3946
```

<210> SEQ ID NO 42
<211> LENGTH: 620
<212> TYPE: PRT
<213> ORGANISM: Homo sapiens
<220> FEATURE:
<223> OTHER INFORMATION: DAT

<400> SEQUENCE: 42

Met Ser Lys Ser Lys Cys Ser Val Gly Leu Met Ser Ser Val Val Ala
 1               5                  10                  15

Pro Ala Lys Glu Pro Asn Ala Val Gly Pro Lys Glu Val Glu Leu Ile
            20                  25                  30

Leu Val Lys Glu Gln Asn Gly Val Gln Leu Thr Ser Ser Thr Leu Thr
        35                  40                  45

Asn Pro Arg Gln Ser Pro Val Glu Ala Gln Asp Arg Glu Thr Trp Gly
    50                  55                  60

```
Lys Lys Ile Asp Phe Leu Leu Ser Val Ile Gly Phe Ala Val Asp Leu
 65                  70                  75                  80

Ala Asn Val Trp Arg Phe Pro Tyr Leu Cys Tyr Lys Asn Gly Gly Gly
                 85                  90                  95

Ala Phe Leu Val Pro Tyr Leu Leu Phe Met Val Ile Ala Gly Met Pro
                100                 105                 110

Leu Phe Tyr Met Glu Leu Ala Leu Gly Gln Phe Asn Arg Glu Gly Ala
            115                 120                 125

Ala Gly Val Trp Lys Ile Cys Pro Ile Leu Lys Gly Val Gly Phe Thr
130                 135                 140

Val Ile Leu Ile Ser Leu Tyr Val Gly Phe Phe Tyr Asn Val Ile Ile
145                 150                 155                 160

Ala Trp Ala Leu His Tyr Leu Phe Ser Ser Phe Thr Thr Glu Leu Pro
                165                 170                 175

Trp Ile His Cys Asn Asn Ser Trp Asn Ser Pro Asn Cys Ser Asp Ala
                180                 185                 190

His Pro Gly Asp Ser Ser Gly Asp Ser Ser Gly Leu Asn Asp Thr Phe
            195                 200                 205

Gly Thr Thr Pro Ala Ala Glu Tyr Phe Glu Arg Gly Val Leu His Leu
            210                 215                 220

His Gln Ser His Gly Ile Asp Asp Leu Gly Pro Pro Arg Trp Gln Leu
225                 230                 235                 240

Thr Ala Cys Leu Val Leu Val Ile Val Leu Leu Tyr Phe Ser Leu Trp
                245                 250                 255

Lys Gly Val Lys Thr Ser Gly Lys Val Val Trp Ile Thr Ala Thr Met
                260                 265                 270

Pro Tyr Val Val Leu Thr Ala Leu Leu Leu Arg Gly Val Thr Leu Pro
            275                 280                 285

Gly Ala Ile Asp Gly Ile Arg Ala Tyr Leu Ser Val Asp Phe Tyr Arg
290                 295                 300

Leu Cys Glu Ala Ser Val Trp Ile Asp Ala Ala Thr Gln Val Cys Phe
305                 310                 315                 320

Ser Leu Gly Val Gly Phe Gly Val Leu Ile Ala Phe Ser Ser Tyr Asn
                325                 330                 335

Lys Phe Thr Asn Asn Cys Tyr Arg Asp Ala Ile Val Thr Thr Ser Ile
                340                 345                 350

Asn Ser Leu Thr Ser Phe Ser Ser Gly Phe Val Val Phe Ser Phe Leu
                355                 360                 365

Gly Tyr Met Ala Gln Lys His Ser Val Pro Ile Gly Asp Val Ala Lys
            370                 375                 380

Asp Gly Pro Gly Leu Ile Phe Ile Ile Tyr Pro Glu Ala Ile Ala Thr
385                 390                 395                 400

Leu Pro Leu Ser Ser Ala Trp Ala Val Val Phe Phe Ile Met Leu Leu
                405                 410                 415

Thr Leu Gly Ile Asp Ser Ala Met Gly Gly Met Glu Ser Val Ile Thr
                420                 425                 430

Gly Leu Ile Asp Glu Phe Gln Leu Leu His Arg His Arg Glu Leu Phe
            435                 440                 445

Thr Leu Phe Ile Val Leu Ala Thr Phe Leu Leu Ser Leu Phe Cys Val
            450                 455                 460

Thr Asn Gly Gly Ile Tyr Val Phe Thr Leu Leu Asp His Phe Ala Ala
465                 470                 475                 480

Gly Thr Ser Ile Leu Phe Gly Val Leu Ile Glu Ala Ile Gly Val Ala
```

```
                      485                 490                 495
Trp Phe Tyr Gly Val Gly Gln Phe Ser Asp Asp Ile Gln Gln Met Thr
                500                 505                 510

Gly Gln Arg Pro Ser Leu Tyr Trp Arg Leu Cys Trp Lys Leu Val Ser
            515                 520                 525

Pro Cys Phe Leu Leu Phe Val Val Val Ser Ile Val Thr Phe Arg
        530                 535                 540

Pro Pro His Tyr Gly Ala Tyr Ile Phe Pro Asp Trp Ala Asn Ala Leu
545                 550                 555                 560

Gly Trp Val Ile Ala Thr Ser Ser Met Ala Met Val Pro Ile Tyr Ala
                565                 570                 575

Ala Tyr Lys Phe Cys Ser Leu Pro Gly Ser Phe Arg Glu Lys Leu Ala
            580                 585                 590

Tyr Ala Ile Ala Pro Glu Lys Asp Arg Glu Leu Val Asp Arg Gly Glu
        595                 600                 605

Val Arg Gln Phe Thr Leu Arg His Trp Leu Lys Val
    610                 615                 620

<210> SEQ ID NO 43
<211> LENGTH: 2038
<212> TYPE: DNA
<213> ORGANISM: Mus musculus
<220> FEATURE:
<223> OTHER INFORMATION: ADH2

<400> SEQUENCE: 43
aatttgctga gcctgtcacc tgtgttccag gagccaaacc agcaatgtct tcgcctgcac      60
aacctcgagt ccctgcccca ctggccgact tgaagattca ataccaag atcttcataa      120 acaatgaatg gcacaattca gtgagcggca agaaatttcc agttcttaac cctgcaactg      180
aggaggtcat ctgccacgtg aagaaggg acaaggctga tgttgacaaa gctgtgaagg      240
ctgcaagaca ggctttccag attggctctc catggcgcac catggatgct tcagagaggg      300
gctgcctgct gaacaagctg gctgacttaa tggagagaga tcgtctgctg ctagctacaa      360
tggaggcact caatggtggg aaagtctttg ccaatgcata cttgtcggat ttaggaggct      420
gcataaaagc attaaagtac tgtgcaggct gggctgacaa gattcatggt caaacaatac      480
caagtgatgg agacattttc acttatacaa gacgtgaacc tattggagtg tgtggccaaa      540
tcatcccctg gaattttcca atgctcatgt tcatttggaa gataggccct gcccttagct      600
gtgggaatac cgtggttgtc aagccagcag agcaaactcc tctcacggct cttcacctgg      660
catctttaat aaaagaggca gggtttcctc ctggcgtggt aaacattgtc cctggttatg      720
ggccaactgc aggggcagcc atctcctctc acatggatgt cgacaaggtg gccttcactg      780
gatcaacaca ggttggcaag ttaatcaagg aagctgcagg aaaagcaat ctgaagagag      840 tcaccctgga gcttggggga agagcccttt gcattgtgtt tgcagatgcc gacttggaca      900
ttgctgttga gtttgcacac catggagtgt tttatcatca aggccaatgc tgtgtcgcag      960
catcccggat ttttgttgag gagtcagttt atgatgagtt tgtgaaaagg agtgttgagc      1020
gagctaagaa atatgttctt ggaaatcctc tgaccccagg aataaatcaa ggccctcaga      1080
ttgacaagga acaacatgat aaaatactcg atctcattga gagtgggaag aaagaaggag      1140
ccaaactgga gtgtggtgga ggacgctggg ggaacaaagg cttctttgtg cagcccacag      1200
tgttctccaa cgtgactgat gagatgcgca ttgccaaaga ggagatattt ggaccagtgc      1260
aacaaatcat gaagtttaag tctgtagatg atgtgatcaa gagagcaaac aatactaccct      1320
```

-continued

```
atggtttagc agcaggactc ttcactaaag acctggataa ggccatcact gtgtcatctg    1380
ctctgcaggc tggggtggtg tgggttaact gctatatcat gttgtcagcc cagtgcccct    1440
tcggtggatt caagatgtct ggaaatggaa gagaactggg tgaacatggt ctttatgaat    1500
acactgagct caagacagtc gcaatgaaga tatctcagaa gaactcctaa agaagccagc    1560
agagtaaaga gaaactctca gcagtggtac acatctccta tagtaaccag catagtcgtg    1620
tttattata atttcttctc cagttgattt cttaagcaaa aggaattcat cagtgttact    1680
gtcactcata aaaaaacatg tggcttaatc caacagattc attcaccttc taatatgtga    1740
ccccagttct tatccaagaa tagaaggata gatataacgg caagctctct gtaactccgt    1800
catgaccagg tgctttccat tgtagctact tatctaacat actcatttgg tgaggaggac    1860
tagttgtgac ttaagctctg tccctcagtg actccttgaa gtactcacca cacataatga    1920
ctgcagagtc agctgctctg ttccccaggt gttgtgaaat attttctaga atgtcatgcc    1980
tgcttgtcaa atgaaatgcc tagctgtaat tagaacgcaa agcttaataa aggcaccc     2038
```

<210> SEQ ID NO 44
<211> LENGTH: 501
<212> TYPE: PRT
<213> ORGANISM: Mus musculus
<220> FEATURE:
<223> OTHER INFORMATION: ADH2

<400> SEQUENCE: 44

```
Met Ser Ser Pro Ala Gln Pro Arg Val Pro Ala Pro Leu Ala Asp Leu
  1               5                  10                  15

Lys Ile Gln His Thr Lys Ile Phe Ile Asn Asn Glu Trp His Asn Ser
             20                  25                  30

Val Ser Gly Lys Lys Phe Pro Val Leu Asn Pro Ala Thr Glu Glu Val
         35                  40                  45

Ile Cys His Val Glu Glu Gly Asp Lys Ala Asp Val Asp Lys Ala Val
     50                  55                  60

Lys Ala Ala Arg Gln Ala Phe Gln Ile Gly Ser Pro Trp Arg Thr Met
 65                  70                  75                  80

Asp Ala Ser Glu Arg Gly Cys Leu Leu Asn Lys Leu Ala Asp Leu Met
                 85                  90                  95

Glu Arg Asp Arg Leu Leu Leu Ala Thr Met Glu Ala Leu Asn Gly Gly
            100                 105                 110

Lys Val Phe Ala Asn Ala Tyr Leu Ser Asp Leu Gly Gly Cys Ile Lys
        115                 120                 125

Ala Leu Lys Tyr Cys Ala Gly Trp Ala Asp Lys Ile His Gly Gln Thr
    130                 135                 140

Ile Pro Ser Asp Gly Asp Ile Phe Thr Tyr Thr Arg Arg Glu Pro Ile
145                 150                 155                 160

Gly Val Cys Gly Gln Ile Ile Pro Trp Asn Phe Pro Met Leu Met Phe
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Leu Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Val Asp
225                 230                 235                 240

Lys Val Ala Phe Thr Gly Ser Thr Gln Val Gly Lys Leu Ile Lys Glu
```

```
                245                 250                 255
Ala Ala Gly Lys Ser Asn Leu Lys Arg Val Thr Leu Glu Leu Gly Gly
            260                 265                 270

Lys Ser Pro Cys Ile Val Phe Ala Asp Ala Asp Leu Asp Ile Ala Val
        275                 280                 285

Glu Phe Ala His His Gly Val Phe Tyr His Gln Gly Gln Cys Cys Val
    290                 295                 300

Ala Ala Ser Arg Ile Phe Val Glu Glu Ser Val Tyr Asp Glu Phe Val
305                 310                 315                 320

Lys Arg Ser Val Glu Arg Ala Lys Lys Tyr Val Leu Gly Asn Pro Leu
                325                 330                 335

Thr Pro Gly Ile Asn Gln Gly Pro Gln Ile Asp Lys Glu Gln His Asp
            340                 345                 350

Lys Ile Leu Asp Leu Ile Glu Ser Gly Lys Lys Glu Gly Ala Lys Leu
        355                 360                 365

Glu Cys Gly Gly Gly Arg Trp Gly Asn Lys Gly Phe Phe Val Gln Pro
    370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Val Asp Asp
                405                 410                 415

Val Ile Lys Arg Ala Asn Asn Thr Thr Tyr Gly Leu Ala Ala Gly Leu
            420                 425                 430

Phe Thr Lys Asp Leu Asp Lys Ala Ile Thr Val Ser Ser Ala Leu Gln
        435                 440                 445

Ala Gly Val Val Trp Val Asn Cys Tyr Ile Met Leu Ser Ala Gln Cys
    450                 455                 460

Pro Phe Gly Gly Phe Lys Met Ser Gly Asn Gly Arg Glu Leu Gly Glu
465                 470                 475                 480

His Gly Leu Tyr Glu Tyr Thr Glu Leu Lys Thr Val Ala Met Lys Ile
                485                 490                 495

Ser Gln Lys Asn Ser
            500

<210> SEQ ID NO 45
<211> LENGTH: 2116
<212> TYPE: DNA
<213> ORGANISM: Homo sapiens
<220> FEATURE:
<223> OTHER INFORMATION: ADH2

<400> SEQUENCE: 45
atcagaacca aattgctgag ccagtcacct gtgttccagg agccgaatca gaaatgtcat      60
cctcaggcac gccagactta cctgtcctac tcaccgattt gaagattcaa tatactaaga    120
tcttcataaa caatgaatgg catgattcag tgagtggcaa gaaatttcct gtctttaatc    180
ctgcaactga ggaggagctc tgccaggtag aagaaggaga taggaggat gttgacaagg    240 cagtgaaggc cgcaagacag cttttcaga ttggatcccc gtggcgtact atggatgctt    300
ccgagagggg gcgactatta tacaagttgg ctgatttaat cgaaagagat cgtctgctgc    360
tggcgacaat ggagtcaatg aatggtggaa aactctattc caatgcatat ctgaatgatt    420
tagcaggctg catcaaaaca ttgcgctact gtgcaggttg ggctgacaag atccagggcc    480
gtacaatacc aattgatgga aattttttta catatacaag acatgaacct attggtgtat    540
gtggccaaat cattccttgg aatttcccgt tggttatgct catttggaag ataggcctg    600
```

```
cactgagctg tggaaacaca gtggttgtca aaccagcaga gcaaactcct ctcactgctc    660
tccacgtggc atctttaata aaagaggcag ggtttcctcc tggagtagtg aatattgttc    720
ctggttatgg gcctacagca ggggcagcca tttcttctca catggatata gacaaagtag    780
ccttcacagg atcaacagag gttggcaagt tgatcaaaga agctgccggg aaaagcaatc    840
tgaagagggt gaccctggag cttggaggaa agagcccttg cattgtgtta gctgatgccg    900
acttggacaa tgctgttgaa tttgcacacc atggggtatt ctaccaccag gccagtgtt    960
gtatagccgc atccaggatt tttgtggaag aatcaattta tgatgagttt gttcgaagga   1020
gtgttgagcg ggctaagaag tatatccttg gaaatcctct gaccccagga gtcactcaag   1080
gccctcagat tgacaaggaa caatatgata aaatacttga cctcattgag agtgggaaga   1140
aagaagggc caaactggaa tgtggaggag gcccgtgggg gaataaaggc tactttgtcc   1200
agcccacagt gttctctaat gttacagatg agatgcgcat tgccaaagag gagattttg   1260
gaccagtgca gcaaatcatg aagtttaaat ctttagatga cgtgatcaaa agagcaaaca   1320
atactttcta tggcttatca gcaggagtgt ttaccaaaga cattgataaa gccataacaa   1380
tctcctctgc tctgcaggca ggaacagtgt gggtgaattg ctatggcgtg gtaagtgccc   1440
agtgccccct tggtggattc aagatgtctg gaaatggaag agaactggga gagtacggtt   1500
tccatgaata tacagaggtc aaaacagtca cagtgaaaat ctctcagaag aactcataaa   1560
gaaaatacaa gagtggagag aagctcttca atagctaagc atctccttac agtcactaat   1620
atagtagatt ttaaagacaa aattttttct ttccttgattt ttttaaacat aagctaaatc   1680
atattagtat taatactacc catagaaaac ttgacatgta gcttcttctg aaagaattat   1740
ttgccttctg aaatgtgacc cccaagtcct atcctaaata aaaaaagaca aattcggatg   1800
tatgatctct ctagctttgt catagttatg tgatttttcct ttgtagctac ttttgcagga   1860
taataatttt atagaaaagg aacagttgca tttagcttct ttcccttagt gactcttgaa   1920
gtacttaaca tacacgttaa ctgcagagta aattgctctg ttcccagtag ttataaagtc   1980
cttggactgt tttgaaaagt ttcctaggat gtcatgtctg cttgtcaaaa gaaataatcc   2040
ctgtaatatt tagctgtaaa ctgaatataa agcttaataa aaacaacctt gcatgaaaaa   2100
aaaaaaaaaa aaaaaa                                                  2116
```

<210> SEQ ID NO 46
<211> LENGTH: 501
<212> TYPE: PRT
<213> ORGANISM: Homo sapiens
<220> FEATURE:
<223> OTHER INFORMATION: ADH2

<400> SEQUENCE: 46

```
Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95
```

-continued

```
Glu Arg Asp Arg Leu Leu Leu Ala Thr Met Glu Ser Met Asn Gly Gly
                100                 105                 110
Lys Leu Tyr Ser Asn Ala Tyr Leu Asn Asp Leu Ala Gly Cys Ile Lys
            115                 120                 125
Thr Leu Arg Tyr Cys Ala Gly Trp Ala Asp Lys Ile Gln Gly Arg Thr
        130                 135                 140
Ile Pro Ile Asp Gly Asn Phe Phe Thr Tyr Thr Arg His Glu Pro Ile
145                 150                 155                 160
Gly Val Cys Gly Gln Ile Ile Pro Trp Asn Phe Pro Leu Val Met Leu
                165                 170                 175
Ile Trp Lys Ile Gly Pro Ala Leu Ser Cys Gly Asn Thr Val Val Val
            180                 185                 190
Lys Pro Ala Glu Gln Thr Pro Leu Thr Ala Leu His Val Ala Ser Leu
        195                 200                 205
Ile Lys Glu Ala Gly Phe Pro Pro Gly Val Val Asn Ile Val Pro Gly
210                 215                 220
Tyr Gly Pro Thr Ala Gly Ala Ala Ile Ser Ser His Met Asp Ile Asp
225                 230                 235                 240
Lys Val Ala Phe Thr Gly Ser Thr Glu Val Gly Lys Leu Ile Lys Glu
                245                 250                 255
Ala Ala Gly Lys Ser Asn Leu Lys Arg Val Thr Leu Glu Leu Gly Gly
            260                 265                 270
Lys Ser Pro Cys Ile Val Leu Ala Asp Ala Asp Leu Asp Asn Ala Val
        275                 280                 285
Glu Phe Ala His His Gly Val Phe Tyr His Gln Gly Gln Cys Cys Ile
290                 295                 300
Ala Ala Ser Arg Ile Phe Val Glu Glu Ser Ile Tyr Asp Glu Phe Val
305                 310                 315                 320
Arg Arg Ser Val Glu Arg Ala Lys Lys Tyr Ile Leu Gly Asn Pro Leu
                325                 330                 335
Thr Pro Gly Val Thr Gln Gly Pro Gln Ile Asp Lys Glu Gln Tyr Asp
            340                 345                 350
Lys Ile Leu Asp Leu Ile Glu Ser Gly Lys Lys Glu Gly Ala Lys Leu
        355                 360                 365
Glu Cys Gly Gly Gly Pro Trp Gly Asn Lys Gly Tyr Phe Val Gln Pro
370                 375                 380
Thr Val Phe Ser Asn Val Thr Asp Glu Met Arg Ile Ala Lys Glu Glu
385                 390                 395                 400
Ile Phe Gly Pro Val Gln Gln Ile Met Lys Phe Lys Ser Leu Asp Asp
                405                 410                 415
Val Ile Lys Arg Ala Asn Asn Thr Phe Tyr Gly Leu Ser Ala Gly Val
            420                 425                 430
Phe Thr Lys Asp Ile Asp Lys Ala Ile Thr Ile Ser Ser Ala Leu Gln
        435                 440                 445
Ala Gly Thr Val Trp Val Asn Cys Tyr Gly Val Val Ser Ala Gln Cys
450                 455                 460
Pro Phe Gly Gly Phe Lys Met Ser Gly Asn Gly Arg Glu Leu Gly Glu
465                 470                 475                 480
Tyr Gly Phe His Glu Tyr Thr Glu Val Lys Thr Val Thr Val Lys Ile
                485                 490                 495
Ser Gln Lys Asn Ser
            500
```

SPECIFIC MARKER LMX1A ON DOPAMINERGIC NEURONS

CROSS REFERENCE TO RELATED APPLICATIONS

This application is a division of U.S. application Ser. No. 10/580,989, filed Mar. 29, 2007, which is a U.S. National Phase of PCT/JP2004/017574, filed Nov. 26, 2004, which claims priority to Japanese Application No. 2003-395493, filed Nov. 26, 2003.

REFERENCE TO A SEQUENCE LISTING

This application includes a Sequence Listing as a text file named "-81-1.txt" created Mar. 13, 2012, and containing 114,688 bytes. The material contained in this text file is incorporated by reference in its entirety for all purposes.

TECHNICAL FIELD

The present invention relates to Lmx1a genes, which are specifically expressed in dopaminergic neurons. Dopaminergic neurons and their progenitor cells are used in transplantation therapy for neurodegenerative diseases such as Parkinson's disease (PD), and can be efficiently isolated by detecting the expression of a Lmx1a gene or a protein encoded by the gene.

BACKGROUND ART

The dopamine system is an extremely important system for essential regulation of locomotion, hormone secretion, emotions and such in the mammalian brain. Thus, abnormalities in dopaminergic neural transmission cause various neural disorders. For example, Parkinson's disease (PD) is a neurodegenerative disease of the extrapyramidal system that occurs due to specific degeneration of dopaminergic neurons in the substantia nigra of the midbrain (Harrison's Principles of Internal Medicine, Vol. 2, 23rd edition, Isselbacher et al., ed., McGraw-Hill Inc., NY (1994), pp. 2275-7). Oral administration of L-DOPA (3,4-dihydroxyphenylalanine) is performed as a primary therapeutic method for Parkinson's disease to compensate for the decrease in the amount of dopamine produced; however, the duration of the effect is known to be unsatisfactory.

Therapeutic methods have been attempted whereby the midbrain ventral regions of 6- to 9-week old aborted fetuses, which contain dopaminergic neuron progenitor cells, are transplanted to compensate for the loss of dopaminergic neurons (U.S. Pat. No. 5,690,927; Spencer et al. (1992) N. Engl. J. Med. 327: 1541-8; Freed et al. (1992) N. Engl. J. Med. 327: 1549-55; Widner et al. (1992) N. Engl. J. Med. 327: 1556-63; Kordower et al. (1995) N. Engl. J. Med. 332: 1118-24; Defer et al. (1996) Brain 119: 41-50; Lopez-Lozano et al. (1997) Transp. Proc. 29: 977-80). However, these methods currently present problems relating to cell supply and ethics (Rosenstain (1995) Exp. Neurol. 33: 106; Turner et al. (1993) Neurosurg. 33: 1031-7). Also, various problems are being pointed out, such as the risk of infection and contamination, immunological rejection of transplants (Lopez-Lozano et al. (1997) Transp. Proc. 29: 977-980; Widner and Brudin (1988) Brain Res. Rev. 13: 287-324), and low survival rates due to the primary dependence of fetal tissues on lipid metabolism rather than glycolysis (Rosenstein (1995) Exp. Neurol. 33: 106).

In order to resolve ethical issues and the shortage of supply, methods have been proposed that use, for example, porcine cortex, stria, and midbrain cells (for example, Japanese Patent Kohyo Publication No. (JP-A) H10-508487, JP-A H10-508488 or JP-A H10-509034). In these methods, a complex procedure involving the alteration of cell surface antigens (MHC class I antigens) is required to suppress rejection. Methods involving local immunosuppression by the simultaneous transplantation of Sertoli's cells have been proposed as a method for eliminating transplant rejection (JP-A H11-509170, JP-A H11-501818, Selawry and Cameron (1993) Cell Transplant 2: 123-9). It is possible to obtain transplant cells from relatives with matching MHCs, bone marrow from other individuals, bone marrow banks, or umbilical cord-blood banks. However, if it were possible to use the patient's own cells, the problem of rejection reactions could be overcome without any laborious procedures or trouble.

Therefore, instead of using cells from aborted fetuses as transplant materials, the use of dopaminergic neurons differentiated in vitro from non-neural cells such as embryonic stem (ES) cells and bone marrow interstitial cells is considered to be promising. In fact, functional dopaminergic neurons were reported to have been formed upon transplanting ES cells to lesion stria of a rat Parkinson's disease model (Kim et al. (2002) Nature 418: 50-56). It is believed that regenerative therapy from ES cells or a patient's own nerve stem cells will be increasingly important in the future.

In the treatment of nerve tissue damage, brain function must be reconstructed, and in order to form suitable links with surrounding cells (network formation), it is necessary to transplant immature cells, which can differentiate in vivo into neurons. When transplanting neuron progenitor cells, in addition to the aforementioned problem regarding supply, there is also the possibility that the progenitor cells will differentiate into groups of heterogeneous cells. For example, in treating Parkinson's disease, it is necessary to selectively transplant catecholamine-containing neurons that produce dopamine. Examples of transplant cells proposed in the past for use in the treatment of Parkinson's disease include striatum (Lindvall et al. (1989) Arch. Neurol. 46: 615-31; Widner et al. (1992) N. Engl. J. Med. 327: 1556-63), immortalized cell lines derived from human fetal neurons (JP-A H08-509215; JP-A H11-506930; JP-A No. 2002-522070), human postmitotic neurons derived from NT2Z cells (JP-A H09-5050554), primordial neuron cells (JP-A H11-509729), cells and bone marrow stroma cells transfected with exogenous genes so as to produce catecholamines such as dopamines (JP-A 2002-504503; JP-A 2002-513545), and genetically engineered ES cells (Kim et al. (2002) Nature 418: 50-56). However, none of these contain only dopaminergic neurons or cells that differentiate into dopaminergic cells.

A method has been proposed for selectively concentrating and isolating dopaminergic neurons from undifferentiated cell populations. In this method, a reporter gene expressing a fluorescent protein is introduced into each cell of a cell population, under the control of a gene promoter/enhancer, such as the tyrosine hydroxylase (TH) expressed in dopaminergic neurons. Fluorescing cells are then isolated. The dopaminergic neurons are visualized in their viable state, and concentrated, isolated, and identified (Japanese Patent Application Kokai Publication No. (JP-A) 2002-51775 (unexamined, published Japanese patent application)). This method requires the complicated step of introducing an exogenous gene. Further, the presence of a reporter gene poses problems of toxicity and immunogenicity when used in conjunction with gene therapy.

Lmx1a was identified as a LIM-type homeobox gene expressed in the roof plate of the developing spinal cord (the organizer region which secretes differentiation-inducing factors in the most dorsal region; neurons do not develop from this region), the neural crest, the hindbrain rhombic lip, and the posterior region of the developing cerebral hemisphere (Non-Patent Documents 1 and 2). In dreher mutant mice, which are animal models for type II agyria, autosomal recessive mutations have been revealed to occur on Lmx1a (Non-Patent Document 1). Furthermore, it is also known that mutations in Lmx1a trigger lesions in the central nervous system in queue courte (qc) rats (Non-Patent Documents 3 to 5). The Lmx1a gene is expressed not only during the fetal phase but also after birth, and contributes to the formation of the cerebral cortex and the cerebellum.

Non-Patent Document 1: Millonig et al. (2000) Nature 403: 764-769
Non-Patent Document 2: Failli et al. (2002) Mechanisms of Development 118 (1-2): 225-228
Non-Patent Document 3: Kitada et al. (2001) 2001 Meeting on Physiological Genomics and Rat Models
Non-Patent Document 4: Kitada et al. (2001) The 15$^{th}$ International Mouse Genome Conference
Non-Patent Document 5: Kitada et al. (2000) Record of the 17$^{th}$ Meeting of the Japanese Society of Animal Models for Human Diseases

DISCLOSURE OF THE INVENTION

Problems to be Solved by the Invention

One of the major current problems in Parkinson's disease (PD) transplantation therapy is that dopaminergic neuron progenitor cells which are induced to differentiate, as well as the midbrain ventral region of aborted fetuses, are both mixtures of a myriad of cell types. When considering safety in neural circuit formation, it is preferable to use isolated cells that comprise only the cell type of interest. Furthermore, when considering the risk of tumorigenesis, it is believed preferable to use isolated postmitotic neurons. Moreover, when considering the survival of cells at their transplantation site in the brain, and their ability to properly form networks, it is expected that therapeutic effects can be further improved by isolating progenitor cells at the earliest stage possible. Therefore, the inventors of the present invention aimed to isolate genes specific to dopaminergic neuron progenitor cells. As a result, they successfully isolated Lrp4 (WO 2004/065599) and the novel gene 65B13 (WO 2004/038018), which are genes transiently expressed in neuron progenitor cells immediately before and after cell cycle exit.

Means to Solve the Problems

In order to isolate genes specific to dopaminergic neuron progenitor cells, a gene specifically expressed in the most ventral region of the E12.5 murine midbrain containing dopaminergic neurons was identified using a modification ("Method for Homogenizing the Amounts of DNA Fragments and Subtraction Method", WO 02/103007) of the subtraction method (N-RDA: Representational Difference Analysis; RDA (Listsyn N. A. (1995) Trends Genet. 11: 303-7), by additionally dividing the ventral region into two regions in the dorsoventral direction. One of the isolated fragments was a cDNA fragment encoding Lmx1a. Hitherto, Lmx1a has been reported as being expressed in the hippocampus, the cerebellum, and the most dorsal side of the roof plate region covering the diencephalon to the spinal cord. However, Lmx1a expression was not known to be specific to dopaminergic neurons.

Lmx1a expression was maintained from the stages of proliferating progenitor cells to cells after cell cycle exit and even in adults. In this way, Lmx1a showed an expression pattern that differed from known markers. In particular, it possesses the characteristics of genes expressed from the stage of proliferating progenitor cells. For this reason, it was considered to be a useful marker for detecting dopaminergic neurons including proliferating progenitor cells. Also, by its combined use with known markers, Lmx1a enabled sorting of proliferating progenitor cells and postmitotic precursor cells. Thus in this way the present invention was expected to be an effective marker, particularly when screening for differentiation-inducing reagents for dopaminergic neurons. Further, Lmx1a is a marker expressed at an earlier stage than known markers, and this also contributes to the above expectation.

Specifically, the present invention provides:
[1] a method for detecting or selecting a dopaminergic neuron and/or a progenitor cell thereof, wherein the method comprises the step of contacting a cellular sample potentially comprising a dopaminergic neuron and/or a progenitor cell thereof with a polynucleotide that hybridizes under stringent conditions to a transcript of a gene that consists of a nucleotide sequence of any one of (1) to (6):
(1) the nucleotide sequence of SEQ ID NO: 13;
(2) a nucleotide sequence encoding a polypeptide consisting of the amino acid sequence of SEQ ID NO: 14;
(3) a nucleotide sequence that hybridizes under stringent conditions to a gene consisting of the nucleotide sequence of SEQ ID NO: 13;
(4) the nucleotide sequence of SEQ ID NO: 15 or 17;
(5) a nucleotide sequence encoding a polypeptide consisting of the amino acid sequence of SEQ ID NO: 16 or 18; and
(6) a nucleotide sequence that hybridizes under stringent conditions to a gene consisting of the nucleotide sequence of SEQ ID NO: 15 or 17;
[2] the method of [1], wherein the polynucleotide comprises at least 15 nucleotides;
[3] a reagent for distinguishing a dopaminergic neuron and/or a progenitor cell thereof, wherein the reagent comprises, as an active ingredient, a polynucleotide that hybridizes under stringent conditions to a transcript of a gene that consists of a nucleotide sequence of any one of (1) to (6):
(1) the nucleotide sequence of SEQ ID NO: 13;
(2) a nucleotide sequence encoding a polypeptide consisting of the amino acid sequence of SEQ ID NO: 14;
(3) a nucleotide sequence that hybridizes under stringent conditions to a gene consisting of the nucleotide sequence of SEQ ID NO: 13;
(4) the nucleotide sequence of SEQ ID NO: 15 or 17;
(5) a nucleotide sequence encoding a polypeptide consisting of the amino acid sequence of SEQ ID NO: 16 or 18; and
(6) a nucleotide sequence that hybridizes under stringent conditions to a gene consisting of the nucleotide sequence of SEQ ID NO: 15 or 17;
[4] the reagent of [3], wherein the polynucleotide comprises at least 15 nucleotides;
[5] a method for detecting or selecting a dopaminergic neuron and/or a progenitor cell thereof, wherein the method comprises the step of contacting a cellular sample potentially comprising a dopaminergic neuron and/or a progenitor cell thereof with an antibody that binds to a polypeptide that consists of an amino acid sequence of any one of (1) to (6) or a partial sequence thereof:

(1) the amino acid sequence of SEQ ID NO: 14;
(2) an amino acid sequence with a deletion, insertion, substitution, or addition of one or more amino acids in the amino acid sequence of SEQ ID NO: 14;
(3) an amino acid sequence encoded by a nucleotide sequence that hybridizes under stringent conditions to a gene consisting of the nucleotide sequence of SEQ ID NO: 13;
(4) the amino acid sequence of SEQ ID NO: 16 or 18;
(5) an amino acid sequence with a deletion, insertion, substitution, or addition of one or more amino acids in the amino acid sequence of SEQ ID NO: 16 or 18; and
(6) an amino acid sequence encoded by a nucleotide sequence that hybridizes under stringent conditions to a gene consisting of the nucleotide sequence of SEQ ID NO: 15 or 17;
[6] the method of [5], wherein the polypeptide consisting of a partial sequence comprises at least six consecutive amino acid residues;
[7] a reagent for distinguishing a dopaminergic neuron and/or a progenitor cell thereof wherein the reagent comprises, as an active ingredient, an antibody that binds to a polypeptide that consists of an amino acid sequence of any one of (1) to (6) or a partial sequence thereof:
(1) the amino acid sequence of SEQ ID NO: 14;
(2) an amino acid sequence with a deletion, insertion, substitution, or addition of one or more amino acids in the amino acid sequence of SEQ ID NO: 14;
(3) an amino acid sequence encoded by a nucleotide sequence that hybridizes under stringent conditions to a gene consisting of the nucleotide sequence of SEQ ID NO: 13;
(4) the amino acid sequence of SEQ ID NO: 16 or 18;
(5) an amino acid sequence with a deletion, insertion, substitution, or addition of one or more amino acids in the amino acid sequence of SEQ ID NO: 16 or 18; and
(6) an amino acid sequence encoded by a nucleotide sequence that hybridizes under stringent conditions to a gene consisting of the nucleotide sequence of SEQ ID NO: 15 or 17;
[8] the reagent of [7], wherein the polypeptide consisting of a partial sequence comprises at least six consecutive amino acid residues;
[9] a method for detecting or selecting a dopaminergic neuron and/or a progenitor cell thereof, wherein the method comprises the steps of:
(a) contacting a cellular sample potentially comprising a dopaminergic neuron and/or a progenitor cell thereof with a polynucleotide that hybridizes under stringent conditions to a transcript of a gene that consists of a nucleotide sequence from any one of (a-1) to (a-6):
    (a-1) the nucleotide sequence of SEQ ID NO: 13;
    (a-2) a nucleotide sequence encoding a polypeptide consisting of the amino acid sequence of SEQ ID NO: 14;
    (a-3) a nucleotide sequence that hybridizes under stringent conditions to a gene consisting of the nucleotide sequence of SEQ ID NO: 13;
    (a-4) the nucleotide sequence of SEQ ID NO: 15 or 17;
    (a-5) the nucleotide sequence encoding a polypeptide consisting of the amino acid sequence of SEQ ID NO: 16 or 18; and
    (a-6) a nucleotide sequence that hybridizes under stringent conditions to a gene consisting of the nucleotide sequence of SEQ ID NO: 15 or 17; and
(b) contacting a cellular sample potentially comprising a dopaminergic neuron and/or a progenitor cell thereof with a polynucleotide that hybridizes under stringent conditions to transcripts of one or more genes selected from the group consisting of Lmx1b, Nurr1, En1, Ptx3, and TH, or with an antibody that binds to translation products of said selected genes;

[10] the method of [9], which further comprises the step of:
(c) contacting a cellular sample potentially comprising the dopaminergic neuron and/or the progenitor cell thereof with a polynucleotide that hybridizes under stringent conditions to transcripts of either or both of the genes selected from DAT and ADH2 or with an antibody that binds to a translation product of a said selected gene;
[11] the method of [9], wherein the gene selected in step (b) is one or more of Lmx1b, Nurr1, or En1;
[12] a method for detecting or selecting a dopaminergic neuron and/or a progenitor cell thereof, wherein the method comprises the steps of:
(a) contacting a cellular sample potentially comprising a dopaminergic neuron and/or a progenitor cell thereof with a polynucleotide that hybridizes under stringent conditions to a transcript of a gene that consists of a nucleotide sequence from any one of (a-1) to (a-6):
    (a-1) the nucleotide sequence of SEQ ID NO: 13;
    (a-2) a nucleotide sequence encoding a polypeptide consisting of the amino acid sequence of SEQ ID NO: 14;
    (a-3) a nucleotide sequence that hybridizes under stringent conditions to a gene consisting of the nucleotide sequence of SEQ ID NO: 13;
    (a-4) the nucleotide sequence of SEQ ID NO: 15 or 17;
    (a-5) a nucleotide sequence encoding a polypeptide consisting of the amino acid sequence (human) of SEQ ID NO: 16 or 18; and
    (a-6) a nucleotide sequence that hybridizes under stringent conditions to a gene consisting of the nucleotide sequence of SEQ ID NO: 15 or 17; and
(b) contacting a cellular sample potentially comprising a dopaminergic neuron and/or a progenitor cell thereof with a polynucleotide that hybridizes under stringent conditions to transcripts of either or both of the genes selected from DAT and ADH2, or with an antibody that binds to translation products of said selected genes;
[13] the method of any one of [9] to [12], wherein the polynucleotide is a nucleotide sequence comprising at least 15 consecutive nucleotides;
[14] a kit for distinguishing a dopaminergic neuron and/or a progenitor cell thereof, wherein the kit comprises: the reagent of [3] or [4]; and a polynucleotide that hybridizes under stringent conditions to transcripts of one or more genes selected from the group consisting of Lmx1b, Nurr1, En1, Ptx3, TH, DAT, and ADH2;
[15] a kit for distinguishing a dopaminergic neuron and/or a progenitor cell thereof, wherein the kit comprises: the reagent of [3] or [4]; and an antibody that binds to translation products of one or more genes selected from the group consisting of Lmx1b, Nurr1, En1, Ptx3, TH, DAT, and ADH2;
[16] a method for detecting or selecting a dopaminergic neuron and/or a progenitor cell thereof, wherein the method comprises the steps of:
(a) contacting a cellular sample potentially comprising a dopaminergic neuron and/or a progenitor cell thereof with an antibody that binds to a polypeptide consisting of an amino acid sequence of any one of (a-1) to (a-6) or a partial sequence thereof:
    (a-1) the amino acid sequence of SEQ ID NO: 14;
    (a-2) an amino acid sequence with a deletion, insertion, substitution, or addition of one or more amino acids in the amino acid sequence of SEQ ID NO: 14;
    (a-3) an amino acid sequence encoded by a nucleotide sequence that hybridizes under stringent conditions to a gene consisting of the nucleotide sequence of SEQ ID NO: 13;
    (a-4) the amino acid sequence of SEQ ID NO: 16 or 18;

(a-5) an amino acid sequence with a deletion, insertion, substitution, or addition of one or more amino acids in the amino acid sequence of SEQ ID NO: 16 or 18; and (a-6) an amino acid sequence encoded by a nucleotide sequence that hybridizes under stringent conditions to a gene consisting of the nucleotide sequence of SEQ ID NO: 15 or 17; and (b) contacting a cellular sample potentially comprising a dopaminergic neuron and/or a progenitor cell thereof with a polynucleotide that hybridizes under stringent conditions to transcripts of one or more genes selected from the group consisting of Lmx1b, Nurr1, En1, Ptx3, and TH, or with an antibody that binds to translation products of said selected genes;

[17] the method of [16], which further comprises the step of:
(c) contacting a cellular sample potentially comprising a dopaminergic neuron and/or a progenitor cell thereof with a polynucleotide that hybridizes under stringent conditions to transcripts of either or both of the genes selected from DAT and ADH2 or with an antibody that binds to translation products of said selected genes;

[18] the method of [16], wherein the genes selected in step (b) is one or more of Lmx1b, Nurr1, or En1;

[19] a method for detecting or selecting a dopaminergic neuron and/or a progenitor cell thereof, wherein the method comprises the steps of:
(a) contacting a cellular sample potentially comprising a dopaminergic neuron and/or a progenitor cell thereof with an antibody that binds to a polypeptide consisting of an amino acid sequence of any one of (a-1) to (a-6) or a partial sequence thereof:
    (a-1) the amino acid sequence of SEQ ID NO: 14;
    (a-2) an amino acid sequence with a deletion, insertion, substitution, or addition of one or more amino acids in the amino acid sequence of SEQ ID NO: 14;
    (a-3) an amino acid sequence encoded by a nucleotide sequence that hybridizes under stringent conditions to a gene consisting of the nucleotide sequence of SEQ ID NO: 13;
    (a-4) the amino acid sequence of SEQ ID NO: 16 or 18;
    (a-5) an amino acid sequence with a deletion, insertion, substitution, or addition of one or more amino acids in the amino acid sequence of SEQ ID NO: 16 or 18; and
    (a-6) an amino acid sequence encoded by a nucleotide sequence that hybridizes under stringent conditions to a gene consisting of the nucleotide sequence of SEQ ID NO: 15 or 17; and
(b) contacting a cellular sample potentially comprising a dopaminergic neuron and/or a progenitor cell thereof with a polynucleotide that hybridizes under stringent conditions to transcripts of either or both of the genes selected from DAT and ADH2, or with an antibody that binds to translation products of said selected genes;

[20] the method of any one of [16] to [19], wherein the polypeptide consisting of a partial sequence comprises at least 6 consecutive amino acid residues;

[21] a kit for distinguishing a dopaminergic neuron and/or progenitor cell thereof, wherein the kit comprises: the reagent of [7] or [8]; and a polynucleotide that hybridizes under stringent conditions to transcripts of one or more genes selected from the group consisting of Lmx1b, Nurr1, En1, Ptx3, TH, DAT, and ADH2;

[22] a kit for distinguishing a dopaminergic neuron and/or a progenitor cell thereof, wherein the kit comprises: the reagent of [7] or [8]; and an antibody that binds to translation products of one or more genes selected from the group consisting of Lmx1b, Nurr1, En1, Ptx3, TH, DAT, and ADH2;

[23] a method of screening for a differentiation-inducing reagent for a dopaminergic neuron, wherein the method comprises the steps of:
(a) contacting a test substance with cells that can be differentiated into dopaminergic neurons;
(b) detecting a transcript of the Lmx1a gene by contacting the cells, after contact with the test substance, with a polynucleotide that hybridizes under stringent conditions to a transcript of a gene consisting of a nucleotide sequence of any one of (b-1) to (b-6):
    (b-1) the nucleotide sequence of SEQ ID NO: 13;
    (b-2) a nucleotide sequence encoding a polypeptide consisting of the amino acid sequence of SEQ ID NO: 14;
    (b-3) a nucleotide sequence that hybridizes under stringent conditions to a gene consisting of the nucleotide sequence of SEQ ID NO: 13;
    (b-4) the nucleotide sequence of SEQ ID NO: 15 or 17;
    (b-5) the nucleotide sequence encoding a polypeptide consisting of the amino acid sequence of SEQ ID NO: 16 or 18; and
    (b-6) a nucleotide sequence that hybridizes under stringent conditions to a gene consisting of the nucleotide sequence of SEQ ID NO: 15 or 17; and
(c) determining whether the test substance can induce the differentiation of dopaminergic neurons when the transcript of the Lmx1a gene is detected;

[24] the method of [23], wherein the polynucleotide is a nucleotide sequence comprising at least 15 consecutive nucleotides;

[25] a method of screening for a differentiation-inducing reagent for a dopaminergic neuron, wherein the method comprises the steps of:
(a) contacting a test substance with cells that can be differentiated into dopaminergic neurons;
(b) detecting a translation product of the Lmx1a gene by contacting the cells, after contact with the test substance, with an antibody that binds to a polypeptide consisting of an amino acid sequence of any one of (b-1) to (b-6) or a partial sequence thereof:
    (b-1) the amino acid sequence of SEQ ID NO: 14;
    (b-2) an amino acid sequence with a deletion, insertion, substitution, or addition of one or more amino acids in the amino acid sequence of SEQ ID NO: 14;
    (b-3) an amino acid sequence encoded by a nucleotide sequence that hybridizes under stringent conditions to a gene consisting of the nucleotide sequence of SEQ ID NO: 13;
    (b-4) the amino acid sequence of SEQ ID NO: 16 or 18;
    (b-5) an amino acid sequence with a deletion, insertion, substitution, or addition of one or more amino acids in the amino acid sequence of SEQ ID NO: 16 or 18; and
    (b-6) an amino acid sequence encoded by a nucleotide sequence that hybridizes under stringent conditions to a gene consisting of the nucleotide sequence of SEQ ID NO: 15 or 17; and
(c) determining whether the test substance can induce the differentiation of dopaminergic neurons when the translation product of the Lmx1a gene is detected; and

[26] the method of [25], wherein the polypeptide consisting of a partial sequence comprises at least six consecutive amino acid residues.

BEST MODE FOR CARRYING OUT THE INVENTION

<Marker Polynucleotide Probes>

Figure 1:
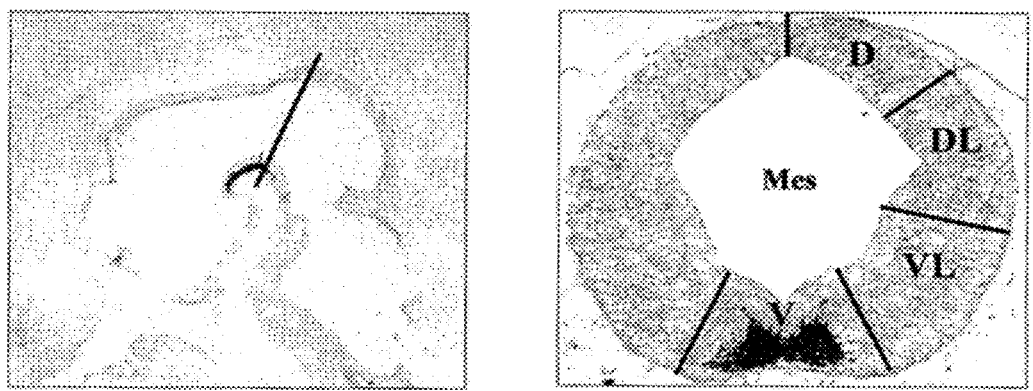
FIG. 1 is a set of photographs showing the expression of the dopaminergic neuron marker gene tyrosine hydroxylase (TH) in the ventral region of an E12.5 mouse midbrain. The left-hand photograph is a sagittal section and the right-hand photograph is a coronal section performed along the line in the left-hand photograph. Furthermore, the midbrain region was cut into four regions, and VL from subtracted from V. Mes: mesal, D: dorsal, DL: dorsal lateral, VL: ventral lateral, and V: ventral.

The "dopaminergic neuron marker polynucleotide probes" of the present invention are used as markers that select and/or detect dopaminergic neuron progenitor cells before and after proliferation, and dopaminergic neurons. These polynucleotides can detect the expression of Lmx1a gene, which is expressed at all stages of differentiation, from dopaminergic neuron progenitor cells before cell cycle exit to dopaminergic neurons in adults. The nucleotide sequences of Lmx1a genes are known. For example, the sequence of mouse Lmx1a can be referred to in Nature 403: 764-769 (2000); Nature 420: 563-573 (2002); Mech. Dev. 118: 225-228 (2002); and such, and is also registered in GenBank under the Accession No. NM_033652. Furthermore, human Lmx1a has been reported in Gene 290: 217-225 (2002). The genomic sequence of human Lmx1a is registered in GenBank under the Accession No. AH011517, and isoforms such as the 6A mutant (GenBank Accession No. NM_177398) have also been reported.

Here, a "marker polynucleotide probe" refers to a polymer composed of a number of nucleotides, such as deoxyribonucleic acids (DNAs) or ribonucleic acids (RNAs), or nucleotide pairs that should be able to detect expression of the Lmx1a gene. Double-stranded cDNA can also be used as a probe in tissue in situ hybridization, and such double-stranded cDNAs are included in the markers of the present invention. RNA probes (riboprobes) are particularly preferable as marker polynucleotide probes for detecting RNA in tissues. When detecting Lmx1a gene expression by using the presence or absence of mRNA expression, it is preferable to use the region encoding Lmx1a. The amino acid sequence of mouse Lmx1a is registered in GenBank as NP_387501.1. The coding region corresponds to nucleotides 220 to 1368 in the sequence of NM_033652, and its specific sequence is shown in SEQ ID NO: 14. In addition, the amino acid sequence of human Lmx1a is also known (GenBank Accession No. AAL82892.1, etc.), and its specific sequences are shown in SEQ ID NOs: 16 and 18.

If needed, the marker polynucleotide probes of the present invention can also contain non-naturally-occurring nucleotides such as 4-acetylcytidine, 5-(carboxyhydroxymethyl) uridine, 2'-O-methylcytidine, 5-carboxymethylaminomethyl-2-thiouridine, 5-carboxymethylaminomethyluridine, dihydrouridine, 2'-O-methylpseudouridine, β-D-galactosylqueuosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueuosine, 5-methoxycarbonylmethyl-2-thiouridine, 5-methoxycarbonylmethyluridine, 5-methoxyuridine, 2-methylthio-N6-isopentenyladenosine, N-((9-β-D-ribofuranosyl-2-methylthiopurin-6-yl)carbamoyl)threonine, N-((9-β-D-ribofuranosylpurin-6-yl)N-methylcarbamoyl)threonine, uridine-5-oxyacetic acid-methyl ester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9-β-D-ribofuranosylpurin-6-yl)carbamoyl)threonine, 2'-O-methyl-5-methyluridine, 2'-O-methyluridine, wybutosine, and 3-(3-amino-3-carboxy propyl) uridine.

The marker polynucleotide probes of the present invention comprise nucleotide sequences that are complementary to the mRNA of Lmx1a, which is specifically expressed in dopaminergic neurons. For example, the nucleotide sequence of mouse Lmx1a cDNA is registered in GenBank with the Accession No. NM_033652, and its specific sequence is shown in SEQ ID NO: 13. Polynucleotides with a sequence complementary to this cDNA can be used as the marker polynucleotide probes of the present invention. Furthermore, the amino acid sequence of mouse Lmx1a is registered in GenBank under the Accession No. NP_387501.1 (SEQ ID NO: 14); however, due to degeneration of the genetic code, its nucleotide sequence may differ from the nucleotide sequence of above-mentioned GenBank Accession No. NM_033652 (SEQ ID NO: 13). Polynucleotides complementary to such degenerate sequences are also comprised in the marker polynucleotide probes of the present invention. Furthermore, in addition to degenerate sequences, polynucleotides complementary to nucleotide sequences that hybridize under stringent conditions to Lmx1a genes (genes comprising the nucleotide sequence of SEQ ID NO: 13) are also comprised in the marker polynucleotide probes that can be used in the present invention.

Similarly, human Lmx1a sequences are also known (SEQ ID NOs: 15 and 17), and the marker polynucleotide probes of the present invention also comprise polynucleotides with a sequence complementary to human Lmx1a mRNA, polynucleotides with a degenerate relationship to these polynucleotides, and polynucleotides complementary to nucleotide sequences that hybridize under stringent conditions to human Lmx1a genes (SEQ ID NOs: 15 and 17).

Herein, the phrase "complementary to a nucleotide sequence" comprises not only nucleotide sequences that completely match a template, but also those in which at least 70%, preferably 80%, more preferably 90%, and even more preferably 95% or more (for example, 97%, 98% or 99%) of the nucleotides of the sequence match the template. It is known that genes with such high homology are likely to encode polypeptides with the same function. Herein, "matching" refers to the formation of a chain in which: adenine (A) in the nucleotide sequence of the template polynucleotide pairs with thymine (T) (or urasil (U) in case of RNA), T or U pair with A, cytosine (C) pairs with (G), and G pairs with C. Homology between specific nucleotide chains at the nucleotide sequence level can be determined, for example, by the BLAST algorithm (Altschul (1990) Proc. Natl. Acad. Sci. USA 90: 5873-7). BLASTN (Altschul et al. (1990) J. Mol. Biol. 215: 403-410) has been developed as a program for determining homology between nucleotide sequences based on this algorithm, and can be used to determine the homology between a marker polynucleotide probe sequence and a template sequence. For specific analysis methods refer to the world wide web at ncbi.nlm.nih.gov, for example.

Alternative isoforms and allelic variants may exist for Lmx1a. Polynucleotides that can detect such isoforms and allelic variants can also be used as marker polynucleotide probes of the present invention. In addition, as mentioned above, there is a high possibility that genes with high homology will encode polypeptides with the same function. Furthermore, such polynucleotides having high homology can often form pairs under stringent hybridization conditions. Therefore, the marker polynucleotide probes of the present invention comprise polynucleotides that comprise nucleotide sequences that hybridize under stringent conditions to a polynucleotide consisting of the nucleotide sequence encoding Lmx1a, which is specifically expressed in dopaminergic neurons. Such isoforms, allelic mutants, and polynucleotides having high homology can be obtained from cDNA libraries and genomic libraries of animals such as humans, mice, rats, rabbits hamsters, chickens, pigs, cows, goats, and sheep by, for example, preparing probes based on known nucleotide sequences of the Lmx1a gene, and using these probes to carry out known hybridization methods such as colony hybridization, plaque hybridization, and Southern blotting. See "Molecular Cloning, A Laboratory Manual 2nd ed." (Cold Spring Harbor Press (1989)) for methods of constructing cDNA libraries. In addition, commercially available cDNA libraries or genomic libraries may also be used.

Construction of a cDNA library is explained in more detail below: first, total RNA is prepared from cells, organs, tissues or such that express Lmx1a, using known techniques such as guanidine ultracentrifugation (Chirwin et al. (1979) Biochemistry 18: 5294-5299) or AGPC (Chomczynski and Sacchi (1987) Anal. Biochem. 162: 156-159). Then, an mRNA Purification Kit (Pharmacia) or such is used to purify mRNAs from the total RNA prepared. Alternatively, mRNAs can also be obtained using a kit for direct mRNA preparation, such as a QuickPrep mRNA Purification Kit (Pharmacia). Next, cDNAs are synthesized from the resulting mRNAs using reverse transcriptase. cDNA synthesis kits, such as the AMV Reverse Transcriptase First-strand cDNA Synthesis Kit (Seikagaku Corporation), are also commercially available. Other methods that use the 5'-RACE method to synthesize and amplify cDNAs by PCR may also be used (Frohman et al. (1988) Proc. Natl. Acad. Sci. USA 85: 8998-9002; Belyaysky et al. (1989) Nucleic Acids Res. 17: 2919-32). In addition, in order to construct cDNA libraries containing a high percentage of full-length clones, known techniques such as the oligo-capping method (Maruyama and Sugano (1994) Gene 138: 171-4; Suzuki (1997) Gene 200: 149-56) can also be employed. The cDNAs obtained in this manner are then incorporated into suitable vectors.

Examples of hybridization conditions suitable for use in the present invention include "2×SSC, 0.1% SDS, 50° C.", "2×SSC, 0.1% SDS, 42° C.", and "1×SSC, 0.1% SDS, 37° C.". Conditions of higher stringency include "2×SSC, 0.1% SDS, 65° C.", "0.5×SSC, 0.1% SDS, 42° C.", and "0.2×SSC, 0.1% SDS, 65° C.". More specifically, a method that uses the Rapid-hyb buffer (Amersham Life Science) can be carried out by performing pre-hybridization at 68° C. for 30 minutes or more, adding a probe to allow hybrid formation at 68° C. for one hour or more, washing three times in 2×SSC/0.1% SDS at room temperature for 20 minutes per wash, washing three times in 1×SSC/0.1% SDS at 37° C. for 20 minutes per wash, and finally washing twice in 1×SSC/0.1% SDS at 50° C. for 20 minutes per wash. This can also be carried out using, for example, the Expresshyb Hybridization Solution (CLONTECH), by performing pre-hybridization at 55° C. for 30 minutes or more, then adding a labeled probe and incubating at 37° C. to 55° C. for one hour or more, washing three times in 2×SSC/0.1% SDS at room temperature for 20 minutes per wash, and washing once at 37° C. for 20 minutes with 1×SSC/0.1% SDS. Herein, conditions of higher stringency can be achieved by setting a high temperature for pre-hybridization, hybridization, and the second wash. For example, a pre-hybridization and hybridization temperature of 60° C. can be raised to 68° C. for higher stringency. In addition to factors such as the salt concentration of the buffer and temperature, one with ordinary skill in the art can also integrate other factors, such as probe concentration, probe length, nucleotide sequence composition of the probe, and reaction time, to obtain Lmx1a isoforms and allelic variants, and corresponding genes derived from other organisms.

For detailed information on hybridization procedures refer to Molecular Cloning, A Laboratory Manual $2^{nd}$ ed. (Cold Spring Harbor Press (1989); Section 9.47-9.58), Current Protocols in Molecular Biology (John Wiley & Sons (1987-1997); Section 6.3-6.4), DNA Cloning 1: Core Techniques, A Practical Approach $2^{nd}$ ed. (Oxford University (1995); Section 2.10 for conditions, in particular). Examples of hybridizing polynucleotides include polynucleotides containing a nucleotide sequence that has at least 50% or more, preferably 70% or more, more preferably 80% or more and even more preferably 90% or more (for example, 95% or more, or furthermore 96%, 97%, 98%, or 99% or more) identity with a known nucleotide sequence of Lmx1a. Such identities can be determined using the BLAST algorithm (Altschul et al. (1990) Proc. Natl. Acad. Sci. USA 87: 2264-8; Karlin and Altschul (1993) Proc. Natl. Acad. Sci. USA 90: 5873-7) as for determining homology. In addition to the above-described BLASTN program for nucleotide sequences, the BLASTX program for determining the identity of amino acid sequences (Altschul et al. (1990) J. Mol. Biol. 215: 403-10) has also been developed based on this algorithm and can be used to determine identity at the amino acid level. As described above, on the world wide web at ncbi.nlm.nih.gov can be referred to for specific examples of analysis methods.

Genes with an Lmx1a-like structure and function, such as Lmx1a isoforms and allelic variants, can be obtained from cDNA libraries and genomic libraries of animals such as mice, rats, rabbits, hamsters, chickens, pigs, cows, goats, sheep, and primates comprising humans by designing primers based on known nucleotide sequences of the Lmx1a gene, using gene amplification technology (PCR) (Current Protocols in Molecular Biology, John Wiley & Sons (1987) Sections 6.1-6.4).

The polynucleotide sequences can be confirmed by using conventional methods for determining sequence. For example, the dideoxynucleotide chain termination method (Sanger et al. (1977) Proc. Natl. Acad. Sci. USA 74: 5463) can be used. In addition, sequences can also be analyzed using a suitable DNA sequencer.

Moreover, since it is preferable that the marker polynucleotide probes of the present invention should specifically detect Lmx1a expression, the present marker polynucleotide probes comprise polynucleotides that consist of nucleotide sequences containing at least 15 consecutive nucleotides from each of the nucleotide sequences of: (1) a sequence complementary to Lmx1a mRNA; (2) a sequence complementary to the nucleotide sequence encoding the amino acid sequence of Lmx1a; and (3) a sequence hybridizing under stringent conditions to Lmx1a mRNA. Such polynucleotides comprising nucleotide sequences that contain at least 15 consecutive nucleotides can be used as probes for detecting Lmx1a mRNA expression, or as PCR or RT-PCR primers for amplifying Lmx1a mRNA. When used as probes the polynucleotides normally consist of 15 to 100, and preferably 15 to 35 nucleotides, and when used as primers they normally consist of at least 15 or more and preferably around 30 nucleotides. When using as primers, the polynucleotides can be designed to have a restriction enzyme recognition sequence or tag or such added to their 5'-end, and at their 3' end, a sequence complementary to a target sequence. Such polynucleotides, which consist of nucleotide sequences comprising at least 15 consecutive nucleotides, can hybridize with Lmx1a mRNAs.

Marker polynucleotide probes of the present invention can be prepared from cells that express Lmx1a using the aforementioned hybridization or PCR or such. In addition, they can also be produced by chemical synthesis based on known Lmx1a sequence data. Riboprobes, which are considered to be particularly preferable for detecting RNAs in tissue, can be obtained by inserting a cloned Lmx1a gene or portion thereof into plasmid vector pSP64 in the reverse direction, followed by run-off transcription of the inserted sequence portion. Although pSP64 contains an SP6 promoter, methods for producing riboprobes by combining phage T3, T7 promoter and RNA polymerase are also known.

<Antibodies>

The present invention provides anti-Lmx1a antibodies that can be used for tissue immunostaining and such of dopaminergic neurons. Antibodies of the present invention include polyclonal antibodies, monoclonal antibodies, chimeric antibodies, single-chain antibodies (scFv) (Huston et al. (1988) Proc. Natl. Acad. Sci. USA 85: 5879-83; The Pharmacology of Monoclonal Antibody, Vol. 113, Rosenburg and Moore ed., Springer Verlag (1994) pp. 269-315), humanized antibodies, multispecific antibodies (LeDoussal et al. (1992) Int. J. Cancer Suppl. 7: 58-62; Paulus (1985) Behring Inst. Mitt. 78: 118-32; Millstein and Cuello (1983) Nature 305: 537-9; Zimmermann (1986) Rev. Physiol. Biochem. Pharmacol. 105: 176-260; VanDijk et al. (1989) Int. J. Cancer 43: 944-9), and antibody fragments such as Fab, Fab', F(ab')$_2$, Fc, and Fv. Moreover, the antibodies of the present invention may also be modified by PEG and such, as necessary. Antibodies of the present invention can also be produced in the form of fusion proteins with β-galactosidase, maltose-binding protein, GST, green fluorescent protein (GFP) and such, to allow detection without the use of a secondary antibody. In addition, the antibodies can be modified by labeling with biotin or such, to allow detection or recovery using avidin, streptavidin, or such.

The antibodies of the present invention are specific to any of: (1) a polypeptide encoded by a Lmx1a gene (SEQ ID NOs: 13, 15, and 17); (2) a Lmx1a polypeptide (SEQ ID NOs: 14, 16, and 18); (3) a polypeptide comprising an amino acid sequence with a deletion, insertion, substitution, or addition of one or more amino acids in a Lmx1a polypeptide (SEQ ID NOs: 14, 16, and 18); (4) a polypeptide encoded by a nucleotide sequence that hybridizes under stringent conditions to a sequence complementary to the nucleotide sequence of a Lmx1a gene (SEQ ID NOs: 13, 15, and 17); and (5) a partial fragment from any of the above-mentioned polypeptides of (1) to (4), which has antibody-inducing antigenicity, such as a polypeptide comprising at least six amino acid residues (for example 6, 8, 10, 12 or 15 amino acid residues or more).

The antibodies of the present invention can be produced by using, as a sensitizing antigen, an Lmx1a polypeptide or fragment thereof, or cells expressing the same. In addition, short fragments of Lmx1a polypeptide may also be used as immunogens when coupled to a carrier such as bovine serum albumin, Keyhole-limpet hemocyanin, and ovalbumin. In addition, Lmx1a polypeptides or fragments thereof may be used in combination with known adjuvants, such as aluminum adjuvant, Freund's complete (or incomplete) adjuvant, or pertussis adjuvant, to enhance the immune response to the antigen.

The "Lmx1a polypeptides" for obtaining the antibodies of the present invention comprise naturally occurring Lmx1a derived from humans, mice, and such. The amino acid residues constituting the Lmx1a polypeptide may be naturally occurring or modified amino acids. Moreover, the Lmx1a polypeptides of the present application comprise fusion proteins modified by other peptide sequences.

The Lmx1a polypeptides for obtaining the antibodies of the present invention should have the antigenicity of Lmx1a and comprise a polypeptide comprising an amino acid sequence with a deletion, insertion, substitution, or addition of one or more amino acid residues in the amino acid sequence of naturally occurring Lmx1a. It is well known that mutant polypeptides consisting of an amino acid sequence with a deletion, insertion, substitution, or addition of one or more amino acids, maintain the same biological activity as the original polypeptide (Mark et al. (1984) Proc. Natl. Acad. Sci. USA 81: 5662-6; Zoller and Smith (1982) Nucleic Acids Res. 10: 6487-500; Wang et al. (1984) Science 224: 1431-3; Dalbadie-McFarland et al. (1982) Proc. Natl. Acad. Sci. USA 79: 6409-13). Methods for deleting, inserting, substituting, or adding one or more amino acids in a given protein while maintaining the original antigenicity of the protein are known in the art. For example, polynucleotides encoding mutant proteins may be prepared by site-directed mutagenesis and expressed appropriately to obtain the mutant proteins (Molecular Cloning, A Laboratory Manual 2nd ed., Cold Spring Harbor Press (1989); Current Protocols in Molecular Biology, John Wiley & Sons, (1987-1997), Section 8.1-8.5; Hashimoto-Goto et al. (1995) Gene 152: 271-5; Kunkel (1985) Proc. Natl. Acad. Sci. USA 82: 488-92; Kramer and Fritz (1987) Method. Enzymol. 154: 350-67; Kunkel (1988) Method. Enzymol. 85: 2763-6).

The antibodies of the present invention comprise those that are specific to a portion of an Lmx1a polypeptide. In other words, as well as polypeptides with the full-length amino acid sequence of Lmx1a, the "Lmx1a polypeptides" for obtaining the antibodies of the present invention comprise polypeptide fragments with sequences that are identical to at least six amino acid residues or more (for example, 6, 8, 10, 12 or 15 amino acid residues or more) of Lmx1a. Particularly preferable fragments can be exemplified by a polypeptide fragment of the Lmx1a amino terminus, carboxyl terminus, or such. The Lmx1a polypeptide fragments include fragments containing an α-helix and α-helix fanning region, an α-amphipathic region, a β-sheet and β-sheet forming region, a β-amphipathic region, a substrate binding region, a high antigen index region, a coil and coil forming region, a hydrophilic region, a hydrophobic region, a turn and turn forming region, and a surface forming region. In the context of the present application, Lmx1a polypeptide fragments may be any fragments, as long as they have the antigenicity of an Lmx1a polypeptide. The antigen-determining site of a polypeptide can be predicted using methods for analyzing the hydrophobicity/hydrophilicity of the amino acid sequence of a protein (Kyte-Doolittle (1982) J. Mol. Biol. 157: 105-22), or methods of secondary structure analysis (Chou-Fasman (1978) Ann. Rev. Biochem. 47: 251-76), and can be confirmed using computer programs (Anal. Biochem. 151: 540-6 (1985)) or the PEPSCAN method in which a short peptide is synthesized before its antigenicity is confirmed (Japanese Patent Kohyo Publication No. (JP-A) S60-500684 (unexamined Japanese national phase publication corresponding to a non-Japanese international publication)), or the like.

Lmx1a polypeptides and Lmx1a polypeptide fragments can be isolated from Lmx1a-expressing cells, tissues, or organs, based on their physical properties. Alternatively, these polypeptides and polypeptide fragments can also be produced using known genetic recombination techniques, chemical synthesis methods, or such. For example, for in vitro Lmx1a polypeptide production, Lmx1a polypeptides can be produced in an in vitro cell-free system using in vitro translation methods (Dasso and Jackson (1989) Nucleic Acids Res. 17: 3129-44). In contrast, when producing polypeptides using cells, a polynucleotide that encodes a polypeptide of interest is first incorporated into an appropriate expression vector, a suitable cell host is selected, and then the cells are transformed by the expression vector. The polypeptide of interest can then be obtained by culturing the transformed host cells under conditions that express the polypeptide most efficiently.

Vectors for expressing polypeptides include vectors of various origins, such as plasmids, cosmids, viruses, and bacteriophages (Molecular Cloning, A Laboratory Manual 2$^{nd}$ ed., Cold Spring Harbor Press (1989); Current Protocols in Molecular Biology, John Wiley & Sons (1987)). Vectors comprise regulatory sequences into which a desired polynucleotide is incorporated so it will be under the control of the regulatory sequences when expressed in transfected host cells. Here, the "regulatory sequences" include promoters, ribosome binding sites and terminators in the case of a prokaryotic host cells, and promoters and terminators in the case of eukaryotic host cells, and in some cases the sequences may also contain transactivators, transcription factors, polyA signals which stabilize transcription products, splicing and polyadenylation signals, and others. Such regulatory sequences comprise all the components required for the expression of polynucleotides linked thereto. The vectors may further comprise selection markers. Alternatively, a signal peptide necessary to transfer an intracellularly expressed polypeptide into the lumen of the endoplasmic reticulum or outside of the cell, or, when the host is a Gram negative microbe, into the periplasm or extracellular space, can also be incorporated into an expression vector such that its nucleotide sequence is linked to the polypeptide of interest and expressed. Various signal peptides derived from heterogeneous proteins are known and can be used. Linkers may also be added, and start (ATG) or stop codons (TAA, TAG, or TGA) may be inserted as necessary.

Examples of vectors capable of expressing polypeptides in vitro include pBEST (Promega). In addition, various vectors are known to be suitable for expression in prokaryotic hosts (see, e.g., "Basic Microbiology Course 8—Genetic Engineering" (Kyoritsu Publishing)). One with ordinary skill in the art can suitably select vectors suitable for the hosts and suitable methods for introducing vectors into the hosts. Various host cells are known. For example, fungal cells such as yeasts and molds, higher plants, insects, fish, amphibians, reptiles, birds, mammalian cells and such, and various culture cell systems (COS, HeLa, C127, 3T3, BHK, HEK293, Bowes melanoma cells, myeloma, Vero, Namalwa, Namalwa KJM-1, and HBT5637 (Japanese Patent Application Kokai Publication No. (JP-A) S63-299 (unexamined, published Japanese patent application)), etc.) can also be used as hosts to express Lmx1a polypeptides and their antigenic fragments. Vector systems suitable for each cell and methods for introducing a vector into host cells are also known. Moreover, methods for expressing exogenous proteins in animals in vivo (see, e.g., Susumu (1985) Nature 315: 592-4; Lubon (1998) Biotechnol. Annu. Rev. 4: 1-54) and in plant bodies are also known, and can be used to express Lmx1a polynucleotides.

DNAs can be inserted into vectors by ligase reactions using restriction enzyme sites (Current Protocols in Molecular Biology, John Wiley & Sons (1987) Section 11.4-11.11; Molecular Cloning, A Laboratory Manual 2nd ed., Cold Spring Harbor Press (1989) Section 5.61-5.63). In addition, the Lmx1a polypeptide expression vectors can be designed as necessary by selecting nucleotide sequences with high expression efficiency in view of the frequency of the host's codon usage (Grantham et al. (1981) Nucleic Acids Res. 9: r43-74). The cells of the hosts that produce the Lmx1a polypeptides comprise polynucleotides encoding the Lmx1a polypeptides. So long as the polynucleotides are expressed properly, the polynucleotides themselves may be regulated by their own promoter, incorporated in the host genome, or maintained as extrachromosomal structures.

The host cells are cultured using known methods appropriate to the host cells selected. For example, when animal cells are the hosts, the cells can be cultured for about 15 to 200 hours at a pH of about 6 to 8 and a temperature of 30° C. to 40° C., using a medium such as DMEM (Virology 8: 396 (1959)), MEM (Science 122: 501 (1952)), RPMI1640 (J. Am. Med. Assoc. 199: 519 (1967)), 199 (Proc. Soc. Biol. Med. 73: 1 (1950)), or IMDM, adding serum such as fetal calf serum (FCS), as necessary. In addition, the medium may be replaced, aerated, or stirred during the course of culturing, as necessary.

Normally, the Lmx1a polypeptides produced by gene recombination techniques can be recovered from the medium if they are secreted outside of the cells or from body fluids when the host is a transgenic organism. When the polypeptides are produced inside the cells, the cells are dissolved and the polypeptides are recovered from the dissolution products. The polypeptides of interest are then purified by suitably combining known methods of protein purification, such as salting out, distillation, various types of chromatography, gel electrophoresis, gel filtration, ultrafiltration, recrystallization, acid extraction, dialysis, immunoprecipitation, solvent precipitation, solvent extraction, and ammonium sulfate or ethanol precipitation. Examples of chromatography include ion exchange chromatography, such as anion or cation exchange chromatography, affinity chromatography, reversed-phase chromatography, adsorption chromatography, gel filtration chromatography, hydrophobic chromatography, hydroxyapatite chromatography, phosphocellulose chromatography, and lectin chromatography (Strategies for Protein Purification and Characterization: A Laboratory Course Manual, Marshak et al. ed., Cold Spring Harbor Laboratory Press (1996)). The proteins can be purified by liquid phase chromatography, such as HPLC or FPLC, using various types of columns. In addition, for example, when a desired protein is expressed as a fusion protein with GST, purification methods using glutathione columns are effective. On the other hand, proteins with histidine tags can be purified using nickel columns. When the Lmx1a polypeptides are produced as fusion proteins, they can be purified and then unnecessary portions can be removed using enzymes such as thrombin or factor Xa, as necessary.

Naturally occurring polypeptides can also be purified based on their physical properties and used as antigens to obtain the antibodies of the present invention. The purified polypeptides can also be modified using enzymes such as chymotrypsin, glucosidase, trypsin, protein kinase, and lysyl endopeptidase, as necessary. In addition to the aforementioned chemical synthesis and genetic engineering techniques used for the Lmx1a polypeptides, Lmx1a polypeptide fragments can also be produced by using suitable enzymes, such as peptidases, to cleave an Lmx1a polypeptide.

Polyclonal antibodies specific to dopaminergic neurons can be obtained from, for example, the serum collected from immunized animals after immunizing mammals with purified Lmx1a polypeptides or fragments thereof, coupled to adjuvants as required. Although there are no particular limitations as to the mammals used, typical examples include rodents, lagomorphs and primates. Specific examples include rodents such as mice, rats and hamsters, lagomorphs such as rabbits, and primates such as monkeys, including cynomolgus monkeys, rhesus monkeys, baboons and chimpanzees. Animals can be immunized by suitably diluting and suspending a sensitizing antigen in phosphate-buffered saline (PBS) or physiological saline, mixing with an adjuvant as necessary until emulsified, and injecting into an animal intraperitoneally or subcutaneously. The sensitizing antigens mixed with Freund's incomplete adjuvant are preferably administered several times every four to 21 days. Antibody production can be confirmed by using conventional methods to measure the level of an antibody of interest in the serum. Finally, the serum itself may be used as a polyclonal antibody, or it may be further purified. See, for example, "Current Protocols in Molecular Biology" (John Wiley & Sons (1987) Sections 11.12-11.13) for specific methods.

Monoclonal antibodies can be produced by removing the spleen from an animal immunized in a manner described above, separating immunocytes from the spleen, and fusing them with a suitable myeloma cell using polyethylene glycol (PEG) or such to establish hybridomas. Cell fusion can be carried out according to the Milstein method (Galfre and Milstein (1981) Methods Enzymol. 73: 3-46). Cells that allow chemical selection of fused cells are particularly preferable for the myeloma cells. When using such myeloma cells that allow chemical selection, fused hybridomas can be selected by culturing in a culture medium (HAT culture medium) containing hypoxanthine, aminopterin, and thymidine, which destroys non-fused cells. Next, clones that produce antibodies against Lmx1a polypeptides, or fragment thereof, are selected from the established hybridomas. The selected clones are then introduced into the abdominal cavities of mice or such, and ascites is collected to obtain the monoclonal antibodies. For information on specific methods see "Current Protocols in Molecular Biology" (John Wiley & Sons (1987) Section 11.4-11.11).

Hybridomas can also be obtained by first using an immunogen to sensitize human lymphocytes that have been infected by EB virus in vitro, then fusing the sensitized lymphocytes with human myeloma cells (such as U266) to obtain hybridomas that produce human antibodies (Japanese Patent Application Kokai Publication No. (JP-A) S63-17688 (unexamined, published Japanese patent application)). In addition, human antibodies can also be obtained by using antibody-producing cells generated by sensitizing transgenic animals which have the repertoire of human antibody genes (WO92/03918; WO93/02227; WO94/02602; WO94/25585; WO96/34096; Mendez et al. (1997) Nat. Genet. 15: 146-156, etc.). Methods that do not use hybridomas can be exemplified by methods in which cancer genes are introduced to immortalize immunocytes, such as antibody-producing lymphocytes.

In addition, antibodies can also be produced by genetic recombination techniques (see Borrebaeck and Larrick (1990) Therapeutic Monoclonal Antibodies, MacMillan Publishers Ltd., UK). First, a gene that encodes an antibody is cloned from hybridomas or antibody-producing cells (such as sensitized lymphocytes). The resulting gene is then inserted into a suitable vector, the vector is introduced into a host, and the host is cultured to produce the antibody. This type of recombinant antibody is also included in the antibodies of the present invention. Typical examples of recombinant antibodies include chimeric antibodies, which comprise a non-human antibody-derived variable region and a human antibody-derived constant region, and humanized antibodies, which comprise a non-human-derived antibody complementarity determining region (CDR), human antibody-derived framework region (FR), and human antibody constant region (Jones et al. (1986) Nature 321: 522-5; Reichmann et al. (1988) Nature 332: 323-9; Presta (1992) Curr. Op. Struct. Biol. 2: 593-6; Methods Enzymol. 203: 99-121 (1991)).

Antibody fragments can be produced by treating the aforementioned polyclonal or monoclonal antibodies with enzymes such as papain or pepsin. Alternatively, an antibody fragment can be produced by genetic engineering techniques using a gene that encodes an antibody fragment (see Co et al., (1994) J. Immunol. 152: 2968-76; Better and Horwitz (1989) Methods Enzymol. 178: 476-96; Pluckthun and Skerra (1989) Methods Enzymol. 178: 497-515; Lamoyi (1986) Methods Enzymol. 121: 652-63; Rousseaux et al. (1986) 121: 663-9; Bird and Walker (1991) Trends Biotechnol. 9: 132-7).

Multispecific antibodies include bispecific antibodies (BsAb), diabodies (Db), and such. Multispecific antibodies can be produced by methods such as (1) chemically coupling antibodies having different specificities with different types of bifunctional linkers (Paulus (1985) Behring Inst. Mitt. 78: 118-32), (2) fusing hybridomas that secrete different monoclonal antibodies (Millstein and Cuello (1983) Nature 305: 537-9), or (3) transfecting eukaryotic cell expression systems, such as mouse myeloma cells, with a light chain gene and a heavy chain gene of different monoclonal antibodies (four types of DNA), followed by the isolation of a bispecific monovalent portion (Zimmermann (1986) Rev. Physio. Biochem. Pharmacol. 105: 176-260; Van Dijk et al. (1989) Int. J. Cancer 43: 944-9). On the other hand, diabodies are dimer antibody fragments comprising two bivalent polypeptide chains that are constructed by gene fusion. These can be produced using known methods (see Holliger et al. (1993) Proc. Natl. Acad. Sci. USA 90: 6444-8; EP404097; WO93/11161).

Antibodies and antibody fragments can be recovered and purified using Protein A and Protein G. They can also be purified by the protein purification techniques described above, in the same way as for non-antibody polypeptides (Antibodies: A Laboratory Manual, Ed Harlow and David Lane, Cold Spring Harbor Laboratory (1988)). For example, when using Protein A to purify an antibody of the present invention, known Protein A columns such as Hyper D, POROS, or Sepharose F.F. (Pharmacia) can be used. The concentration of the resulting antibody can be determined by measuring absorbance or by using an enzyme linked immunoadsorbent assay (ELISA).

The antigen binding activity of an antibody can be determined by measuring absorbance, or by using fluorescent antibody methods, enzyme immunoassay (EIA) methods, radioimmunoassay (RIA) methods, or ELISA. When ELISA is used, an antibody of the present invention is first immobilized onto a support, such as a plate. An Lmx1a polypeptide is then added, and a sample containing the antibody of interest is added. Herein, the samples containing an antibody of interest include, for example, culture supernatants of antibody-producing cells, purified antibodies, and such. Next, a secondary antibody that recognizes an antibody of the present invention is added, and the plate is incubated. The plate is then washed and the label attached to the secondary antibody is detected. Specifically, if a secondary antibody is labeled with alkaline phosphatase, for example, its antigen binding activity can be determined by adding an enzyme substrate such as p-nitrophenyl phosphate, and then measuring the absorbance. In addition, a commercially available system such as BIAcore (Pharmacia) can also be used to evaluate antibody activities.

<Detection of Dopaminergic Neurons>

The present invention provides methods for selectively detecting dopaminergic neurons. Dopaminergic neurons at all stages of differentiation, from proliferating dopaminergic neuron progenitor cells before cell cycle exit to mature dopaminergic neurons, can be detected using Lmx1a expression as an index. The methods for detecting dopaminergic neurons using polynucleotides or antibodies of the present invention can be used to diagnose disorders, such as Parkinson's disease, that involve degeneration of dopaminergic neurons. Dopaminergic neurons can be detected using the marker polynucleotide probes or antibodies of the present invention.

More specifically, the present invention provides methods for detecting dopaminergic neurons, comprising the step of contacting a marker polynucleotide probe of the present invention with a cell sample containing potential dopaminergic neurons. In these methods, the marker polynucleotide probes are preferably labeled with a radioactive isotope or non-radioactive compound. Examples of radioactive isotopes used for labeling include $^{35}$S and $^{3}$H. When using a radiolabeled marker polynucleotide probe, RNAs that bind to the marker can be detected by using emulsion autoradiography to detect silver particles. In addition, commonly known non-radioactive isotopes for labeling a marker polynucleotide probe include biotin and digoxigenin. A biotin-labeled marker can be detected using, for example, fluorescently labeled avidin, or avidin labeled with an enzyme such as alkaline phosphatase or horseradish peroxidase. Digoxigenin-labeled markers can be detected using anti-digoxigenin antibodies labeled with fluorescence or an enzyme, such as alkaline phosphatase or horseradish peroxidase. When using enzyme labeling, detection is carried out by incubating with the enzyme substrate to form a stable pigment at the marker location. Fluorescent in situ hybridization (FISH) is a convenient and particularly preferable method for detecting dopaminergic neurons.

Furthermore, the present invention provides methods for detecting dopaminergic neurons, which comprise the step of contacting an anti-Lmx1a antibody with a cellular sample potentially comprising dopaminergic neurons. Specifically, cells expressing an Lmx1a polypeptide and dopaminergic neurons at all differentiation stages, from mature dopaminergic neurons to progenitor cells before cell cycle exit, can be detected and selected by contacting cellular samples predicted to comprise dopaminergic neurons or progenitor cells thereof with an antibody of the present invention, and selecting the cells that bind to the antibody. To simplify this detection/selection, the antibodies of the present invention can be labeled or immobilized onto a solid phase. For detection, techniques such as ELISA, RIA, and surface plasmon resonance may be combined. When purification of the selected dopaminergic neurons or progenitor cells thereof is required, the antibodies of the present invention may be used in affinity chromatography.

Also, by combining the markers of the present invention with conventional markers that detect dopaminergic neurons or progenitor cells thereof, it becomes possible to sort between progenitor cells and mature neurons, and further to sort between progenitor cells before and after cell cycle exit.

For example, progenitor cells and mature neurons can be sorted by combining Lmx1a with DAT and/or ADH2 as markers. As mentioned above, the Lmx1a gene is confirmed to be widely expressed during differentiation from progenitor cells before cell cycle exit to mature dopaminergic neurons. On the other hand, as shown in the Examples described below, the DAT and ADH2 genes are expressed after the cells have differentiated into dopaminergic neurons. Therefore, progenitor cells and mature neurons can be separately detected or selected by detecting the expression of an Lmx1a gene using a marker polynucleotide probe or antibody of the present invention and further analyzing the expression of either the DAT gene, the ADH2 gene, or both in cells in which Lmx1a gene expression was detected.

The first method of the present invention for detecting or selecting dopaminergic neurons and/or progenitor cells thereof comprises the steps of:

(a) contacting a polynucleotide that can hybridize under stringent conditions to an Lmx1a gene transcript with a cellular sample that potentially comprises dopaminergic neurons and/or progenitor cells thereof; and (b) contacting a polynucleotide that hybridizes under stringent conditions to transcripts of one gene selected from the DAT gene or ADH2 gene, or both, or contacting an antibody that binds to the translation products of this selected gene with a cellular sample potentially comprising dopaminergic neurons and/or progenitor cells thereof.

The second method of the present invention for detecting or selecting dopaminergic neurons and/or progenitor cells thereof comprises the steps of:

(a) contacting an antibody that binds to a polypeptide comprising the amino acid sequence of Lmx1a or a partial sequence thereof with a cellular sample potentially comprising dopaminergic neurons and/or progenitor cells thereof; and (b) contacting a polynucleotide that hybridizes under stringent conditions to transcripts of one gene selected from the DAT gene or ADH2 gene, or both, or contacting an antibody that binds to the translation products of this selected gene with a cellular sample potentially comprising dopaminergic neurons and/or progenitor cells thereof.

In both the first and second methods mentioned above, Lmx1a gene expression is analyzed in step (a). To detect Lmx1a gene expression at the transcriptional level, as in the first method, a "polynucleotide that can hybridize under stringent conditions to a Lmx1a gene transcript" is used. The aforementioned marker polynucleotide probes of the present invention can be used as this polynucleotide. To detect Lmx1a gene expression at the translational level, as in the second method, an "antibody that binds to a polypeptide comprising an amino acid sequence of Lmx1a or a partial sequence thereof" is used. The aforementioned anti-Lmx1a antibodies of the present invention can be used as this antibody. In this way, both methods analyze Lmx1a expression in step (a).

In step (b), to investigate whether cells are differentiated mature dopaminergic neurons, the expression of the DAT gene and/or ADH2 gene is examined based on their transcripts or translation products.

Polynucleotides that can detect DAT mRNAs are used as the detection polynucleotides for detecting DAT gene expression based on transcripts. Such polynucleotides for DAT detection, which can hybridize to a DAT mRNA, comprise the following: (1) DNAs or RNAs comprising a nucleotide sequence complementary to a DAT cDNA (SEQ ID NOs: 39 and 41); (2) DNAs or RNAs comprising a nucleotide sequence complementary to a nucleotide sequence encoding the amino acid sequence of SEQ ID NO: 40 or 42 and which is a degenerate sequence of the DAT gene code; and (3) DNAs or RNAs comprising a nucleotide sequence that can hybridize under stringent conditions to the nucleotide sequence of SEQ ID NO: 39 or 41. On the other hand, DAT-binding antibodies are used to detect DAT gene expression at the translational level. DAT-binding antibodies comprise antibodies that are specific to any one of: (1) a DAT polypeptide (SEQ ID NOs: 40 and 42); (2) a polypeptide comprising an amino acid sequence with a deletion, insertion, substitution, or addition of one or more amino acids in the amino acid sequence of a DAT polypeptide (SEQ ID NOs: 40 and 42); and (3) a polypeptide fragment comprising at least six amino acid residues from the polypeptide of (1) or (2).

Similarly polynucleotides that can detect ADH2 mRNAs are used as the detection polynucleotides for detecting ADH2 gene expression based on transcripts. Such polynucleotides for ADH2 detection, which can hybridize to an ADH2 mRNA, comprise the following: (1) DNAs or RNAs comprising a nucleotide sequence complementary to an ADH2 cDNA (SEQ ID NOs: 43 and 45); (2) DNAs or RNAs comprising a nucleotide sequence complementary to a nucleotide sequence encoding the amino acid sequence of SEQ ID NO: 44 or 46 and which is a degenerate sequence of the ADH2 gene code; and (3) DNAs or RNAs comprising a nucleotide sequence that can hybridize under stringent conditions to an ADH2 cDNA (SEQ ID NOs: 43 and 45). On the other hand, ADH2-binding antibodies are used to detect ADH2 gene expression at the translational level. ADH2-binding antibodies comprise antibodies specific to any one of: (1) an ADH2 polypeptide (SEQ ID NOs: 44 and 46); (2) a polypeptide comprising an amino acid sequence with a deletion, insertion, substitution, or addition of one or more amino acids in the amino acid sequence of an ADH2 polypeptide (SEQ ID NOs: 44 and 46); or (3) a polypeptide fragment comprising at least six amino acid residues from the polypeptide of (1) or (2).

As described above, progenitor cells can be selectively detected or selected by subtracting the group of cells in which DAT gene and/or ADH2 gene expression was detected from the group of cells in which Lmx1a gene expression was detected. The detection of expression of Lmx1a gene and the DAT and/or ADH2 genes can be conducted at the same time or in succession. When conducted at the same time, as an example, the expression of each gene can be detected simultaneously by adding different tags to each detection probe or such. When conducted in succession, cells in which Lmx1a gene expression is detected can be selected first, and the presence or absence of DAT and/or ADH2 gene expression can then be confirmed. Alternatively, a group of cells expressing the Lmx1a gene can be selected from a group of cells in which DAT and/or ADH2 gene expressions were not detected.

Next, detection or selection of groups of cells before or after cell cycle exit among the progenitor cells can be achieved by combining as markers, (a) the Lmx1a gene and (b) one or more genes selected from the group consisting of Lmx1b, Nurr1, En1, Ptx3, and TH. Lmx1b, Nurr1, En1, Ptx3, and TH are a group of genes expressed in postmitotic precursor cells. Therefore, the expression of these genes can be used to distinguish progenitor cells after cell cycle exit. On the other hand, the Lmx1a gene is also expressed in proliferating progenitor cells before cell cycle exit. Thus, proliferating progenitor cells before cell cycle exit can be detected or selected from among dopaminergic neuron progenitor cells by detecting or selecting cells expressing Lmx1a but do not express Lmx1b, Nurr1, En1, Ptx3, or TH.

Specifically, the first method of the present invention for detecting or selecting dopaminergic neuron progenitor cells by distinguishing progenitor cells before and after cell cycle exit comprises the steps of:
(a) contacting a polynucleotide that can hybridize under stringent conditions to a Lmx1a gene transcript with a cellular sample potentially comprising dopaminergic neuron progenitor cells; and
(b) contacting a polynucleotide that hybridizes under stringent conditions to a transcript of one or more genes selected from the group consisting of Lmx1b, Nurr1, En1, Ptx3, and TH; or contacting an antibody that binds to a translation product of these genes with a cellular sample potentially comprising dopaminergic neuron progenitor cells.

The second method of the present invention for detecting or selecting dopaminergic neuron progenitor cells by distinguishing progenitor cells before and after cell cycle exit comprises the steps of:
(a) contacting an antibody that binds to the translation product of an Lmx1a gene with a cellular sample potentially comprising dopaminergic neuron progenitor cells; and
(b) contacting a polynucleotide that hybridizes under stringent conditions to a transcript of one or more genes selected from the group consisting of Lmx1b, Nurr1, En1, Ptx3, and TH; or contacting an antibody that binds to a translation product of these genes with a cellular sample potentially comprising dopaminergic neuron progenitor cells.

In both the first and second methods mentioned above, Lmx1a gene expression is detected in step (a) based on transcripts or translation products, as in the aforementioned "method for selecting progenitor cells using Lmx1a and DAT or such". The method and materials for detecting Lmx1a gene expression are the same as those of the aforementioned "method for selecting progenitor cells using Lmx1a and DAT or such".

In step (b), the expression of one or more genes selected from the group consisting of Lmx1b, Nurr1, En1, Ptx3, and TH is analyzed based on transcripts or translation products to distinguish postmitotic precursor cells from among the dopaminergic neuron progenitor cells.

Polynucleotides that can detect Lmx1b mRNAs are used as detection polynucleotides for detecting "Lmx1b gene" expression at the transcriptional level. Such polynucleotides for Lmx1b detection can hybridize to Lmx1b mRNAs and comprise the following: (1) DNAs or RNAs comprising a nucleotide sequence complementary to a Lmx1b cDNA (SEQ ID NOs: 19 and 21); (2) DNAs or RNAs comprising a nucleotide sequence complementary to a nucleotide sequence encoding the amino acid sequence of SEQ ID NO: 20 or 22 and which is a degenerate sequence of Lmx1b gene code; and (3) DNAs or RNAs consisting of a nucleotide sequence that can hybridize under stringent conditions to the nucleotide sequence of SEQ ID NO: 19 or 21. When detecting Lmx1b gene expression at the translational level, Lmx1b-binding antibodies are used. Lmx1b-binding antibodies comprise antibodies that are specific to anyone of: (1) an Lmx1b polypeptide (SEQ ID NOs: 20 and 22); (2) a polypeptide consisting of an amino acid sequence with a deletion, insertion, substitution, or addition of one or more amino acids in the amino acid sequence of an Lmx1b polypeptide (SEQ ID NOs: 20 and 22); or (3) a polypeptide fragment comprising at least six amino acid residues from the polypeptide of (1) or (2).

Polynucleotides that can detect Nurr1 mRNAs are used as detection polynucleotides for detecting "Nurr1 gene" expression at the transcriptional level. Such polynucleotides for Nurr1 detection can hybridize to Nurr1 mRNAs and comprise the following: (1) DNAs or RNAs comprising a nucleotide sequence complementary to a Nurr1 cDNA (SEQ ID NOs: 23 and 25); (2) DNAs or RNAs consisting of a nucleotide sequence complementary to a nucleotide sequence encoding the amino acid sequence of SEQ ID NO: 24 or 26 and which is a degenerate sequence of Nurr1 gene code; and (3) DNAs or RNAs consisting of a nucleotide sequence that can hybridize under stringent conditions to an Nurr1 cDNA (SEQ ID NOs: 23 and 25). When detecting Nurr1 gene expression at the translational level, Nurr1-binding antibodies are used. Nurr1-binding antibodies comprise antibodies that are specific to anyone of: (1) a Nurr1 polypeptide (SEQ ID NOs: 24 and 26); (2) a polypeptide consisting of an amino acid sequence with a deletion, insertion, substitution, or addition of one or more amino acids in the amino acid sequence of a Nurr1 polypeptide (SEQ ID NOs: 24 and 26); or (3) a polypeptide fragment comprising at least six amino acid residues from the polypeptide of (1) or (2).

Polynucleotides that can detect En1mRNA are used as detection polynucleotides for detecting "En1 gene" expression at the transcriptional level. Such polynucleotides for En1 detection can hybridize to En1mRNAs and comprise the following: (1) DNAs or RNAs consisting of a nucleotide sequence complementary to an En1 cDNA (SEQ ID NOs: 27 and 29); (2) DNAs or RNAs consisting of a nucleotide sequence complementary to a nucleotide sequence encoding the amino acid sequence of SEQ ID NO: 28 or 30 and which is a degenerate sequence of En1 gene code; and (3) DNAs or RNAs consisting of a nucleotide sequence that can hybridize under stringent conditions to an En1 cDNA (SEQ ID NOs: 27 and 29). When detecting En1 gene expression at the translational level, En1-binding antibodies are used. En1-binding antibodies comprise antibodies that are specific to anyone of: (1) an En1 polypeptide (SEQ ID NOs: 28 and 30); (2) a polypeptide consisting of an amino acid sequence with a deletion, insertion, substitution, or addition of one or more amino acids in the amino acid sequence of an En1 polypeptide (SEQ ID NOs: 28 and 30); or (3) a polypeptide fragment comprising at least six amino acid residues from the polypeptide of (1) or (2).

Polynucleotides that can detect Ptx3mRNAs are used as detection polynucleotides for detecting "Ptx3 gene" expression at the transcriptional level. Such polynucleotides for Ptx3 detection can hybridize to Ptx3mRNAs and comprise the following: (1) DNAs or RNAs consisting of a nucleotide sequence complementary to an Ptx3 cDNA (SEQ ID NOs: 31 and 33); (2) DNAs or RNAs consisting of a nucleotide sequence complementary to a nucleotide sequence encoding the amino acid sequence of SEQ ID NO: 32 or 34 and which is a degenerate sequence of Ptx3 gene code; and (3) DNAs or RNAs consisting of a nucleotide sequence that can hybridize under stringent conditions to a Ptx3 cDNA (SEQ ID NOs: 31 and 33). When detecting Ptx3 gene expression at the translational level, Ptx3-binding antibodies are used. Ptx3-binding antibodies comprise antibodies that are specific to anyone of: (1) a Ptx3 polypeptide (SEQ ID NOs: 32 and 34); (2) a polypeptide consisting of an amino acid sequence with a deletion, insertion, substitution, or addition of one or more amino acids in the amino acid sequence of a Ptx3 polypeptide (SEQ ID NOs: 32 and 34); or (3) a polypeptide fragment comprising at least six amino acid residues from the polypeptide of (1) or (2).

Polynucleotides that can detect TH mRNAs are used as detection polynucleotides for detecting "TH gene" expression at the transcriptional level. Such polynucleotides for TH detection can hybridize to TH mRNAs and comprise the following: (1) DNAs or RNAs consisting of a nucleotide sequence complementary to a TH cDNA (SEQ ID NOs: 35 and 37); (2) DNAs or RNAs consisting of a nucleotide sequence complementary to a nucleotide sequence encoding the amino acid sequence of SEQ ID NO: 36 or 38 and which is a degenerate sequence of TH gene code; and (3) DNAs or RNAs consisting of a nucleotide sequence that can hybridize under stringent conditions to a TH cDNA (SEQ ID NOs: 35 and 37). When detecting TH gene expression at the translational level, TH-binding antibodies are used. TH-binding antibodies comprise antibodies that are specific to anyone of: (1) a TH polypeptide (SEQ ID NOs: 36 and 38); (2) a polypeptide consisting of an amino acid sequence with a deletion, insertion, substitution, or addition of one or more amino acids in the amino acid sequence of a TH polypeptide (SEQ ID NOs: 36 and 38); or (3) a polypeptide fragment comprising at least six amino acid residues from the polypeptide of (1) or (2).

Of these marker genes that can be used in step (b), selection using Lmx1b, Nurr1, or En1 as the marker is preferable. Expression of these three genes can be detected immediately after cell cycle exit, thus enabling detection and selection with a more accurate distinction of progenitor cells before and after cell cycle exit.

As mentioned above, by subtracting a group of cells in which expression of a Lmx1b, Nurr1, En1, Ptx3, or TH gene was detected from a group of cells in which Lmx1a gene expression was detected, proliferating progenitor cells before cell cycle exit can be selectively detected or selected from among the progenitor cells.

The steps above were explained in the order of (a) detection of Lmx1a gene expression and (b) detection of expression of marker genes such as Lmx1b; however, the present methods are not restricted to this order. Detection of Lmx1a gene expression and detection of the expression of marker genes such as Lmx1b may be performed simultaneously using different tags and such. Alternatively, detection of Lmx1a gene expression may be performed after detecting the expression of marker genes such as Lmx1b. In this case, proliferating progenitor cells can be selected by selecting the group expressing the Lmx1a gene from among the group of cells in which the expression of marker genes such as Lmx1b was not detected.

"Proliferating dopaminergic neuron progenitor cells before cell cycle exit", "dopaminergic neuron progenitor cells after cell cycle exit", and "mature dopaminergic neurons" can be separately detected or selected by further adding to the above method, which detects or selects progenitor cells that have exited the cell cycle and those that have not, the step of detecting the expression of the DAT gene and/or ADH2 gene, which are marker(s) that detect the above cells which have differentiated into mature dopaminergic neurons.

For example, Lmx1a gene expression is first detected using the aforementioned probe, antibody, or such and dopaminergic neurons and progenitor cells are selected. Next, in the group of cells which was selected using Lmx1a gene expression as an index, the expression of the DAT gene or ADH2 gene is examined using their respective probe, antibody, or such. Cells in which the expression of the DAT gene or ADH2 gene was detected at this point are detected or selected as mature dopaminergic neurons. On the other hand, the group of cells in which the expression of the DAT gene or ADH2 gene was not detected is further examined for expression of marker genes such as Lmx1b. Cells in which expression of marker genes such as Lmx1b was detected at this point can be identified as postmitotic precursor cells and cells in which the expression of marker genes such as Lmx1b was not detected can be identified as proliferating progenitor cells before cell cycle exit. The methods of the present invention for selecting or detecting dopaminergic neurons or progenitor cells thereof are not restricted to the orders of detection shown herein, and the order of the detection steps can be suitably determined.

Also, the conditions for designing probes and primers, the stringency conditions, and the definition of hybridization used in the methods of the present invention for detecting or selecting dopaminergic neurons or progenitor cells thereof are the same as the conditions and such used for the probes and primers for detecting Lmx1a gene expression. The methods for producing the antibodies, the types of antibodies, and such used in the methods of the present invention for detecting or selecting dopaminergic neurons or progenitor cells thereof are the same as for the anti-Lmx1a antibodies described above.

Moreover, the present invention provides kits for distinguishing dopaminergic neurons and/or progenitor cells thereof. As mentioned above, by combining an Lmx1a marker polynucleotide or an anti-Lmx1a antibody of the present invention with a marker polynucleotide probe or antibody against one or more genes selected from the group consisting of Lmx1b, Nurr1, En1, Ptx3, TH, DAT, and ADH2, it becomes possible to selectively detect and select progenitor cells or to detect and select a group of cells that have exited the cell cycle and of those that have not from among progenitor cells. Therefore, sets of reagents that combine an above Lmx1a marker polynucleotide or anti-Lmx1a antibody with a marker polynucleotide probe or antibody against one or more genes selected from the group consisting of Lmx1b, Nurr1, En1, Ptx3, TH, DAT and ADH2, are useful as kits for distinguishing dopaminergic neurons and/or progenitor cells thereof. For example, by selecting one or more of Lmx1b, Nurr1, En1, Ptx3 or TH from the group consisting of Lmx1b, Nurr1, En1, Ptx3, TH, DAT and ADH2, and combining a marker polynucleotide probe or antibody against that selected gene with an Lmx1a marker polynucleotide or anti-Lmx1a antibody, the kits become effective in detecting/selecting progenitor cells that have exited the cell cycle and those that have not from among the progenitor cells. Alternatively, by selecting DAT or ADH2 and combining its marker polynucleotide probe or antibody with the Lmx1a marker polynucleotide or the anti-Lmx1a antibody, the kits become effective in detecting/selecting cells by distinguishing between progenitor cells and mature neurons.

<Screening for Differentiation-Inducing Reagents for Dopaminergic Neurons>

Since Lmx1a is a marker specifically expressed in dopaminergic neurons from a relatively early stage of development, it can also be used to screen for reagents that induce the differentiation of dopaminergic neurons. Specifically, the ability of a test substance to induce dopaminergic neuron differentiation can be determined by letting the test substance act on a suitable cellular sample and detecting Lmx1a expression. Therefore, the present invention provides methods of screening for candidate compounds of dopaminergic neuron differentiation-inducing reagents by using Lmx1a expression as an index. Lmx1a expression can be detected by using either a marker polynucleotide probe or an anti-Lmx1a antibody of the present invention.

The cellular samples used herein are preferably cellular samples comprising cells of the ventral midbrain region or cells that can be induced to differentiate into dopaminergic neurons, such as ES cells with pluripotency. Known methods for inducing the differentiation of dopaminergic neurons in vitro comprise methods which use, as the starting material, known ES cells, bone marrow interstitial cells, nerve-derived immortalized cell lines (Japanese Patent Kohyo Publication No. (JP-A) H08-509215 (unexamined Japanese national phase publication corresponding to a non-Japanese international publication); JP-A H11-506930; JP-A 2002-522070), primordial neuron cells (JP-A H11-509729), etc. Moreover, methods for inducing dopaminergic cells from neural tissues that do not normally produce dopamine, such as the striatum and cortex, are also known (JP-A H10-509319). Thus, these cells are preferably used as the cellular samples on which the candidate compounds for dopaminergic neuron differentiation-inducing reagents act.

Herein, any compound may be used as a test substance to be contacted with the cells. Examples comprise gene library expression products, synthetic low-molecular weight compound libraries, synthetic peptide libraries, antibodies, substances released by bacteria, cells (microbial, plant, or animal) extracts, cell culture supernatants (microbial, plant, or animal), purified or partially purified polypeptides, marine organisms, extracts from plants, animals, and such, soil, and random phage peptide display libraries. Test substances screened by the present methods show the ability to induce dopaminergic neuron differentiation. Therefore, such substances can become candidate therapeutic drugs for diseases caused by some defect in dopaminergic neurons, and can be considered effective.

Cell differentiation can be determined by comparing the Lmx1a expression level with that of cells which have not contacted the test substances. Alternatively, cell differentiation can also be determined by comparing the state of the cells, in addition to Lmx1a expression. For example, cell differentiation may be detected through morphological observation under a microscope, or by detecting or quantifying substances, such as dopamine, that are produced in the cells.

<Analysis of Lmx1a Expression Regulatory Region>

An expression regulatory region of Lmx1a can be cloned from genomic DNA by known methods using a sequence of an Lmx1a gene. For example, methods for establishing the transcriptional start site, such as S1 mapping, are known and can be used (Cell Engineering, Supplement 8, New Cell Engineering Experiment Protocol, Cancer Research Division, The Institute of Medical Science, The University of Tokyo ed., Shujunsha Publishing (1993) pp. 362-374). In general, the expression regulatory region of a gene can be cloned by screening a genomic DNA library, using a probe DNA comprising a 15-100 bp segment, and preferably a 30-50 bp segment, of the 5' terminus of the gene. A clone obtained in this manner contains a 5' non-coding region of 10 kbp or more, and is shortened or fragmented by exonuclease treatment, or such. Finally, the shortened sequence portion, comprising a potential expression regulatory region, is evaluated using a reporter gene to determine the strength, regulation, and such, of its expression, thereby making it possible to determine the minimum unit required to maintain the activity of the Lmx1a expression regulatory region.

Gene expression regulatory regions can be predicted using a program such as Neural Network (on the world wide web at fruitfly.org./seq_tools/promoter.html; Reese et al., Biocomputing: Proceedings of the 1996 Pacific Symposium, Hunter and Klein ed., World Scientific Publishing Co., Singapore, (1996)). Programs for predicting the minimum unit required for the activity of an expression regulatory region are also known and can be used (http://biosci.cbs.umn.edu./software/proscan/promoterscan.htm; Prestridge (1995) J. Mol. Biol. 0249: 923-932).

The expression regulatory region of the Lmx1a gene isolated in this way can be used to produce desired polypeptides/proteins in vivo in a dopaminergic neuron-specific manner at all developmental stages of the dopaminergic neurons. Also, since Lmx1a is a marker specifically expressed in dopaminergic neurons from a relatively early stage of development, it can also be used to screen dopaminergic neuron differentiation-inducing reagents. Specifically, a vector is first prepared in which a reporter gene which can be detected is introduced under the regulation of the expression regulatory region of the Lmx1a gene, and suitable cells are transformed with this vector. Then, a test substance is contacted with these cells and induction of reporter gene expression by this test substance is detected. When expression of the reporter gene is detected, the test substance is judged to induce the differentiation of dopaminergic neurons.

<Lmx1a-Binding Proteins>

A sequence of 60 similar amino acid residues is conserved among proteins encoded by homeobox genes. This conserved region is called the "homeodomain" and the DNA region encoding the homeodomain is called the "homeobox". The homeodomain forms a DNA-binding domain with a helix-turn-helix conformation and binds to specific nucleotide sequences by entering the space between the two strands of the DNA. Homeobox gene products are thus thought to function as transcription factors that activate or inactivate the transcription of other genes. On the other hand, the LIM domain has a structure similar to the Zinc finger, consisting of 60 amino acid residues in which the positions of six cysteines and one histidine are conserved. Unlike the Zinc finger, DNA-binding ability has not been detected and the LIM domain is thought to be involved in protein-protein interactions. The LIM domain is thought to suppress the function of the homeodomain by intramolecular binding with the homeodomain. Further, it is thought that when an activator protein binds to the LIM domain, the homeodomain shows DNA-binding activity.

Since the Lmx1a gene is a homeobox gene having a LIM domain, it is thought to regulate the transcription of other genes by binding to activator proteins in vivo. Therefore, proteins that bind to Lmx1a may be used to regulate in vivo, ex vivo and in vitro differentiation, maturation and/or function of dopaminergic neurons. To identify Lmx1a binding proteins, Lmx1a is first contacted with a candidate protein, and the presence or absence of binding is detected. In this step, Lmx1a can be immobilized onto a support. The candidate proteins are not especially restricted, and comprise, for example, gene library expression products, natural substances derived from marine organisms, extracts of various cell types, known compounds and peptides, natural substances derived from plants, body tissue extracts, microbial culture supernatants, and peptide groups randomly produced by the phage display method and such (J. Mol. Biol. 222: 301-10 (1991)). However, when searching for proteins that actually interact with Lmx1a, proteins expressed in dopaminergic neurons are particularly preferably selected as the candidate proteins. Also, candidate proteins may be labeled for ease of binding detection.

<Inhibition of Lmx1a Expression>

The present invention revealed that Lmx1a is expressed in dopaminergic neurons at all stages of differentiation, from proliferating dopaminergic neuron progenitor cells to cells after cell cycle exit. As a result, Lmx1a was considered to be involved in in vivo differentiation, maturation and/or function of dopaminergic neurons. Therefore, substances that inhibit the expression of the Lmx1a gene may be utilized to control in vivo, ex vivo, and in vitro differentiation, maturation and/or function of dopaminergic neurons. Examples of substances capable of inhibiting gene expression include antisense nucleic acids, ribozymes, and double-stranded RNAs (small interfering RNAs; siRNAs). Thus, the present invention provides such antisense nucleic acids, ribozymes, and double-stranded RNAs.

Examples of antisense mechanisms that suppress target gene expression include: (1) the inhibition of transcription initiation via triplex formation, (2) transcription suppression through hybrid formation at sites of local open-loop structures formed by RNA polymerase, (3) transcription inhibition through hybrid formation with RNA during synthesis, (4) splicing suppression through hybrid formation at intron-exon junctions, (5) splicing suppression through hybrid formation at sites of spliceosome formation, (6) suppression of mRNA migration to the cytoplasm through hybrid formation with mRNA, (7) splicing suppression through hybrid formation at a capping site or poly A addition site, (8) suppression of translation initiation through hybrid formation at binding sites of translation initiation factors, (9) translation suppression through hybrid formation at ribosome binding sites, (10) suppression of peptide chain elongation through hybrid formation at mRNA coding regions or polysome binding sites, and (11) suppression of gene expression through hybrid formation at sites of nucleic acid/protein interaction (Hirashima and Inoue, "New Biochemistry Experiment Course 2, Nucleic Acids IV, Gene Replication and Expression", Japanese Biochemical Society edit., Tokyo Kagaku Dozin Publishing, pp. 319-347 (1993)).

The Lmx1a antisense nucleic acids of the present invention may be nucleic acids that inhibit gene expression by any of the mechanisms described in (1) to (11) above. Namely, they may contain an antisense sequence not only to a sequence of a coding region, but also to a sequence of a non-coding region of a target gene whose expression is to be inhibited. A DNA that encodes an antisense nucleic acid can be used by linking it to a suitable regulatory sequence that allows its expression. The antisense nucleic acids do not need to be completely complementary to a coding region or non-coding region of a target gene, as long as they can effectively inhibit expression of this gene. Such antisense nucleic acids have a chain length of at least 15 bp or more, preferably 100 bp or more, and more preferably 500 bp or more, and are normally within 3000 bp, preferably within 2000 bp, and more preferably within 1000 bp. It is preferable that such antisense nucleic acids share an identity of 90% or more, and more preferably 95% or more, with the complementary chain of a target gene transcription product. These antisense nucleic acids can be prepared according to the phosphorothionate method (Stein (1988) Nucleic Acids Res. 16: 3209-21) or the like, using the sequence information of the Lmx1a gene.

"Ribozyme" is a generic term referring to catalysts with an RNA component, and ribozymes are broadly classified into large ribozymes and small ribozymes. Large ribozymes cleave the phosphate-ester bonds of a nucleic acid, and after reaction, they leave a 5'-phosphoric acid and 3'-hydroxyl group at reaction sites. Large ribozymes are further classified into (1) group I intron RNAs, which carry out guanosine-initiated trans-esterification reactions at 5'-splice sites, (2) group II intron RNAs, which perform two-step self-splicing reactions via a lariat structure, and (3) RNA components of ribonuclease P, which cleave precursor tRNAs at their 5' side via hydrolysis reactions. In contrast, small ribozymes are comparatively small structural units (about 40 bp) that cleave RNAs, forming 5'-hydroxyl groups and 2'-3' cyclic phosphoric acids. Small ribozymes include, for example, hammerhead-type ribozymes (Koizumi et al. (1988) FEBS Lett. 228: 225) and hairpin-type ribozymes (Buzayan (1986) Nature 323: 349; Kikuchi and Sasaki (1992) Nucleic Acids Res. 19: 6751; Kikuchi (1992) Chemistry and Biology 30: 112). Since ribozymes are easily altered and synthesized, various modification methods are known. For example, hammerhead-type ribozymes that recognize and cleave nucleotide sequence UC, UU, or UA within a target RNA can be created by designing the substrate binding portion of a ribozyme to be complementary to an RNA sequence near the target site (Koizumi et al. (1988) FEBS Lett. 228: 225; M. Koizumi and E. Ohtsuka (1990) Protein, Nucleic Acid and Enzyme 35: 2191; Koizumi et al. (1989) Nucleic Acids Res. 17: 7059). Hairpin-type ribozymes can also be designed and produced using known methods (Kikuchi and Sasaki (1992) Nucleic Acids Res. 19: 6751; Kikuchi (1992) Chemistry and Biology 30: 112).

The antisense nucleic acids and ribozymes of the present invention can also be used in viral vectors derived from retroviruses, adenoviruses, adeno-associated viruses, and such, or non-viral vectors that use liposomes, or naked DNAs, to control gene expression in cells using ex vivo or in vivo gene therapy.

In 1998, a phenomenon was observed in nematodes in which RNAs interfered with each other, causing them to lose function (RNA interference) (Fire et al. (1998) Nature 391: 806-11). RNA interference is a phenomenon in which RNAs with the same nucleotide sequence are degraded when an artificial double-stranded RNA is introduced into cells. Subsequent research suggests that RNA silencing phenomena such as RNA interference are cellular mechanisms for eliminating defective mRNA and defending the cells against transposons, viruses, and other parasites. At present, double-stranded RNAs (small interfering RNAs; siRNAs) are used as tools for suppressing the expression of numerous genes, and methods for treating and preventing diseases by using siRNA to suppress the expression of genes that cause diseases are being studied. There are no particular limitations as to the siRNAs of the present invention, provided that they inhibit the transcription of Lmx1a mRNA. Normally, the siRNAs are a combination of a sense chain and an antisense chain to a target mRNA sequence, and they normally have a nucleotide length from at least ten to the same number of nucleotides as the target mRNA. These siRNAs are preferably 15 to 75 nucleotides long, preferably 18 to 50, and more preferably 20 to 25 nucleotides.

Known methods can be used to introduce siRNAs into cells in order to suppress Lmx1a expression. For example, a DNA encoding a single strand two RNA chains that compose an siRNA can be designed and then incorporated into an expression vector, cells can be transformed with the expression vector, and the siRNA can be expressed in the cells in the form of a double-stranded RNA with a hairpin structure. Plasmid expression vectors that continuously produce siRNAs by transfection have also been designed (for example, RNAi-Ready pSIREN Vector, and RNAi-Ready pSIREN-RetroQ Vector (BD Biosciences Clontech)).

The nucleotide sequence of an siRNA can be designed using a computer program such as that disclosed at the Ambion website (on the world wide web at ambion.com/techlib/misc/siRNA_finder.html). Kits for screening for functional siRNAs are also commercially available and can be used (for example, BD Knockout RNAi System (BD Biosciences Clontech).

All prior art documents cited herein are incorporated by reference.

EXAMPLES

Hereinbelow, the present invention will be specifically described using Examples, but it is not to be construed as being limited thereto.

Example 1

Isolation and Sequence Analysis of a Gene Specific to Dopaminergic Neuron Progenitor Cells To isolate a gene specific to dopaminergic neuron progenitor cells, the midbrain ventral region of E12.5 mice was cut into two regions in the dorsoventral direction, and genes specifically expressed in the most ventral region containing dopaminergic neurons were identified by the subtraction (N-RDA) method. One of the isolated cDNA fragments was a fragment encoding Lmx1a. Lmx1a encodes a protein comprising a LIM domain and a homeodomain.

1 N-RDA Method 1-1. Adapter Preparation

The following oligonucleotides were annealed to each other, and prepared at 100 µM:

(ad2: ad2S + ad2A, ad3: ad3S + ad3A, ad4: ad4S + ad4A, ad5: ad5S + ad5A, ad13: ad13S + ad13A)

ad2S:
(SEQ ID NO: 1)
cagctccacaacctacatcattccgt ad2A:
(SEQ ID NO: 2)
acggaatgatgt ad3S:
(SEQ ID NO: 3)
gtccatcttctctctgagactctggt ad3A:
(SEQ ID NO: 4)
accagagtctca ad4S:
(SEQ ID NO: 5)
ctgatgggtgtcttctgtgagtgtgt ad4A:
(SEQ ID NO: 6)
acacactcacag ad5S:
(SEQ ID NO: 7)
ccagcatcgagaatcagtgtgacagt -continued ad5A:
(SEQ ID NO: 8)
actgtcacactg ad13S:
(SEQ ID NO: 9)
gtcgatgaacttcgactgtcgatcgt ad13A:
(SEQ ID NO: 10)
acgatcgacagt.

1-2. cDNA Synthesis

Ventral midbrain regions were cut out of E12.5 mouse embryos (Japan SLC), and divided into two sections in the dorsoventral direction. Total RNA was prepared using an RNeasy Mini Kit (Qiagen), and double-stranded cDNA was synthesized using a cDNA Synthesis Kit (Takara). After digestion with restriction enzyme RsaI, ad2 was added. ad2S was used as the primer to amplify the cDNA using 15 PCR cycles. The conditions for amplification were: a 5-minute incubation at 72° C.; 15 reaction cycles of 30 seconds at 94° C., 30 seconds at 65° C. and two minutes at 72° C.; and finally a two-minute incubation at 72° C. In all cases, N-RDA PCR was carried out using a reaction solution containing the following components.

| | |
|---|---|
| 10× ExTaq | 5 μl |
| 2.5 mM dNTP | 4 μl |
| ExTaq | 0.25 μl |
| 100 μM primer | 0.5 μl |
| cDNA | 2 μl |
| Distilled water | 38.25 μl |

1-3. Driver Production

The ad2S-amplified cDNA was further amplified by five PCR cycles. The conditions for amplification were: incubation at 94° C. for two minutes; five reaction cycles of 30 seconds at 94° C., 30 seconds at 65° C. and two minutes at 72° C.; and finally a two-minute incubation at 72° C. The cDNA was purified using a Qiaquick PCR Purification Kit (Qiagen), and digested with RsaI. 3 μg was used for each round of subtraction.

1-4. Tester Production

The ad2S amplified cDNA was further amplified by five PCR cycles. The conditions for amplification were: incubation at 94° C. for two minutes; five reaction cycles of 30 seconds at 94° C., 30 seconds at 65° C. and two minutes at 72° C.; and a final two-minute incubation at 72° C. The cDNA was purified using a Qiaquick PCR Purification Kit (Qiagen), and digested with RsaI. ad3 was added to 60 ng of the RsaI-digested cDNA.

1-5. First Round of Subtraction

The tester and driver produced in Sections 1-3 and 1-4 above were mixed, ethanol precipitated, and then dissolved in 1 μl of 1×PCR buffer. After a five-minute incubation at 98° C., 1 μl of 1×PCR buffer+1M NaCl was added. After another five-minute incubation at 98° C., the tester and driver were hybridized at 68° C. for 16 hours.

With ad3S as the primer, the hybridized cDNA was amplified by ten cycles of DNA (incubation at 72° C. for five minutes; then ten reaction cycles of 30 seconds at 94° C., 30 seconds at 65° C. and two minutes at 72° C. Next, the amplified cDNA was digested with Mung Bean Nuclease (Takara) and purified using a Qiaquick PCR Purification Kit. Then, it was amplified by 13 PCR cycles. The conditions for amplification were: incubation at 94° C. for two minutes; 13 reaction cycles of 30 seconds at 94° C., 30 seconds at 65° C. and two minutes at 72° C.; and a final two-minute incubation at 72° C.

1-6. Normalization

1 μl of 2×PCR buffer was added to 8 ng of the cDNA amplified in the first round of subtraction. After incubating at 98° C. for five minutes, 2 μl of 1×PCR buffer+1 M NaCl was added. After another five minutes of incubation at 98° C., the cDNA was hybridized at 68° C. for 16 hours.

The hybridized cDNA was digested with RsaI and then purified using a Qiaquick PCR Purification Kit. This was then amplified by eleven PCR cycles using ad3S as the primer (incubation at 94° C. for two minutes; then eleven reaction cycles of 30 seconds at 94° C., 30 seconds at 65° C. and two minutes at 72° C.; and finally a two-minute incubation at 72° C.). The PCR product was then digested with RsaI and ad4 was then added.

1-7. Second Round of Subtraction 20 ng of the cDNA to which ad4 was added in Section 1-6 above was used as the tester and mixed with the driver of 1-3 above. The same subtraction procedure as used in Section 1-5 above was performed. Finally, ad5 was added to the cDNA following RsaI digestion.

1-8. Third Round of Subtraction 2 ng of the cDNA to which ad5 was added in Section 1-7 above was used as the tester and mixed with the driver of 1-3 above. The same subtraction procedure as used in section 1-5 above was performed. Finally, ad13 was added to the cDNA following RsaI digestion.

1-9. Fourth Round of Subtraction 2 ng of the cDNA to which ad13 was added in Section 1-8 above was used as the tester and mixed with the driver of 1-3 above. The same subtraction procedure as used in Section 1-5 above was performed. The amplified cDNA was cloned into pCRII vector (Invitrogen) and its nucleotide sequence was analyzed using the ABI3100 sequence analyzer.

Example 2

Expression Analysis of Lmx1a

1. To confirm the expression of Lmx1a in dopaminergic neurons, expression analyses of Lmx1a, Lmx1b, Nurr1, and tyrosine hydroxylase (TH) mRNAs by in situ hybridization were carried out according to the following protocol: Nurr1 and TH are markers whose expression is known to be induced for the first time in dopaminergic neuron progenitor cells after cell cycle exit. Lmx1b is a transcription factor marker known to be expressed at an extremely low level at the stage of proliferating progenitor cells, but its expression starts to increase to a high level after cell cycle exit.

First, E12.5 mouse embryos were extracted, fixed in 4% PFA/PBS(−) at 4° C. for two hours, exchanged with 20% sucrose/PBS(−) at 4° C. overnight, and embedded in O.C.T. Sections of 12 μm thickness were prepared and after drying on a slide glass, the sections were fixed again in 4% PFA at room temperature for 30 minutes. After washing with PBS, hybridization was carried out at 68° C. for 40 hours (1 μg/ml DIG-labeled RNA probe, 50% formamide, 5×SSC, 1% SDS, 50 μg/ml yeast RNA, 50 μg/ml Heparin). The sections were then washed at 68° C. (50% formamide, 5×SSC, 1% SDS) and treated with RNase (0.05 μg/ml RNase) at room temperature for five minutes. After washing with 0.2×SSC at 68° C. and washing with 1×TBST at room temperature, blocking was carried out (Blocking reagent: Roche). The sections were then reacted overnight at 4° C. with alkaline phosphatase-labeled anti-DIG antibody (DAKO), washed (1×TBST, 2 mM Levamisole), and color developed using NBT/BCIP (DAKO) as the substrate.

Figure 2:
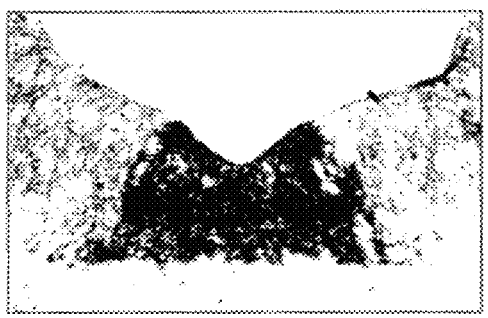
FIG. 2 is a set of photographs showing the results of analysis of Lmx1a, Lmx1b, Nurr1, and tyrosine hydroxylase (TH) mRNA expression in the midbrain of an E12.5 mouse, using in situ hybridization.
Figure 2:
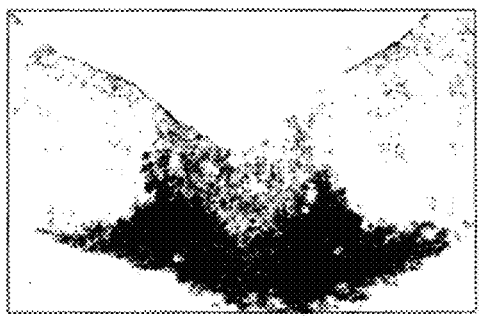
Figure 2:
Figure 2:

Expression analyses by in situ hybridization revealed that Lmx1a was expressed in the most ventral region of the midbrain, similarly to TH, Lmx1b, and Nurr1, at the E12.5 stage, which corresponds to the period of dopaminergic neuron development (FIG. 2).

2. Next, Lmx1a protein expression was confirmed using Lmx1a-specific antibodies. Furthermore, double staining with TH and En1, which are markers of dopaminergic neuron progenitor cells after cell cycle exit, was also conducted. En1 is a marker whose expression is induced for the first time in dopaminergic neuron progenitor cells after cell cycle exit.

For the anti-Lmx1a polyclonal antibodies, E. coli (JM 109 strain) were first transformed with a vector in which GST and a DNA region corresponding to amino acids 271 to 307 of Lmx1a were fused, then expression was induced by IPTG and the antigens necessary for immunization were recovered. After recovery, rabbits were immunized, their blood was collected, and antibodies were obtained from the serum by affinity purification using the GST-Lmx1a antigens that were used for immunization.

E12.5 mouse embryos were extracted, fixed in 4% PFA/PBS(−) at 4° C. for two hours, exchanged with 20% sucrose/PBS(−) at 4° C. overnight, and embedded in O.C.T. Sections of 12 μm thickness were prepared, fixed on a slide glass and dried at room temperature for 30 minutes, then infiltrated again with PBS(−). Then, blocking (Block Ace) was performed at room temperature for 30 minutes, primary antibodies were reacted at room temperature for one hour, and further reacted at 4° C. overnight. Washing with 0.1% Tween-20/PBS (−) at room temperature for 15 minutes was performed three times. Next, samples were reacted with fluorescent-labeled secondary antibodies at room temperature for one hour, washed in the same way, then washed with PBS(−) at room temperature for ten minutes, and embedded.

Figure 3:
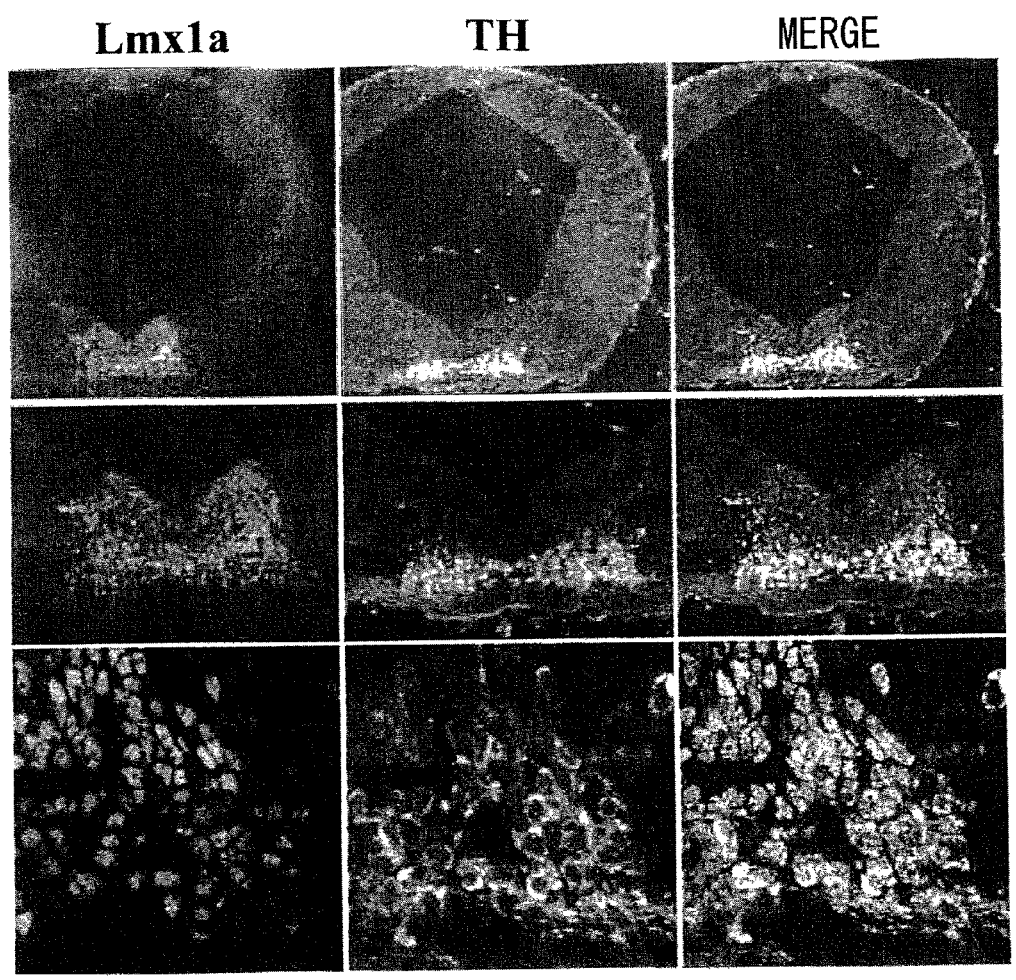
FIG. 3 is a set of photographs showing the results of coexpressing Lmx1a and tyrosine hydroxylase (TH) proteins in the midbrain of an E12.5 mouse, as detected by immunostaining.
Figure 4:
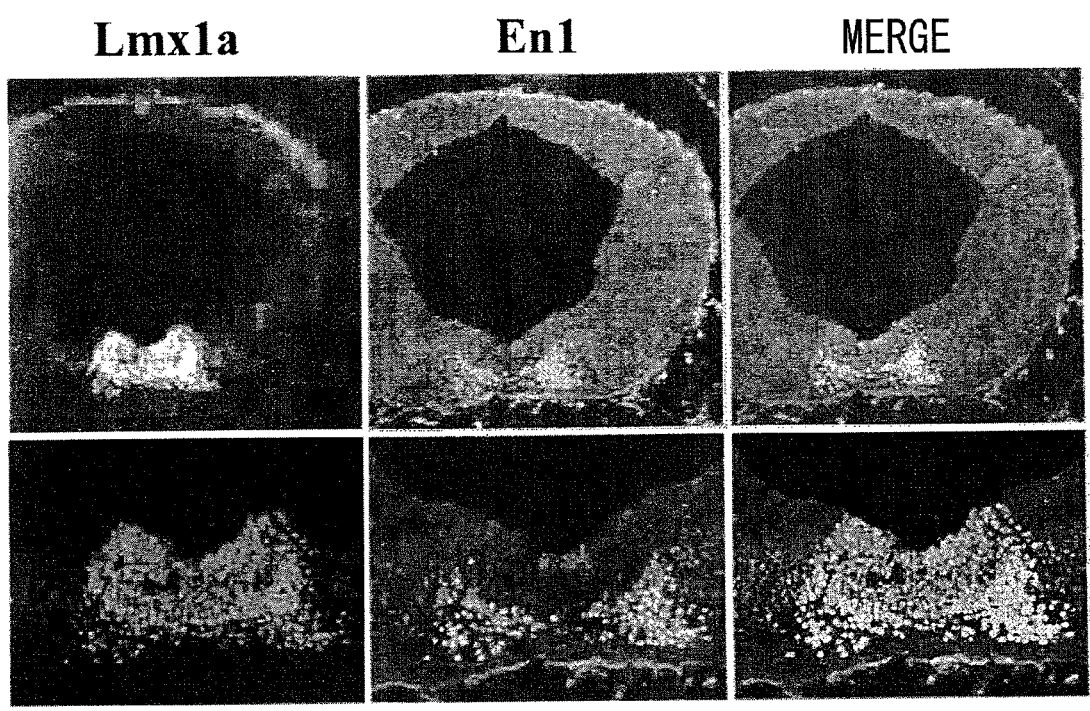
FIG. 4 is a set of photographs showing the results of coexpressing Lmx1a and En1 proteins in the midbrain of an E12.5 mouse, as detected by immunostaining.

As a result, expression patterns similar to those detected by in situ hybridization were observed (FIGS. 3 and 4). Not only the mRNAs but also the Lmx1a proteins were revealed to be expressed in the E12.5 midbrain. Double staining with TH and En1 confirmed co-expression of Lmx1a and these proteins in the same cell, and their expression regions were also revealed to be completely identical in the dorsoventral direction (FIGS. 3 and 4). In contrast with TH and En1, Lmx1a expression was also detected in the ventricular side. This region (Ventricular Zone (VZ)) comprises proliferating progenitor cells that will eventually differentiate into dopamine neurons.

3. Therefore, to confirm that Lmx1a is expressed in proliferating progenitor cells, bromodeoxyuridine (BrdU) incorporation and Lmx1a expression in E12.5 mouse midbrain were detected by immunostaining.

BrdU (Sigma) was injected (10 mg/ml in 0.9% saline injected to give 50 μg/g body weight) into the abdominal cavity of pregnant mice two hours before extracting E12.5 mouse embryos, and BrdU was incorporated into the DNA of proliferating cells. Sections were prepared in the same way as in conventional immunostaining. Lmx1a proteins were first detected using the anti-Lmx1a antibody, then sections were fixed again (2% PFA, room temperature, 30 minutes), treated with hydrochloric acid (2N HCl, 37° C., 30 minutes), and BrdU was detected using anti-BrdU antibody.

Figure 5:
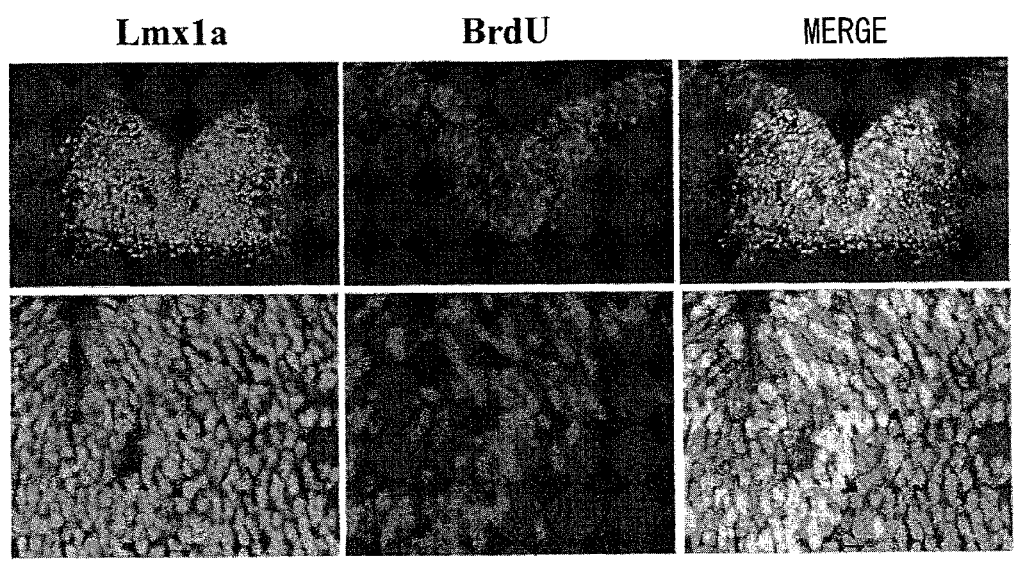
FIG. 5 is a set of photographs showing the results of Lmx1a expression and BrdU incorporation in the midbrain of an E12.5 mouse, as detected by immunostaining. Lmx1a was shown to be expressed in proliferating dopamine neuron progenitor cells.

The results revealed that BrdU was incorporated in many Lmx1a-positive cells of the VZ region (FIG. 5).

4. Lmx1a expression in dopaminergic neurons of mice after birth was also examined. Lmx1a expression was detected by the method of 1, described above, except that the midbrain sections of 7-day-old (P7) mice were used instead of those of E12.5 mouse embryos, and the dopaminergic neuron marker DAT was used as the marker for comparison. DAT is a marker known to be expressed only once dopaminergic neurons have advanced into maturation.

Figure 6:
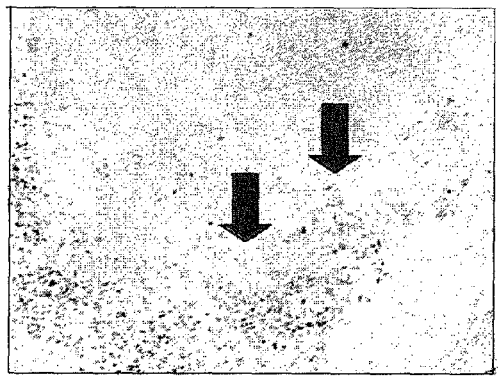
FIG. 6 is a set of photographs showing the results of Lmx1a and DAT mRNA expression in the midbrain of a mouse seven days after birth, as detected by in situ hybridization. The arrow indicates the substantia nigra region of the midbrain.
Figure 6:
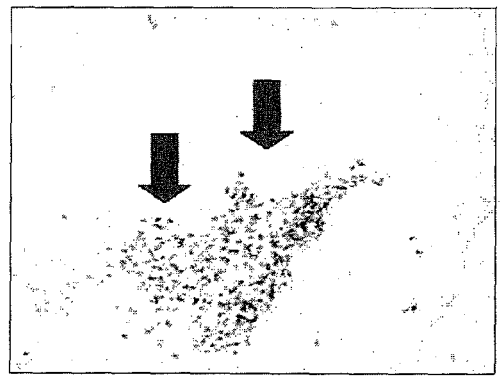

The results revealed that Lmx1a is expressed in regions where DAT is expressed (FIG. 6).

5. Furthermore, to examine whether Lmx1a is also specifically expressed in dopaminergic neurons in humans, RT-PCR was performed using RNA from the adult brain region.

cDNA synthesis was performed for 1 μg of total RNA from various regions of the human brain purchased from Clontech using RNA PCR kits (TaKaRa). Then, using cDNA equivalent to 10 ng, 1 ng, and 0.1 ng as a template, PCR was performed in the reaction system below.

| | |
|---|---|
| 10x ExTaq | 2 μl |
| 2.5 mM dNTP | 1.6 μl |
| ExTaq | 0.1 μl |
| 100 μM primers | 0.2 μl each |
| cDNA | 1 μl |
| Distilled water | 14.9 μl |

The conditions for amplification were: a two-minute incubation at 94° C.; 37 reaction cycles of 30 seconds at 94° C., 30 seconds at 65° C. and 30 seconds at 72° C.; and a final two-minute incubation at 72° C.

The primer sequences used were as follows:

```
Human Lmx 1a:
                              (SEQ ID NO: 11)
    TGAAGAAAGTCTCTGCAAGTCAGCCC/

(SEQ ID NO: 12)
    CACCACCGTTTGTCTGAGCAGAGCTC.
```

Figure 7:
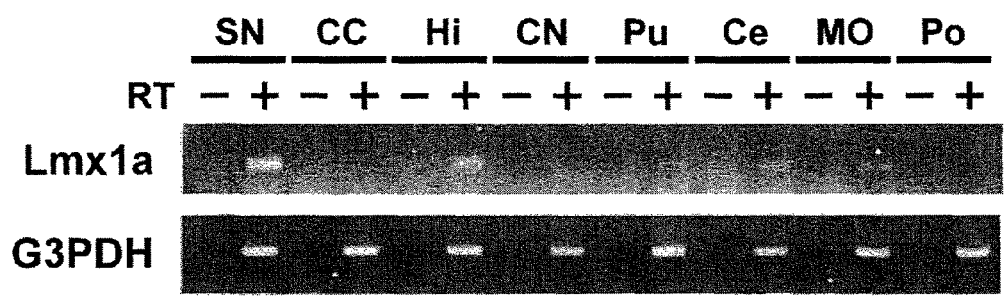
FIG. 7 is a set of photographs showing the results of Lmx1a expression in the human adult brain region, as detected by RT-PCR. SN: substantia nigra, Pu: putamen, CC: cerebral cortex, Ce: cerebellum, Hi: hippocampus, MO: medulla oblongata, CN: caudate nucleus, and Po: pons.

The results revealed that in humans also, Lmx1a is expressed in the midbrain substantia nigra region, where dopaminergic neurons are present (FIG. 7). Further, expression similar to that of mice was also shown in other brain regions, such as the hippocampus, and the expression was also revealed to be maintained in the dopaminergic neurons of adults.

Figure 8:
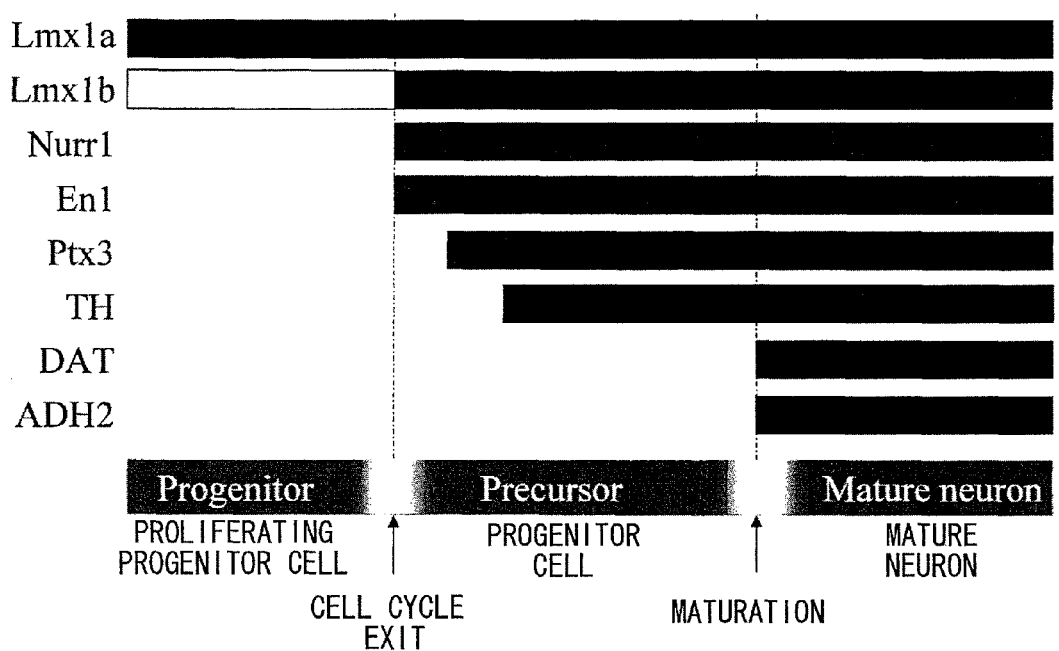
FIG. 8 schematically shows the timing of expression of Lmx1a and the dopaminergic neuron-specific marker genes. The abscissa shows the time of development and maturation of dopaminergic neurons. Lmx1a was considered to be expressed in dopaminergic neurons at all stages of differentiation.

Based on the above results, the timing of expression of Lmx1a in dopaminergic neurons was compared to that of other dopaminergic neuron markers (FIG. 8). The expression of Lmx1a is maintained from the stages of proliferating progenitor cells to cells after cell cycle exit and even in adults. On the other hand, expression of the known Nurr1, En1, Ptx3, and TH is induced for the first time after cell cycle exit and the expression of DAT and ADH2 starts only after this expression has progressed. Lmx1b expression can also be observed in proliferating progenitor cells; however, the expression level is extremely low and increases to a high level after cell cycle exit. As such, the Lmx1a expression pattern is different from known markers and Lmx1a becomes a useful marker in detecting dopaminergic neurons.

INDUSTRIAL APPLICABILITY

The expression of Lmx1a was revealed to be maintained in dopaminergic neurons from the stages of proliferating progenitor cells to cells after cell cycle exit and even in adults. On the other hand, the expression of known dopaminergic neuron markers such as Nurr1, En1, Ptx3, and TH is induced for the first time after cell cycle exit, and the expression of DAT and ADH2 starts only after this expression has progressed. Lmx1b expression can also be detected in proliferating progenitor cells; however, the expression level is extremely low and increases to a high level after cell cycle exit. The Lmx1a expression pattern is different from that of known markers and Lmx1a is specifically expressed in dopaminergic neurons at all differentiation stages, from proliferating dopaminergic neuron progenitor cells to cells after cell cycle exit. Thus Lmx1a is considered to be a useful marker in detecting dopaminergic neurons (see FIG. 8).

Lmx1a is a marker expressed at an earlier stage than conventional markers. Therefore, by using the expression of Lmx1a in cells as an index, it becomes possible to select cells suitable in terms of safety, survival rate, and network formation ability for use in transplantation therapy for neurodegenerative diseases such as Parkinson's disease. Furthermore, since Lmx1a is a marker expressed at an earlier stage, it is expected to be especially effective when screening for differentiation-inducing reagents for dopaminergic neurons. Such genes, widely expressed throughout the differentiation stages from proliferating dopaminergic neuron progenitor cells before cell cycle exit (progenitor cells at the initial stage of neuron formation) to mature cells, are considered to be useful in revealing the various factors involved in the maturation process of neurons, and the various factors involved in the expression of neuron function. Moreover, elucidation of such factors is expected to greatly contribute to the therapy of neurodegenerative diseases.

The invention claimed is:

1. A method for detecting or selecting a dopaminergic neuron and/or a progenitor thereof, wherein the method comprises the step of contacting a cellular sample with an antibody that binds to a polypeptide consisting of the amino acid sequence as set forth in SEQ ID NO:14, 16, or 18 or an amino acid sequence encoded by the nucleotide sequence consisting of SEQ ID NO:13, 15, or 17, wherein the cellular sample comprises cells from the ventral midbrain of an animal.

2. A method for detecting or selecting a dopaminergic neuron and/or a progenitor cell thereof, wherein the method comprises the steps of: (a) contacting a cellular sample that comprises cells from the ventral midbrain of an animal with an antibody that binds to the polypeptide consisting of the amino acid sequence of SEQ ID NO:14, 16, or 18 or an amino acid sequence encoded by the nucleotide sequence consisting of SEQ ID NO:13, 15, or 17; and (b) contacting the cellular sample with (i) a polynucleotide that hybridizes under the washing conditions of 0.2×SSC and 0.1% SDS at 65° C. to a nucleic acid that encodes a protein selected from the group consisting of Lmx1b, Nurr1, En1, Ptx3, and TH, or (ii) an antibody that binds to the protein.

3. The method of claim 2, which further comprises the step of: (c) contacting a cellular sample with (i) a polynucleotide that hybridizes under the washing conditions of 0.2×SSC and 0.1% SDS at 65° C. to a nucleic acid that encodes a protein selected from DAT and ADH2 or (ii) an antibody that binds to the protein.

4. The method of claim 2, wherein the protein is selected from the group consisting of Lmx1b, Nurr1, and En1.

5. A method for detecting or selecting a dopaminergic neuron and/or a progenitor cell thereof, wherein the method comprises the steps of: (a) contacting a cellular sample that comprises cells from the ventral midbrain of an animal with an antibody that binds to a polypeptide consisting of the amino acid sequence of SEQ ID NO:14, 16, or 18 or an amino acid sequence encoded by a nucleotide sequence consisting of SEQ ID NO:13, 15, or 17; and (b) contacting the cellular sample with (i) a polynucleotide that hybridizes under the washing conditions of 0.2×SSC and 0.1% SDS at 65° C. to a nucleic acid that encodes a protein selected from the group consisting of DAT and ADH2 or (ii) an antibody that binds to the protein.

6. The method of claim 1, wherein the polypeptide consists of the amino acid sequence set forth in SEQ ID NO:14 and the animal is a mouse.

7. The method of claim 6, wherein the method further comprises isolating cells bound by the antibody from the cellular sample.

8. The method of claim 1, wherein the polypeptide consists of the amino acid sequence set forth in SEQ ID NO:16 and the animal is a human.

9. The method of claim 8, wherein the method further comprises isolating cells bound by the antibody from the cellular sample.

10. The method of claim 1, wherein the polypeptide consists of the amino acid sequence set forth in SEQ ID NO:18 and the animal is a human.

11. The method of claim 10, wherein the method further comprises isolating cells bound by the antibody from the cellular sample.

12. The method of claim 2, wherein the polypeptide consists of the amino acid sequence set forth in SEQ ID NO:14 and the animal is a mouse.

13. The method of claim 2, wherein the polypeptide consists of the amino acid sequence set forth in SEQ ID NO:16 and the animal is a human.

14. The method of claim 2, wherein the polypeptide consists of the amino acid sequence set forth in SEQ ID NO:18 and the animal is a human.

15. The method of claim 5, wherein the polypeptide consists of the amino acid sequence set forth in SEQ ID NO:14 and the animal is a mouse.

16. The method of claim 5, wherein the polypeptide consists of the amino acid sequence set forth in SEQ ID NO:16 and the animal is a human.

17. The method of claim 5, wherein the polypeptide consists of the amino acid sequence set forth in SEQ ID NO:18 and the animal is a human.

* * * * *